US008273880B2

(12) United States Patent
Lee et al.

(10) Patent No.: US 8,273,880 B2
(45) Date of Patent: Sep. 25, 2012

(54) PYRAZOLE COMPOUNDS WITH INHIBITORY ACTIVITY AGAINST ROS KINASE

(75) Inventors: So Ha Lee, Seoul (KR); Kyung Ho Yoo, Seoul (KR); Chang Hyun Oh, Seoul (KR); Dong Keun Han, Seoul (KR); Ibrahim Mustafa El-Deeb, Seoul (KR); Byung Sun Park, Seoul (KR); Su Jin Jung, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 152 days.

(21) Appl. No.: 12/605,074

(22) Filed: Oct. 23, 2009

(65) Prior Publication Data

US 2011/0015395 A1 Jan. 20, 2011

(30) Foreign Application Priority Data

Jul. 17, 2009 (KR) .................. 10-2009-0065466

(51) Int. Cl.
*C07D 403/00* (2006.01)
(52) U.S. Cl. ..................................... 544/333
(58) Field of Classification Search .............. 544/333
See application file for complete search history.

(56) References Cited

FOREIGN PATENT DOCUMENTS

WO WO 2007/105058 * 9/2007
WO WO 2007/105058 A 9/2007

OTHER PUBLICATIONS

Reaction Biology Corporation, "ROS", 2006, www.reactionbiology.com (1 page).
Holland, Eric C.: "Glioblastoma multiforme: The terminator", *PNAS*, vol. 97, No. 12, Jun. 6, 2000, pp. 6242-6244.
Birchmeier, Carmen et al.: "Expression and rearrangement of the ROS1 gene in human glioblastoma cells", *Proc. Natl. Acad. Sci.*, USA, vol. 84, Dec. 1987, pp. 9270-9274.
Charest, Alan et al.: "Oncogenic targeting of an activated tyrosine kinase to the Golgi apparatus in a glioblastoma", *PNAS*, vol. 100, No. 3, Feb. 4, 2003, pp. 916-921.
Sequist, Lecia V. et al.: "EGFR Tyrosine Kinase Inhibitors in Lung Cancer: An Evolving Story", *Annu. Rev. Med.*, 2008, 59, pp. 429-442.
Hubbard, Stevan R. et al.: "Receptor tyrosine kinases: mechanisms of activation and signaling", *Current Opinion in Cell Biology*, 2007, 19, pp. 117-123.
Brard, Laurent et al.: "Induction of cytotoxicity, apoptosis and cell cycle arrest by 1-t-butyl carbamoyl, 7-methyl-indole-3-ethyl isothiocyanate (NB7M) in nervous system cancer cells", *Drug Design, Development and Theory*, 2008, 2, pp. 61-69.
Office action issued by Korean Patent Office on Apr. 11, 2011 for counterpart Korean application (priority application KR 10-2009-0065466).
McMurry, John. Organic Chemistry, Fifth Edition, Brooks/Cole Tomson Learning Publisher (2000), pp. 605-610.

* cited by examiner

*Primary Examiner* — Erich A Leeser
(74) *Attorney, Agent, or Firm* — Frommer Lawrence & Haug LLP; Ronald R. Santucci

(57) ABSTRACT

Disclosed herein are novel pyrazole compounds, pharmaceutically acceptable salts thereof, a method for preparing the same, and uses thereof as anticancer agents.

6 Claims, 1 Drawing Sheet

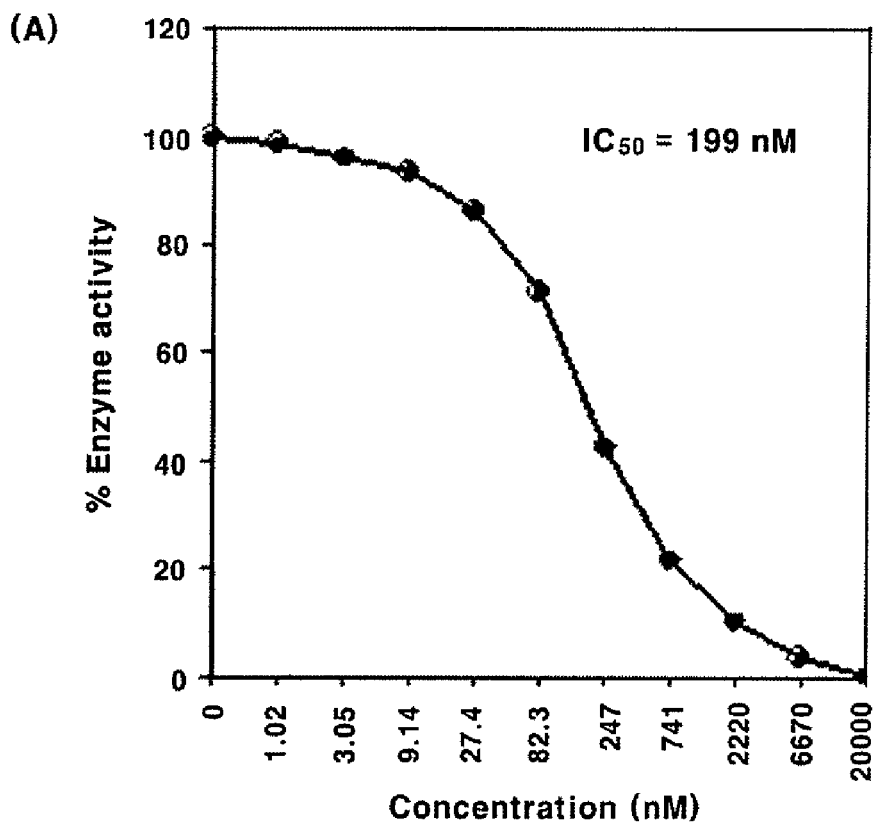
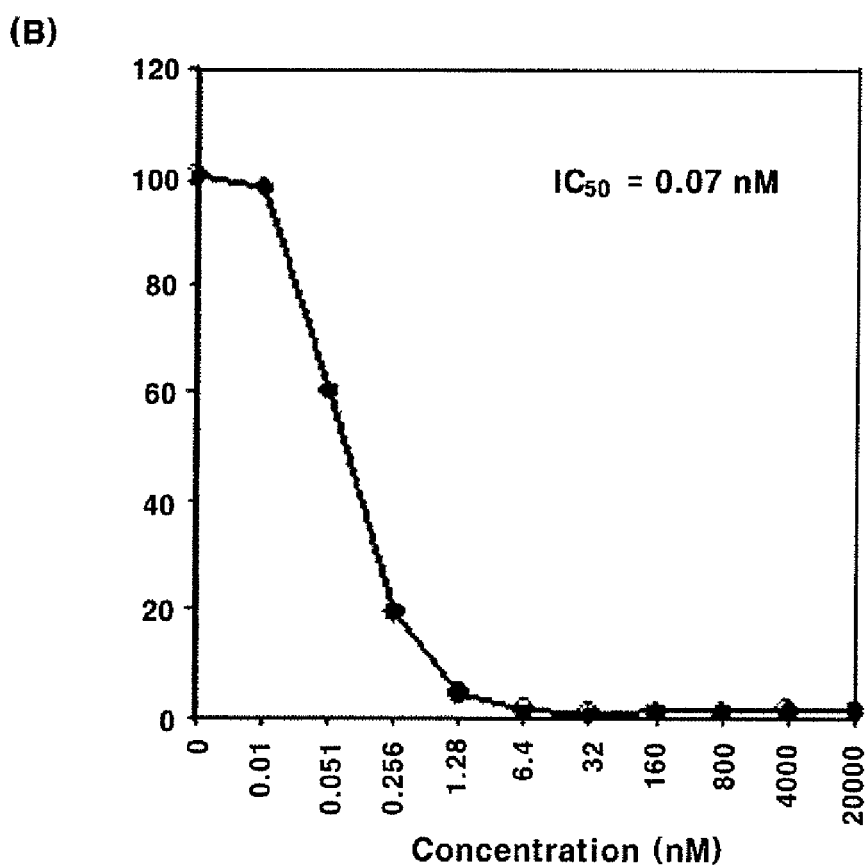

PYRAZOLE COMPOUNDS WITH INHIBITORY ACTIVITY AGAINST ROS KINASE

CROSS-REFERENCE TO RELATED APPLICATION

This application claims under 35 U.S.C. §119(a) the benefit of Korean Patent Application No. 10-2009-0065466 filed Jul. 17, 2009, the entire contents of which are incorporated herein by reference.

BACKGROUND OF THE INVENTION

1. Field of the Invention

The present invention relates to novel pyrazole compounds which have potent inhibitory activity selectively against ROS kinase, and pharmaceutically acceptable salts thereof. Also, the present invention relates to anticancer agents comprising the novel pyrazole compounds or pharmaceutically acceptable salts thereof as active ingredients, useful in the prophylaxis and treatment of cancer associated with ROS kinase. Further, the present invention is concerned with a method for the preparation of the novel pyrazole compounds or pharmaceutically acceptable salts thereof.

2. Description of the Related Art

Signal transduction is an essential biological process for normal cell growth and function. In vivo, signals can be transmitted in various manners. A typical example of signal transduction is the transmission of signals into cells by a group of trans-membrane proteins with intrinsic tyrosine kinase activity, named receptor tyrosine kinases (RTKs) [Hubbard, S. R.; Miller, W. T. Curr. Opin. Cell Biol., 2007, 19, 117]. Mutations at RTK encoding genes are associated with the incidence of several types of cancers [Sequist, L. V.; Lynch, T. J. Annu. Rev. Med., 2008, 59, 429]. Among RTKs, ROS kinase, when mutated, is causative of various kinds of CNS malignancies including brain cancer, glioblastoma multiforme and glioblastoma [Birchmeier, C.; Sharma, S.; Wigler, M. Proc. Natl. Acad. Sci. U.S.A., 1987, 84, 9270].

The ectopic expression of ROS1 receptor protein has been reported mainly in meningiomas and astrocytomas (25% of low-grade astrocytomas and 30% of malignant glioma tumors) [Charest, A.; Kheifets, V.; Park, J.; Lane, K.; Mcmahon, K.; Nutt, C. L.; Housman, D. Proc. Natl. Acad. Sci. U.S.A., 2003, 100, 916]. Glioblastoma multiforme is the most advanced astrocytic neoplasm, and is one of the most aggressive human cancers with a median survival of less than one year. These tumors are highly resistant to radiation and chemotherapy. Glioblastoma multiforme is also associated with ROS kinase activity [Holland, E. C. Proc. Natl. Acad. Sci. U.S.A., 2000, 97, 6242].

No ROS kinase inhibitors have been developed thus far. Only several compounds are known to have weak inhibitory activity against ROS enzymes. For example, IC50 values are reported to be 0.9 nM for the non-selective kinase inhibitor Staurosporine, 5,200 nM for PP2, 13,600 nM for AG1478, 48,000 nM for PDGFR I-III and 365,000 nM for D-64406 [see the website of Reaction Biology Corporation, www.reactionbiology.com].

In U.S., there are about 20,000 new astrocytomas diagnosed every year, and the number of people suffering from astrocytomas in the world has been in drastic increase in recent years. Brain cancer and spinal cord cancer account for 20% of the cases of childhood cancer. Further, 20% of childhood brain cancer and spinal cord cancer cases are found in children of the age of 15 years or less, with the most intensive incidence in children between the ages of five and ten years. Particularly, neuroblastoma, for the most part, occurs at the age of five or less, with a very high mortality [Brard, L.; Singh, R. K.; Kim, K. K.; Lange, T. S.; Sholler, G. L. S., Drug Design, Development and Therapy, 2008, 2, 61].

Leading to the present invention, intensive and thorough research into ROS kinase inhibitors, conducted by the present inventors, resulted in the finding that novel pyrazole compounds are of potent inhibitory activity against ROS kinase with a high selectivity therefor.

SUMMARY OF THE INVENTION

It is therefore an object of the present invention to provide a novel pyrazole compound having excellent selective inhibitory activity against ROS kinase.

It is another object of the present invention to provide a method for preparing a novel pyrazole compound having excellent selective inhibitory activity against ROS kinase.

It is a further object of the present invention to provide a pharmaceutical composition for the prophylaxis and treatment of cancer, comprising the novel pyrazole compound as an active ingredient.

It is still a further object of the present invention to provide the use of the pyrazole compound for the prophylaxis and treatment of human cancers including brain cancer, CNS cancer, glioblastoma multiforme and astrocytoma.

In accordance with an aspect thereof, the present invention provides a pyrazole compound, represented by the following Formula 1, or a pharmaceutically acceptable salt thereof:

[Formula 1]

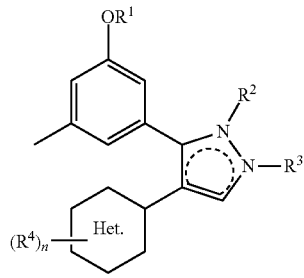

wherein

is a heteroaromatic ring having 1 to 3 nitrogen atoms;

$R^1$ is a hydrogen atom; $C_1$-$C_6$ alkyl; or acetyl;

one of $R^2$ and $R^3$ represents an electron pair forming a double bond within the pyrazole ring, while the other is a hydrogen atom; cyano; $C_1$-$C_6$ alkyl; or cyano $C_1$-$C_6$ alkyl;

$R^4$ is a hydrogen atom; a halogen atom; hydroxy; thiol; $C_1$-$C_6$ alkylsulfanyl; $C_1$-$C_6$ alkylsulfonyl; amino; $C_1$-$C_6$ alkylamino; (hydroxy$C_1$-$C_6$ alkyl)amino; (acetoxy $C_1$-$C_6$ alkyl) amino; azetidinyl; hydroxyazetidinyl; pyrrolidyl; hydroxypyrrolidyl; pyridyl; phenyl; or substituted phenyl having 1 to 3 substituents selected independently from the group consisting of cyano, amino, $C_1$-$C_6$ alkylamino, di($C_1$-$C_6$ alkyl) amino, $C_1$-$C_6$ alkylcarbonyl, $C_1$-$C_6$ alkylamide, and phenoxy; and n is an integer of 1-3, representing the number of the substituent $R^4$.

In accordance with another aspect thereof, the present invention provides an anticancer agent comprising as an active ingredient the pyrazole compound represented by Formula 1 or a pharmaceutically acceptable salt thereof.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows graphs showing ROS enzyme activities (IC50) plotted against the concentrations of the pyrazole compound of Example 10 (A) and the reference Staurosporine (B).

DESCRIPTION OF THE PREFERRED EMBODIMENTS

In a preferred embodiment of the pyrazole compound represented by Formula 1 according to the present invention, wherein

is selected from the group consisting of 2-pyridyl, 3-pyridyl, 4-pyridyl and pyrimidin-4-yl;

$R^1$ is selected from the group consisting of a hydrogen atom, methyl, ethyl, n-propyl, isopropyl, n-butyl, sec-butyl, tert-butyl, n-pentyl, isopentyl, n-hexyl, cyclohexyl, and acetyl;

one of $R^2$ and $R^3$ is an electron pair forming a double bond within the pyrazole ring, while the other is selected from the group consisting of a hydrogen atom, cyano, methyl, ethyl, n-propyl, isopropyl, n-butyl, sec-butyl, tert-butyl, cyanomethyl, cyanoethyl, and cyanopropyl;

$R^4$ is selected from the group consisting of a hydrogen atom, a chloro atom, a fluoro atom, a bromo atom, hydroxy, thiol, methylsulfanyl, ethylsulfanyl, methylsulfonyl, ethylsulfonyl, amino, methylamino, ethylamino, propylamino, butylamino, (2-hydroxyethyl)amino, (2-hydroxypropyl)amino, (2-hydroxybutyl)amino, (3-hydroxybutyl)amino, (2-acetoxyethyl)amino, (2-acetoxypropyl)amino, (2-acetoxybutyl)amino, (3-acetoxybutyl)amino, azetidinyl, 3-hydroxyazetidinyl, pyrrolidyl, 2-hydroxypyrrolidyl, 3-hydroxypyrrolidyl, 2-pyridyl, 3-pyridyl, 4-pyridyl, phenyl, 2-cyanophenyl, 3-cyanophenyl, 4-cyanophenyl, 2-aminophenyl, 3-aminophenyl, 4-aminophenyl, 2-(methylamino)phenyl, 3-(methylamino)phenyl, 4-(methylamino)phenyl, 2-(dimethylamino)phenyl, 3-(dimethylamino)phenyl, 4-(dimethylamino)phenyl, 2-(ethylamino)phenyl, 3-(ethylamino)phenyl, 4-(ethylamino)phenyl, 2-(diethylamino)phenyl, 3-(diethylamino)phenyl, 4-(diethylamino)phenyl, 2-acetophenyl, 3-acetophenyl, 4-acetophenyl, 2-(ethylcarbonyl)phenyl, 3-(ethylcarbonyl)phenyl, 4-(ethylcarbonyl)phenyl, 2-(acetylamino)phenyl, 3-(acetylamino)phenyl, 4-(acetylamino)phenyl, 2-phenoxyphenyl, 3-phenoxyphenyl, and 3-phenoxyphenyl; and n is an integer of 1, 2 or 3, representing the number of the substituent $R^4$.

Examples of the pyrazole compound represented by Formula 1 in accordance with the present invention include:
4-[2-chloro-6-(2(S)-hydroxypropylamino)-pyrimidin-4-yl]-3-(3-methoxy-5-methylphenyl)-1H-pyrazol,
[4-[2-chloro-6-(2(S)-hydroxy-propylamino)-pyrimidin-4-yl]-3-(3-methoxy-5-methylphenyl)-pyrazol-1-yl]acetonitrile,
[4-[6-(2(S)-hydroxypropylamino)-2-pyridin-3-yl-pyrimidin-4-yl]-3-(3-methoxy-5-methylphenyl)-pyrazol-1-yl]acetonitrile,
[4-[6-(2(S)-hydroxypropylamino)-2-pyridin-3-yl-pyrimidin-4-yl]-3-(3-hydroxy-5-methylphenyl)-pyrazol-1-yl]acetonitrile,
[4-[6-(2(S)-acetoxypropylamino)-2-pyridin-3-yl-pyrimidin-4-yl]-3-(3-acetoxy-5-methylphenyl)-pyrazol-3-yl]acetonitrile,
[3-(3-methoxy-5-methylphenyl)-4-(2-methylthiopyrimidine-4-yl]-1H-pyrazol,
[3-(3-methoxy-5-methylphenyl)-4-(2-methylthio-pyrimidin-4-yl)-pyrazol-1-yl]acetonitrile,
[4-(2-methanesulfonylpyrimidin-4-yl)-3-(3-methoxy-5-methylphenyl)-pyrazol-1-yl]acetonitrile,
[4-[2-(3-hydroxyazetindin-1-yl)-pyrimidin-4-yl]-3-(3-methoxy-5-methylphenyl)-pyrazol-1-yl]acetonitrile,
[4-[2-(3-hydroxyazetindin-1-yl)-pyrimidin-4-yl]-3-(3-hydroxy-5-methylphenyl)-pyrazol-1-yl]acetonitrile,
[4-[2-(3(S)-hydroxypyrrolidin-1-yl)-pyrimidin-4-yl]-3-(3-methoxy-5-methylphenyl)-pyrazol-1-yl]acetonitrile,
[4-[2-(3(S)-hydroxypyrrolidin-1-yl)-pyrimidin-4-yl]-3-(3-hydroxy-5-methylphenyl)-pyrazol-1-yl]acetonitrile,
4-(2-chloropyridin-4-yl)-3-(3-methoxy-5-methylphenyl)-1H-pyrazol,
[4-(2-chloropyridin-4-yl)-3-(3-methoxy-5-methylphenyl)-pyrazol-1-yl]acetonitrile,
[4-(2-chloropyridin-4-yl)-5-(3-methoxy-5-methylphenyl)-pyrazol-1-yl]acetonitrile,
[3-(3-methoxy-5-methylphenyl)-4-(2-phenylpyridin-4-yl)-pyrazol-1-yl]acetonitrile,
[3-(3-methoxy-5-methylphenyl)-4-(2-(pyridin-3-yl)pyridin-4-yl)-pyrazol-1-yl]acetonitrile,
[3-(3-methoxy-5-methylphenyl)-4-(2-(2-acetylphenyl)pyridin-4-yl)-pyrazol-1-yl]acetonitrile,
[3-(3-methoxy-5-methylphenyl)-4-(2-(3-acetylphenyl)pyridin-4-yl)-pyrazol-1-yl]acetonitrile,
[3-(3-methoxy-5-methylphenyl)-4-(2-(4-acetylphenyl)pyridin-4-yl)-pyrazol-1-yl]acetonitrile,
[3-(3-methoxy-5-methylphenyl)-4-(2-(2-acetamidophenyl)pyridin-4-yl)-pyrazol-1-yl]acetonitrile,
[3-(3-methoxy-5-methylphenyl)-4-(2-(3-acetamidophenyl)pyridin-4-yl)-pyrazol-1-yl]acetonitrile,
[3-(3-methoxy-5-methylphenyl)-4-(2-(4-cyanophenyl)pyridin-4-yl)-pyrazol-1-yl]acetonitrile,
[3-(3-methoxy-5-methylphenyl)-4-(2-(4-dimethylaminophenyl)pyridin-4-yl)-pyrazol-1-yl]acetonitrile,
[3-(3-methoxy-5-methylphenyl)-4-(2-(4-phenoxyphenyl)pyridin-4-yl)-pyrazol-1-yl]acetonitrile,
[5-(3-methoxy-5-methylphenyl)-4-(2-phenyl)pyridin-4-yl)-pyrazol-1-yl]acetonitrile,
[5-(3-methoxy-5-methylphenyl)-4-(2-(pyridin-3-yl)pyridin-4-yl)-pyrazol-1-yl]acetonitrile,
[5-(3-methoxy-5-methylphenyl)-4-(2-acetylphenyl)pyridin-4-yl)-pyrazol-1-yl]acetonitrile,
[5-(3-methoxy-5-methylphenyl)-4-(2-(3-acetylphenyl)pyridin-4-yl)-pyrazol-1-yl]acetonitrile,
[5-(3-methoxy-5-methylphenyl)-4-(2-(4-acetylphenyl)pyridin-4-yl)-pyrazol-1-yl]acetonitrile,

[5-(3-methoxy-5-methylphenyl)-4-(2-(2-acetamidophenyl) pyridin-4-yl)-pyrazol-1-yl]acetonitrile,
[5-(3-methoxy-5-methylphenyl)-4-(2-(3-acetamidophenyl) pyridin-4-yl)-pyrazol-1-yl]acetonitrile,
[5-(3-methoxy-5-methylphenyl)-4-(2-(4-cyanophenyl)pyridin-4-yl)-pyrazol-1-yl]acetonitrile,
[5-(3-methoxy-5-methylphenyl)-4-(2-(4-dimethylaminophenyl)pyridin-4-yl)-pyrazol-1-yl]acetonitrile,
[5-(3-methoxy-5-methylphenyl)-4-(2-(4-phenoxyphenyl) pyridin-4-yl)-pyrazol-1-yl]acetonitrile,
[3-(3-hydroxy-5-methylphenyl)-4-(2-phenylpyridin-4-yl)-pyrazol-1-yl]acetonitrile,
[3-(3-hydroxy-5-methylphenyl)-4-(2-(pyridin-3-yl)pyridin-4-yl)-pyrazol-1-yl]acetonitrile,
[3-(3-hydroxy-5-methylphenyl)-4-(2-(2-(acetylphenyl)pyridin-4-yl)-pyrazol-1-yl]acetonitrile,
[3-(3-hydroxy-5-methylphenyl)-4-(2-(3-(acetylphenyl)pyridin-4-yl)-pyrazol-1-yl]acetonitrile,
[3-(3-hydroxy-5-methylphenyl)-4-(2-(4-(acetylphenyl)pyridin-4-yl)-pyrazol-1-yl]acetonitrile,
[3-(3-hydroxy-5-methylphenyl)-4-(2-(2-(acetamidophenyl) pyridin-4-yl)-pyrazol-1-yl]acetonitrile,
[3-(3-hydroxy-5-methylphenyl)-4-(2-(3-(acetamidophenyl) pyridin-4-yl)-pyrazol-1-yl]acetonitrile,
[3-(3-hydroxy-5-methylphenyl)-4-(2-(4-(cyanophenyl)pyridin-4-yl)-pyrazol-1-yl]acetonitrile,
[3-(3-hydroxy-5-methylphenyl)-4-(2-(4-(dimethylaminophenyl)pyridin-4-yl)-pyrazol-1-yl]acetonitrile,
[3-(3-hydroxy-5-methylphenyl)-4-(2-(4-(phenoxyphenyl) pyridin-4-yl)-pyrazol-1-yl]acetonitrile,
[5-(3-hydroxy-5-methylphenyl)-4-(2-phenylpyridin-4-yl)-pyrazol-1-yl]acetonitrile,
[5-(3-hydroxy-5-methylphenyl)-4-(2-(pyridin-3-yl)pyridin-4-yl)-pyrazol-1-yl]acetonitrile,
[5-(3-hydroxy-5-methylphenyl)-4-(2-(2-acetylphenyl)pyridin-4-yl)-pyrazol-1-yl]acetonitrile,
[5-(3-hydroxy-5-methylphenyl)-4-(2-(3-acetylphenyl)pyridin-4-yl)-pyrazol-1-yl]acetonitrile,
[5-(3-hydroxy-5-methylphenyl)-4-(2-(4-acetylphenyl)pyridin-4-yl)-pyrazol-1-yl]acetonitrile,
[5-(3-hydroxy-5-methylphenyl)-4-(2-(2-acetamidophenyl) pyridin-4-yl)-pyrazol-1-yl]acetonitrile,
[5-(3-hydroxy-5-methylphenyl)-4-(2-(3-acetamidophenyl) pyridin-4-yl)-pyrazol-1-yl]acetonitrile,
[5-(3-hydroxy-5-methylphenyl)-4-(2-(4-cyanophenyl)pyridin-4-yl)-pyrazol-1-yl]acetonitrile,
[5-(3-hydroxy-5-methylphenyl)-4-(2-(4-dimethylaminophenyl)pyridin-4-yl)-pyrazol-1-yl]acetonitrile,
[5-(3-hydroxy-5-methylphenyl)-4-(2-(4-phenoxyphenyl)pyridin-4-yl)-pyrazol-1-yl]acetonitrile,
4-(2-chloropyridin-5-yl)-3-(3-methoxy-5-methylphenyl)-1H-pyrazol,
4-(2-chloropyridin-5-yl)-3-(3-methoxy-5-methylphenyl)-pyrazol-1-yl)acetonitrile,
[4-(2-(2-acetylphenyl)pyridin-5-yl)-3-(3-methoxy-5-methylphenyl)-pyrazol-1-yl]acetonitrile,
[4-(2-(3-acetylphenyl)pyridin-5-yl)-3-(3-methoxy-5-methylphenyl)-pyrazol-1-yl]acetonitrile,
[4-(2-(2-pyridin-3-yl)pyridin-5-yl)-5-(3-methoxy-5-methylphenyl)-pyrazol-1-yl]acetonitrile,
[4-(2-(2-acetylphenyl)pyridin-5-yl)-5-(3-methoxy-5-methylphenyl)-pyrazol-1-yl]acetonitrile,
[4-(2-(3-acetylphenyl)pyridin-5-yl)-5-(3-methoxy-5-methylphenyl)-pyrazol-1-yl]acetonitrile,
[4-(2-pyridin-3-yl)pyridin-5-yl)-3-(3-hydroxy-5-methylphenyl)-pyrazol-1-yl]acetonitrile,
[4-(2-(2-acetylphenyl)pyridin-5-yl)-3-(3-hydroxy-5-methylphenyl)-pyrazol-1-yl]acetonitrile,
[4-(2-(2-acetylphenyl)pyridin-5-yl)-5-(3-hydroxy-5-methylphenyl)-pyrazol-1-yl]acetonitrile,
[4-(2-(3-acetylphenyl)pyridin-5-yl)-3-(3-hydroxy-5-methylphenyl)-pyrazol-1-yl]acetonitrile,
[4-(2-(3-acetylphenyl)pyridin-5-yl)-5-(3-hydroxy-5-methylphenyl)-pyrazol-1-yl]acetonitrile, and
acid addition salts thereof.

Further, the present invention also relates to a method for the preparation of the pyrazole compound of Formula 1, as representatively illustrated in Reaction Scheme 1:

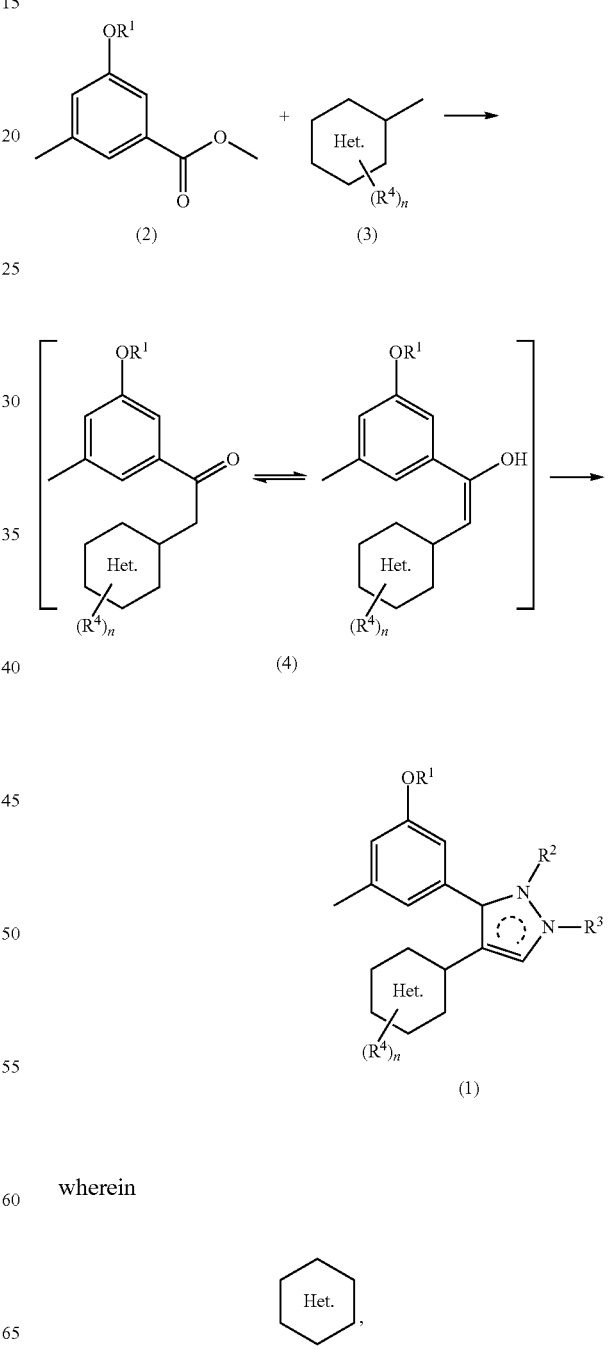

wherein $R^1$, $R^4$, and n are respectively the same as defined above, and one of $R^2$ and $R^3$ is an electron pair forming a double bond within the pyrazole ring, while the other is a hydrogen atom.

As illustrated in Reaction Scheme 1, the method for the preparation of the pyrazole compound of Formula 1 comprises: allowing a methyl 3-methoxy-5-methylbenzoate compound of Formula 2 to undergo a nucleophilic attack at its carboxylic carbon by a heteroaromatic compound of Formula 3 in the presence of lithium hexamethyldisilazide (LHMDS) to synthesize a keto-enol tautomer of Formula 4; and the keto-enol tautomer of Formula 4 in consecutive reaction with various reagent produces the pyrazole compound of Formula 1.

For the synthesis of the keto-enol tautomer of Formula 4, the nucleophilic attack may be performed at a temperature of from 0° C. to 50° C. in a typical organic solvent such as tetrahydrofuran (THF) under nitrogen atmosphere. The conversion of the keto-enol tautomer of Formula 4 into the target pyrazole compound of Formula 1 can be achieved by reaction of several steps using N,N-dimethylforamide dimethyl acetal, hydrazine monohydrate, etc.

Methyl 3-methoxy-5-methylbenzoate of Formula 2, used as a raw material in the method according to Reaction Scheme 1, may be synthesized as illustrated in Reaction Scheme 2.

[Reactoin Scheme 2]

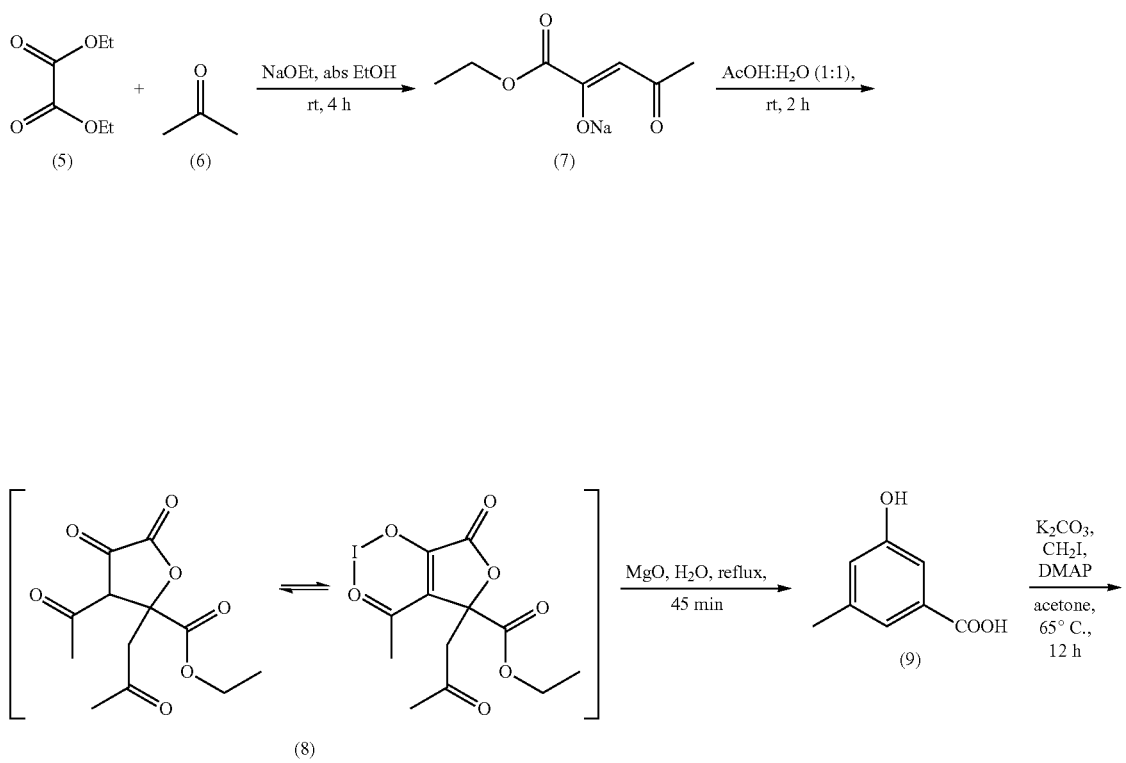

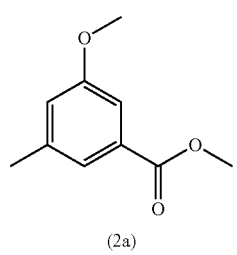

The synthesis of the methyl 3-methoxy-5-methylbenzoate of Formula 2, as seen in Reaction Scheme 2, starts with the preparation of a sodium salt of ethyl 3-acetyl-tetrahydro-4,5-dioxo-2-(2-oxopropyl)furan-2-carboxylate of Formula 7 at high yield, through the condensation of the diethyl oxalate of Formula 5 with the acetone of Formula 6 at room temperature (e.g., 20° C.-30° C.) in the presence of sodium ethoxide in absolute ethanol. Subsequently, the salt of Formula 7 is cyclized into a tautomer compound of Formula 8 by stirring at room temperature (e.g., 20° C.-30° C.) in a mixture of acetic acid and water. Afterwards, the tautomer compound of Formula 8 is allowed to undergo rearrangement and aromatization into 3-hydroxy-5-methylbenzoic acid of Formula 9 by refluxing with magnesium oxide in water. Finally, the 3-hydroxy-5-methylbenzoic acid of Formula 9 is subjected to O-methylation and methyl esterification by heating (e.g., 50° C.-80° C.) with potassium carbonate and methy iodide in the presence of a catalytic amount of DMAP in acetone to produce the methyl 3-methoxy-5-methylbenzoate of Formula 2a.

Also, various substitutents may be introduced into the pyrazole compound of Formula 1 (wherein one of $R^2$ and $R^3$ is an electron pair forming a double bond within the pyrazole ring, while the other is a hydrogen atom) prepared according to the procedure illustrated in Reaction Scheme 1. Reaction Schemes 3 to 7 are given as examples of the introduction of various substituents into the pyrazole compound moiety.

Reaction Scheme 3 shows the introduction of both a 2-hydroxypropylamino group and a chloro atom as the $R^4$ substituent to the pyrazole compound moiety by the nucleophilic substitution of the keto-enol tautomer with an amino group.

[Reaction Scheme 3]

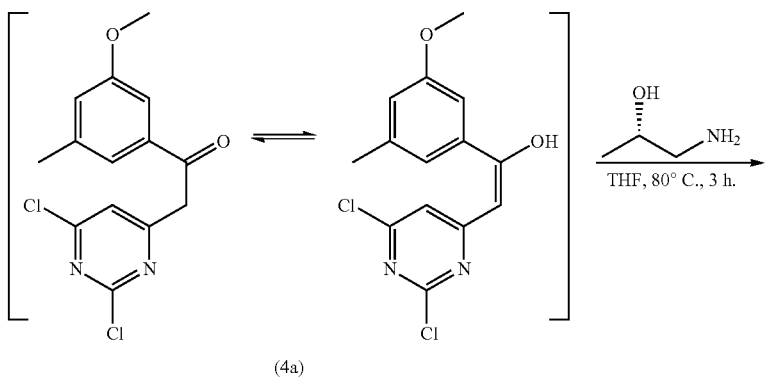

(4a)

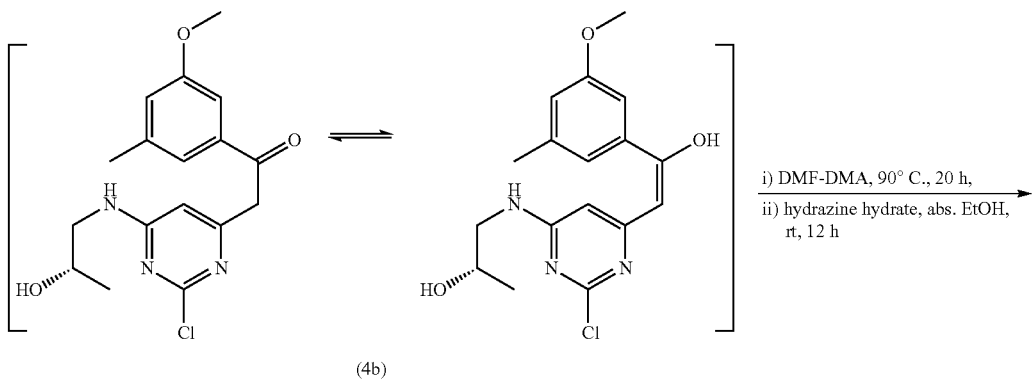

(4b)

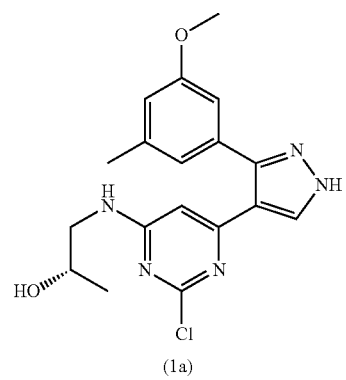

(1a)

As shown in Reaction Scheme 3, the tautomer compound of Formula 4a is subjected to nucleophilic substitution with the amino group of (S)-(+)-1-aminopropan-2-ol by heating at 50° C.-100° C. to introduce 2-hydroxypropylamino into the pyrimidine ring at C-6 position. Then, the resulting tautomer compound of Formula 4b is heated at 60° C.-120° C. with N,N-dimethylformamide dimethylacetal (DMF-DMA) and subsequently cyclized with hydrazine hydrate in absolute ethanol, with stirring at room temperature (e.g., 20° C.-30° C.), into a pyrazole compound of Formula 1a.

Reaction Scheme 4 shows the introduction of a cyanomethyl group as the $R^3$ substituent into the pyrazole compound moiety.

[Reaction Scheme 4]

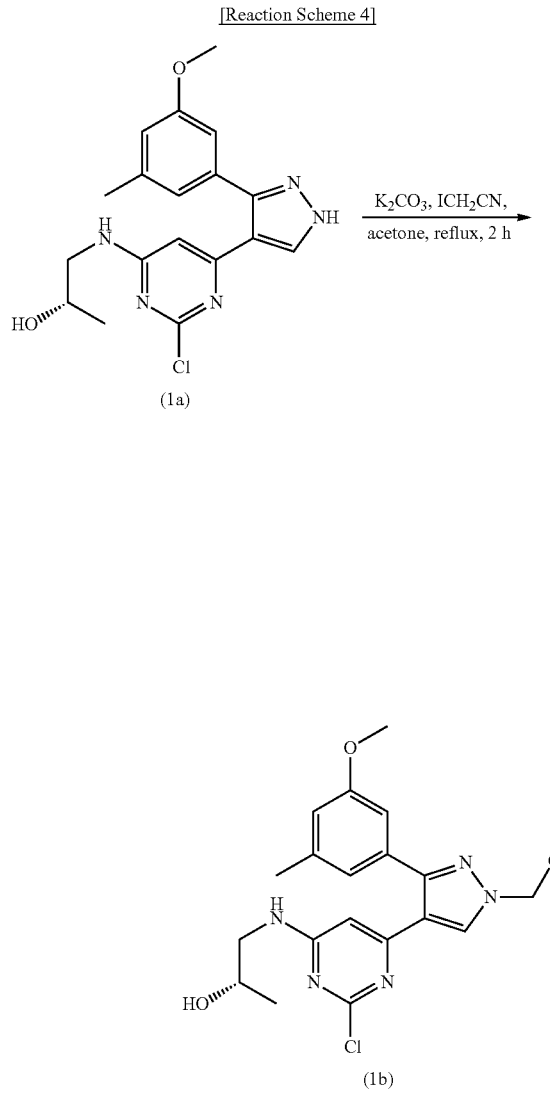

[Reaction Scheme 5]

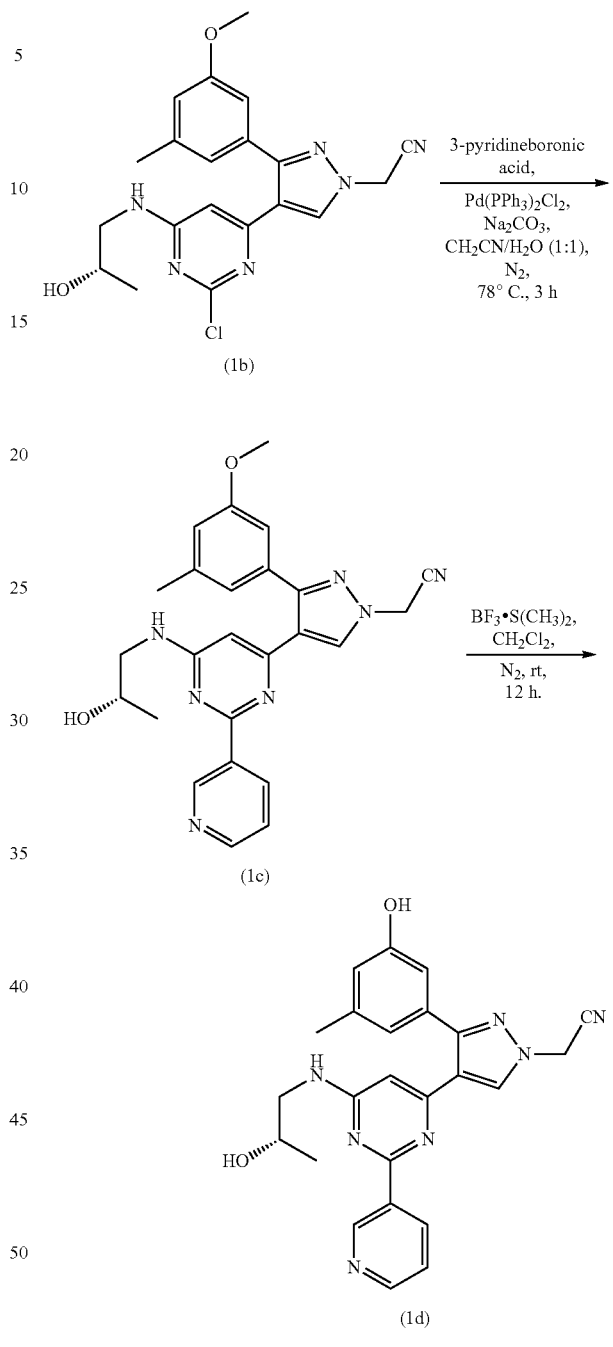

As seen in Reaction Scheme 4, the pyrazole derivative of Formula 1a is refluxed with iodoacetonitrile in the presence of potassium carbonate in acetone to introduce a cyanomethyl group into the pyrazole ring at the N-1 position to produce a pyrazole compound of Formula 1b.

Reaction Scheme 5 shows the introduction of a pyridyl group as an $R^4$ substitutent, in addition to the 2-hydroxypropylamino group, into the pyrazole compound moiety, followed by demethylation.

As seen in Reaction Scheme 5, the pyrazole compound of Formula 1b is Suzuki coupled with 3-pyridineboronic acid in the presence of a palladium catalyst and sodium carbonate in a mixed solvent of acetonitrile and water at 50° C.-100° C. under a nitrogen atmosphere to produce a pyrazole compound of Formula 1c wherein a pyridine-3-yl group is introduced at position 2 of the pyrimidine ring. Subsequently, the pyrazole compound of Formula 1c is subjected to demethylation using a borontrifluoride compound to synthesize [4-[6-(2(S)-hydroxy-propylamino)-2-pyridin-3-yl-pyrimidin-4-yl]-3-(3-hydroxy-5-methylphenyl)pyrazol-1-yl]acetonitrile, represented by Formula 1d.

Reaction Scheme 6 shows the introduction of an acetoxy group as an $R^1$ substituent and a 2-acetoxypropylamino group as an $R^4$ substituent into the pyrazole compound moiety of Formula 1d.

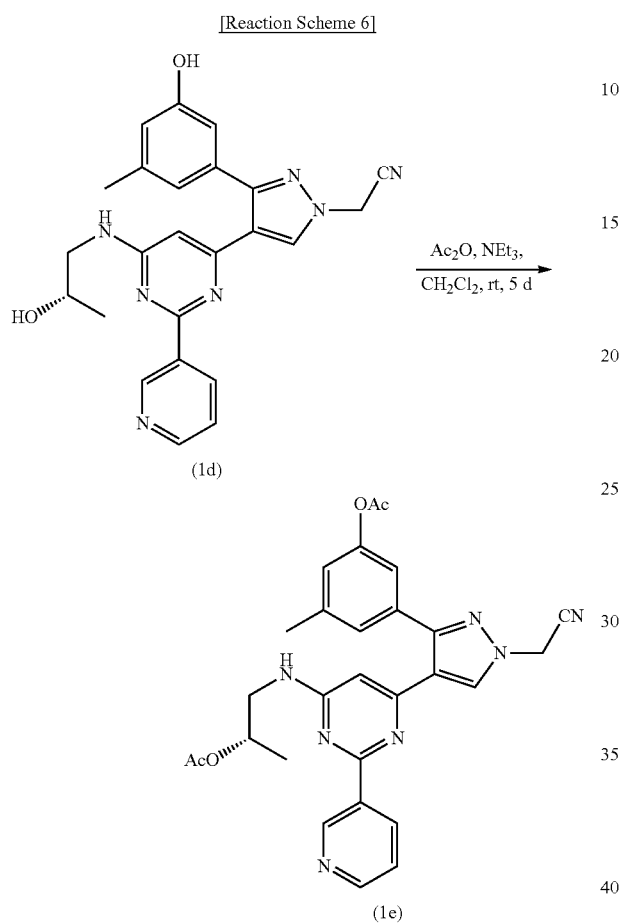

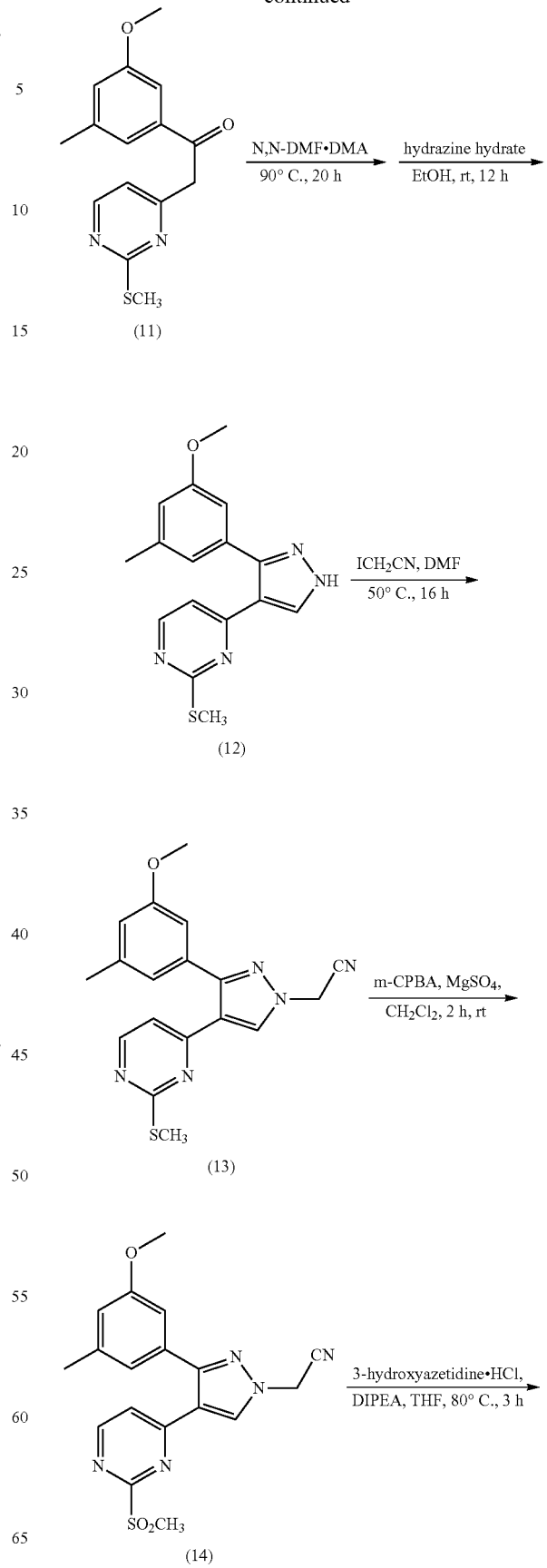

The introduction, as shown in Reaction Scheme 6, can be achieved by the acetylation of the hydroxy compound of Formula 1d with acetic anhydride in the presence of triethylamine in dichloromethane at room temperature (e.g., 20° C.-30° C.) into a pyrazole compound, represented by Formula 1e.

Reaction Scheme 7 illustrates the synthesis of a pyrazole compound of Formula 1 wherein $R^3$ is cyanomethyl and $R^4$ is 3-hydroxyazetidinyl.

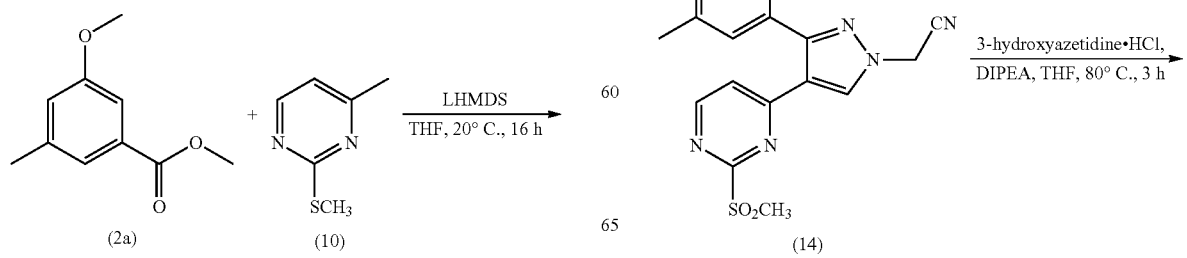

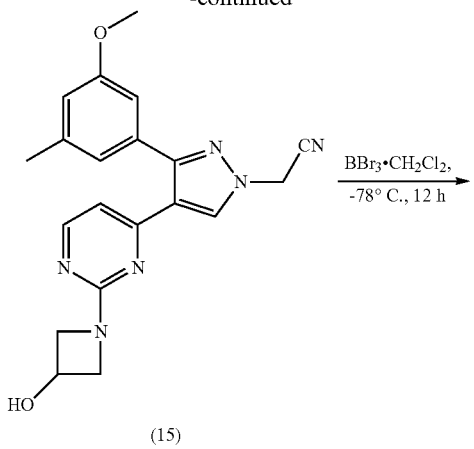

(15)

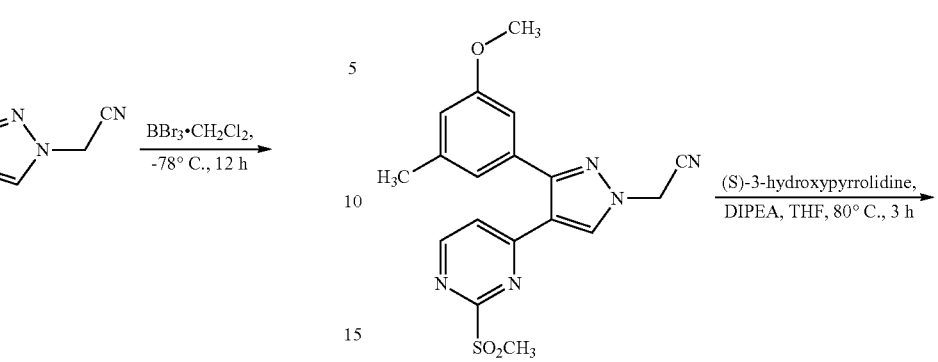

[Reaction Scheme 8]

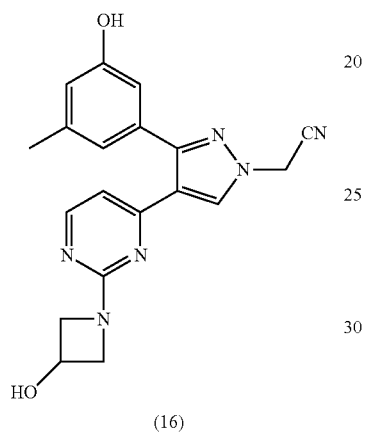

(16)

For the synthesis of the pyrazole derivative, first, as illustrated in Reaction Scheme 7, methyl 3-methoxy-5-methylbenzoate of Formula 2a is allowed to undergo a nucleophilic attack at its carboxylic carbon by the activated methylene group of 4-methyl-2-(methylthio)-pyrimidine, represented by Formula 10, at room temperature (e.g., 20° C.-30° C.) in the presence of lithium hexamethyldisilazide (LHMDS) in tetrahydrofuran to afford 1-(3-methoxy-5-methylphenyl)-2-(2-methylsulfanylpyrimidin-4-yl)ethanone. The compound of Formula 11 is converted into a pyrazole derivative through a two step successive process. In this regard, the compound of Formula 11 is heated with N,N-dimethylformamide dimethylacetal, successively followed by cyclization with hydrazine hydrate into 3-(3-methoxy-5-methylphenyl)-4-(2-methylthiopyrimidine-4-yl]-1H-pyrazol, represented by Formula 12. Thereafter, the compound of Formula 12 is converted into a cyano compound of Formula 13 by heating with iodoacetonitrile in DMF, subsequently by the oxidation of the sulfide with meta-chloroperbenzoic acid to a sulfone, [4-(2-methanesulfonylpyrimidin-4-yl)-3-(3-methoxy-5-methylphenyl) pyrazol-1-yl]acetonitrile, represented by Formula 14. The sulfone compound of Formula 14 is then subjected to nucleophilic substitution with 3-hydroxyazetidine hydrochloride, and then to demethylation with boron tribromide into [4-[2-(3-hydroxyazetindin-1-yl)-pyrimidin-4-yl]-3-(3-hydroxy-4-methylphenyl)-pyrazol-1-yl]acetonitrile, represented by Formula 16.

Reaction Scheme 8 shows the introduction of 3-hydroxypyrrolidinyl group as an $R^4$ substituent into the pyrazole compound moiety of Formula 1.

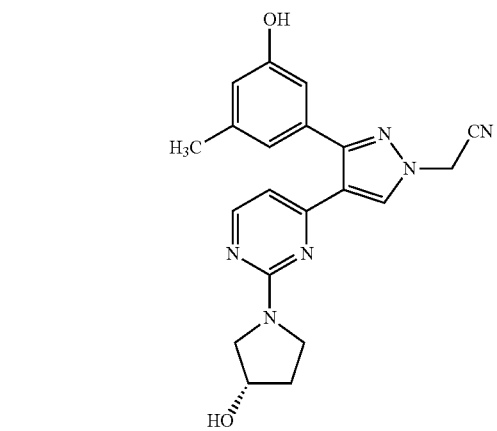

The sulfone compound of Formula 14 is, as illustrated in Reaction Scheme 8, subjected to nucleophilic substitution with (S)-hydroxypyrrolidine to produce [4-[2-(3(S)-hydroxypyrrolidin-1-yl)-pyrimidin-4-yl]-3-(3-methoxy-4-methylphenyl)-pyrazol-1-yl]acetonitrile, represented by Formula 17, which is subsequently demethylated with boron tribromide to synthesize [4-[2-(3(S)-hydroxypyrrolidin-1-yl)-pyrimidin-4-yl]-3-(3-hydroxy-4-methylphenyl)-pyrazol-1-yl]acetonitrile, represented by Formula 18.

Reaction Scheme 9 illustrates the synthesis of a pyrazole compound of Formula 1 wherein

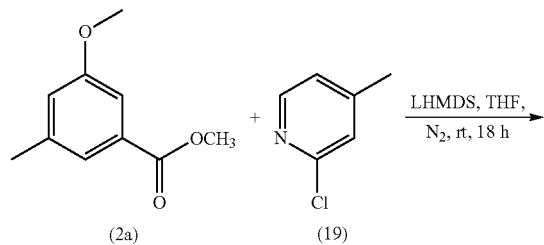

is pyridin-4-yl with various substitutents induced into the pyridine ring.

[Reaction Scheme 9]

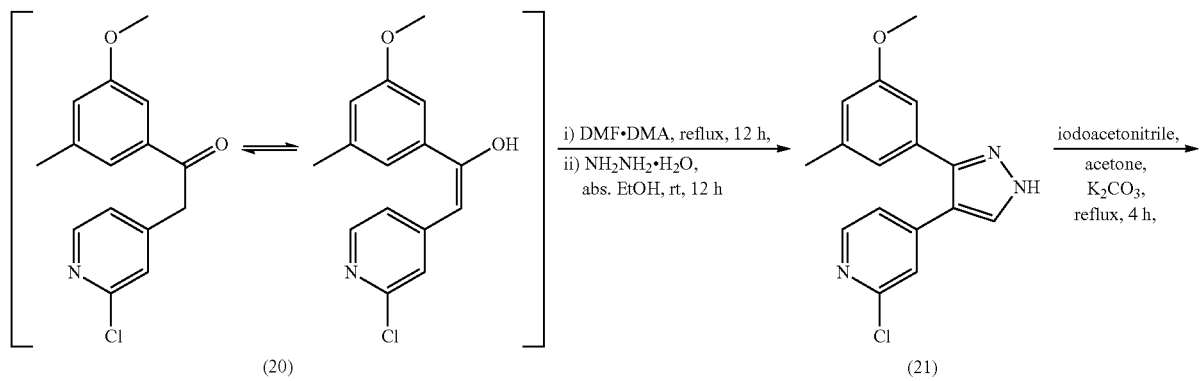

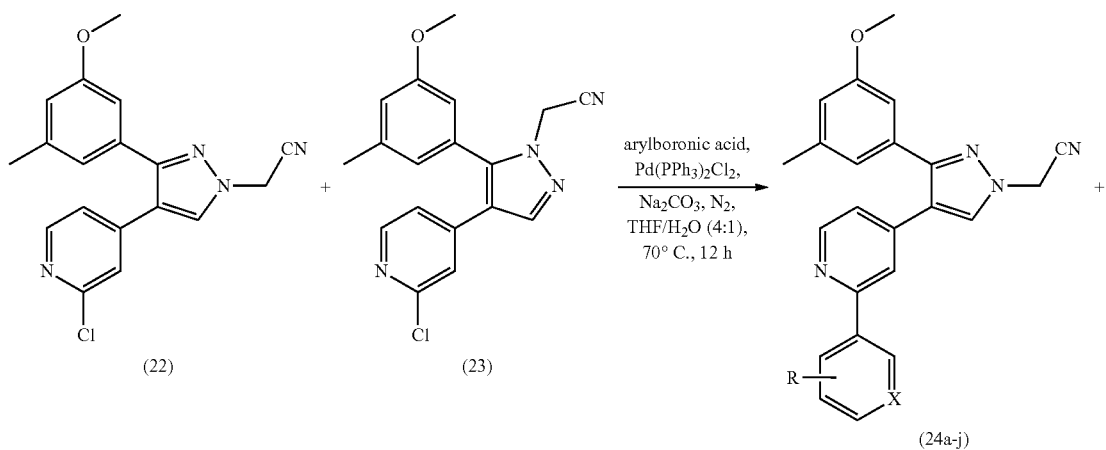

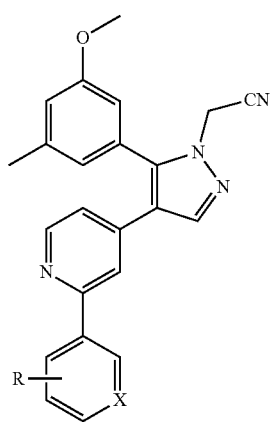 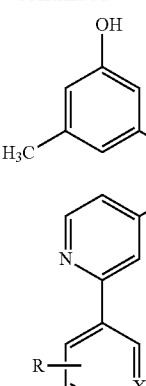 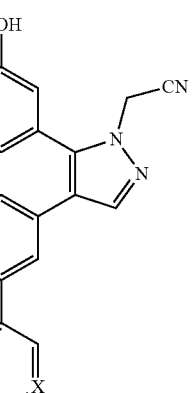

(25a-j)        (26a-j)        (27a-j)

For the synthesis of the pyrazole derivative, first, as illustrated in Reaction Scheme 9, methyl 3-methoxy-5-methyl-benzoate of Formula 2a is allowed to undergo a nucleophilic attack at its carboxylic carbon by the activated methylene group of 2-chloro-4-methylpyridine, represented by Formula 19, in the presence of lithium hexamethyldisilazide to afford 2-(2-chloropyridin-4-yl)-1-(3-methoxy-5-methylphenyl)ethanone, represented by Formula 20. The compound of Formula 20 is converted into a pyrazole derivative through a two step process: first with N,N-dimethylformamide dimethylacetal and then with hydrazine hydrate into 4-(2-chloropyridin-4-yl)-3-(3-methoxy-5-methylphenyl)-1H-pyrazol, represented by Formula 21. The reaction of the pyrazole compound of Formula 21 with iodoacetonitrile in the presence of potassium carbonate produces two regioisomers 4-(2-chloropyridin-4-yl)-3-(3-methoxy-5-methylphenyl)-(1H-pyrazol-1-yl)acetonitrile, represented by Formula 22, and 4-(2-chloropyridin-4-yl)-5-(3-methoxy-5-methylphenyl)-(1H-pyrazol-1-yl)acetonitrile, represented by Formula 23. In the presence of a palladium catalyst, the regioisomers of Formulas 22 and 23 are subjected to nucleophilic substitution with various arylboronic acids to synthesize various compounds represented by Formulas 24a-j and 25a-j. Finally, these compounds are demethylated with boron trifluoride dimethyl sulfide to synthesize target pyrazole derivatives of Formulas 26a-j and 27a-j.

Reaction Scheme 10 illustrates the synthesis of a pyrazole compound of Formula 1 wherein

is pyridin-3-yl with various substitutents induced into the pyridine ring.

[Reaction Scheme 10]

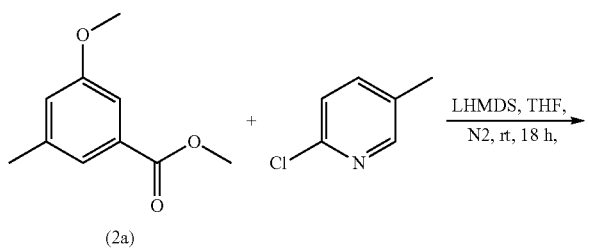

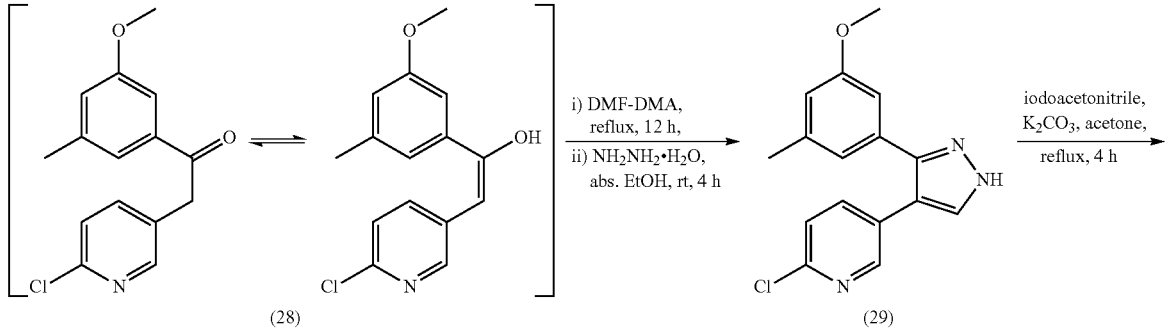

-continued

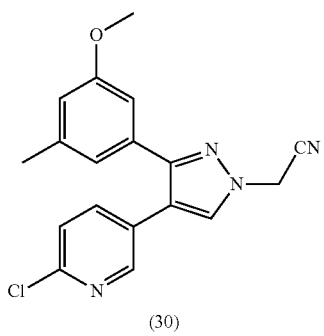
(30)

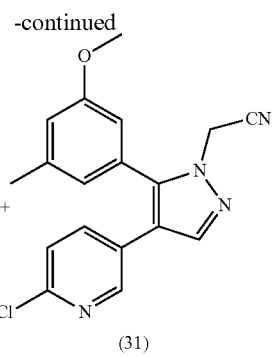
(31)

arylboronic acid,
Pd(PPh$_3$)$_2$Cl$_2$,
Na$_2$CO$_3$, N$_2$,
THF/H$_2$O (4:1),
70° C., 12 h

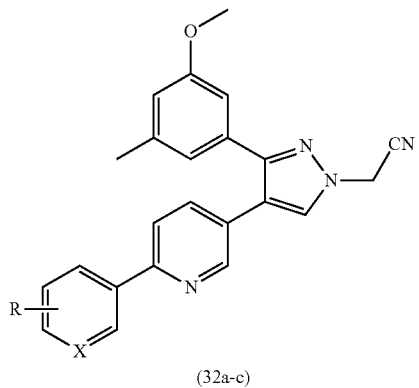
(32a-c)

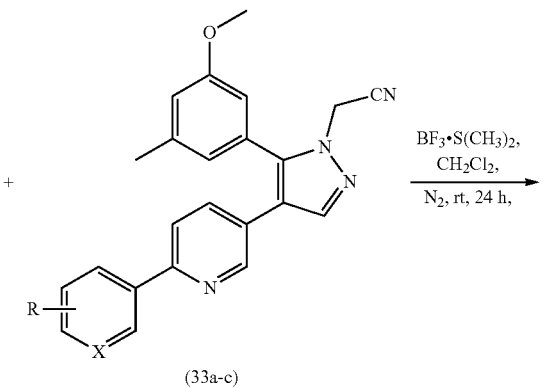
(33a-c)

BF$_3$·S(CH$_3$)$_2$,
CH$_2$Cl$_2$,
N$_2$, rt, 24 h,

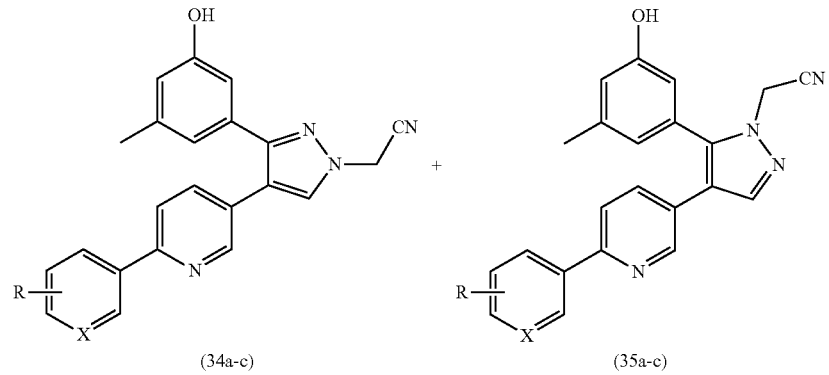
(34a-c)    (35a-c)

For the synthesis of the pyrazole derivative, first, as illustrated in Reaction Scheme 10, methyl 3-methoxy-5-methylbenzoate of Formula 2a is allowed to undergo a nucleophilic attack at its carboxylic carbon by the activated methylene group of 2-chloro-5-methylpyridine in the presence of lithium hexamethyldisilazide to afford 2-(2-chloropyridin-5-yl)-1-(3-methoxy-5-methylphenyl)ethanone, represented by Formula 28. The compound of Formula 28 is converted into a pyrazole derivative through two successive steps. In this regard, the ethanone compound of Formula 28 is heated with N,N-dimethylformamide dimethylacetal, successively followed by cyclization with hydrazine hydrate into 4-(2-chloropyridin-5-yl)-3-(3-methoxy-5-methylphenyl)-1H-pyrazol, represented by Formula 29. The reaction of the pyrazole compound of Formula 29 with iodoacetonitrile in the presence of potassium carbonate produces two regioisomers 4-(2-chloropyridin-5-yl)-3-(3-methoxy-5-methylphenyl)-1H-pyrazol-1-yl)acetonitrile, represented by Formula 30, and 4-(2-chloropyridin-5-yl)-5-(3-methoxy-5-methylphenyl)-1H-pyrazol-1-yl)acetonitrile, represented by Formula 31. In the presence of a palladium catalyst, the regioisomers of Formulas 31 and 32 are subjected to nucleophilic substitution with various arylboronic acids to synthesize various compounds represented by Formulas 32a-c and 33a-c. Finally, these compounds are demethylated with boron trifluoride dimethyl sulfide to synthesize target pyrazole derivatives of Formulas 34a-c and 35a-c.

Table 1 summarizes the structures of compounds synthesized according to Reaction Schemes 9 and 10.

TABLE 1

| Cpd. | X | R |
|---|---|---|
| 24a | H | H |
| 24b | N | H |
| 24c | H | 2-Ac |
| 24d | H | 3-Ac |
| 24e | H | 4-Ac |
| 24f | H | 2-NH—Ac |
| 24g | H | 3-NH—Ac |
| 24h | H | 4-CN |
| 24i | H | 4-N(CH$_3$)$_2$ |
| 24j | H | 4-OPh |
| 25a | H | H |
| 25b | N | H |

TABLE 1-continued

| Cpd. | X | R |
|---|---|---|
| 25c | H | 2-Ac |
| 25d | H | 3-Ac |
| 25e | H | 4-Ac |
| 25f | H | 2-NH—Ac |
| 25g | H | 3-NH—Ac |
| 25h | H | 4-CN |
| 25i | H | 4-N(CH$_3$)$_2$ |
| 25j | H | 4-OPh |
| 26a | H | H |
| 26b | N | H |
| 26c | H | 2-Ac |
| 26d | H | 3-Ac |
| 26e | H | 4-Ac |
| 26f | H | 2-NH—Ac |
| 26g | H | 3-NH—Ac |
| 26h | H | 4-CN |
| 26i | H | 4-N(CH$_3$)$_2$ |
| 26j | H | 4-OPh |
| 27a | H | H |
| 27b | N | H |
| 27c | H | 2-Ac |
| 27d | H | 3-Ac |
| 27e | H | 4-Ac |
| 27f | H | 2-NH—Ac |
| 27g | H | 3-NH—Ac |
| 27h | H | 4-CN |
| 27i | H | 4-N(CH$_3$)$_2$ |
| 27j | H | 4-OPh |
| 32a | N | H |
| 32b | H | 2-Ac |
| 32c | H | 3-Ac |
| 33a | N | H |
| 33b | H | 2-Ac |
| 33c | H | 3-Ac |
| 34a | N | H |
| 34b | H | 2-Ac |
| 34c | H | 3-Ac |
| 35a | N | H |
| 35b | H | 2-Ac |
| 35c | H | 3-Ac |

Having potent anticancer activity, as described above, the pyrazole compounds of Formula 1 in accordance with the present invention can be used for the prevention and treatment of various cancers associated with ROS kinase, such as brain cancer, CNS cancer, glioblastoma multiforme, astrocytoma, etc.

Therefore, an anticancer agent comprising the pyrazole compound of Formula 1 or a pharmaceutically acceptable salt thereof as an active ingredient falls into the scope of the present invention.

So long as it may be prepared using a typical method, any salt may be used in the present invention, for example, salts formed with inorganic acids such as hydrochloric acid, bromic acid, sulfonic acid, sodium hydrogen sulfate, phosphoric acid, nitric acid, carbonic acid, etc., with organic acids such as formic acid, acetic acid, propionic acid, oxalic acid, succinic acid, benzoic acid, citric acid, maleic acid, malonic acid, tartaric acid, gluconic acid, lactic acid, gentisic acid, fumaric acid, lactobionic acid, salicylic acid, acetylsalicylic acid (aspirin), etc., with amino acids such as glycine, alanine, valine, isoleucine, serine, cysteine, cystine, asparagines, lysine, arginine, tyrosine, proline, etc., with sulfonic acids such as methane sulfonic acid, ethane sulfonic acid, benzene sulfonic acid, toluene sulfonic acid, etc. Also, metal salts with alkaline metals such as sodium, potassium, etc. or salts with ammonium may be used as pharmaceutically acceptable salts of the present invention. Preference is given to hydrochloride or sulfonate.

The pharmaceutical composition of the present invention may further a carrier, a supplement, and/or an excipient as well as the compound of Formula 1 or a pharmaceutically acceptable salt thereof, and may be formulated into oral or non-oral dosage forms such as tablets, capsules, troches, liquids, suspensions, injections, etc. suitable for the prevention and treatment of ROS-associated cancers.

Excipients useful in the pharmaceutical composition of the present invention include a sweetener, a binder, a solubilizer, a dissolution aid, a wetting agent, an emulsifier, an isotonic agent, an absorbent, a disintegrant, an antioxidant, a preservative, a lubricant, a filter, and an aromatic, as exemplified by lactose, dextrose, sucrose, mannitol, sorbitol, cellulose, glycine, silica, talc, stearic acid, magnesium stearate, magnesium aluminum silicate, starch, gelatin, tragacanth, alginic acid, sodium alginate, methylcellulose, sodium carboxylmethylcellulose, agar, water, ethanol, polyethyleneglycol, polyvinylpyrrolidone, sodium chloride, potassium chloride, orange essence, strawberry essence, vanilla flavor, etc.

The effective dosage of the compound of Formula 1 in accordance with the present invention depends on various factors, including kinds of cancer, route of administration, patient's age, gender and weight, and severity of diseases, etc. Generally, the compound is administered in a daily dose as follows:

Typically, the compound according to the present invention may be administered to adults of 70 kg at a daily dose from 0.01 mg to 5,000 mg. The compound may be administered in a single dose or may be divided into two or three doses per day according to the instructions of a physician or pharmacist.

EXAMPLES

A better understanding of the present invention may be obtained through the following examples which are set forth to illustrate, but are not to be construed as limiting the present invention.

Example 1

Preparation of sodium ethyl 2-hydroxy-4-oxopent-2-enoate

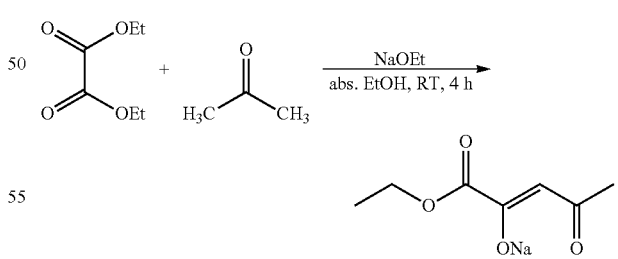

To a mixture of diethyloxalate (81 mL, 0.66 mol) and acetone (45 mL, 0.66 mol) was slowly added over 2-3 hours a solution of sodium metal (15.0 g, 0.66 mol) in absolute ethanol (330 mL) and condensation was allowed to occur with stirring at room temperature for 4 hours. The precipitate thus formed was filtered, washed with ethanol and dried to afford the title compound as a bright yellow solid (103.5 g, 87%).

m.p. 300° C. or higher; $^1$H NMR (D$_2$O) δ 1.14 (t, J=8.7 Hz, 3H), 1.83 (s, 1H), 2.07 (s, 2H), 4.08 (q, J=9.6 Hz, 2H); $^{13}$C NMR (D$_2$O) δ 13.05, 13.18, 27.65, 28.17, 62.38, 168.88, 170.94, 200.65.

Example 2

Preparation of ethyl 3-acetyl-tetrahydro-4,5-dioxo-2-(2-oxopropyl)furan-2-carboxylate

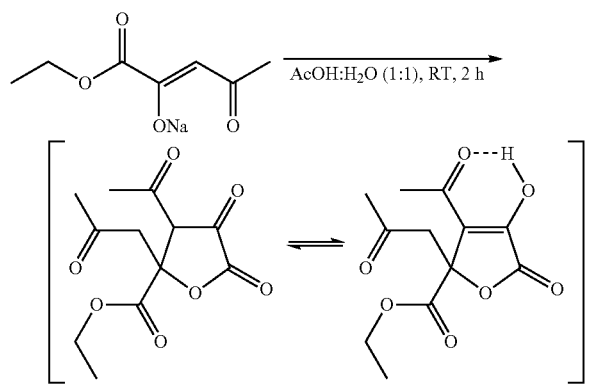

A mixture of sodium ethyl 2-hydroxy-4-oxopent-2-enoate (96 g, 0.54 mol), acetic acid (150 mL) and water (150 mL) was stirred at room temperature for 2 hours. After ice (300 g) was added to the reaction mixture, conc. sulfuric acid (60 mL) was slowly poured to form a precipitate. Recrystallization in water produced the title compound as a white solid (72.9 g, 50%).

m.p.: 87-88° C. (literature value 89-91° C.); $^1$H NMR (DMSO-d$_6$) δ 1.10 (t, J=7.1 Hz, 3H), 2.06 (s, 3H), 2.36 (s, 3H), 3.18 (d, J=18.1 Hz, 1H), 3.63 (d, J=18.1 Hz, 1H), 4.08 (q, J=5.3 Hz, 2H); $^{13}$C NMR (DMSO-d$_6$) δ 14.13, 30.30, 31.10, 62.50, 82.65, 123.12, 150.47, 167.54, 168.52, 192.64, 204.27.

Example 3

Preparation of 3-hydroxy-5-methylbenzoic acid

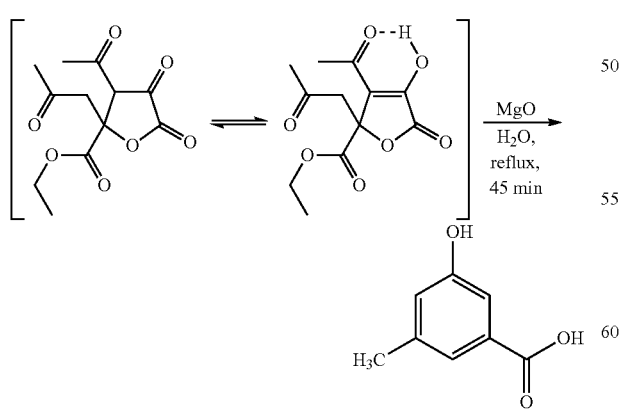

The oxo compound (57 g, 0.21 mol) was added, along with magnesium oxide (38.1 g, 0.945 mol), to water (450 mL). The resulting mixture immediately became deep reddish orange and then turned pale brown within about 15 min. After heating for 30 min with stirring, excess magnesium oxalate and magnesium oxide were filtered off. The remainder was washed with warm water and the filtrate was concentrated into 30 mL in a vacuum by distillation. The concentrate was added to a mixture of conc. HCl and water (1:1, 50 mL, v/v) to form a precipitate which was then filtered, washed with cold water and dried. Recrystallization in water afforded the title compound as a pale brown solid (13.43 g, 42%).

m.p. 202-203° C. (literature value 207-208° C.); $^1$H NMR (D$_2$O) δ 2.19 (s, 3H), 6.82 (s, 1H), 7.07 (s, 1H), 7.20 (s, 1H); $^{13}$C NMR (D$_2$O) δ 20.20, 113.00, 121.03, 122.25, 130.65, 140.55, 155.34, 170.26.

Example 4

Preparation of methyl 3-methoxy-5-methylbenzoate

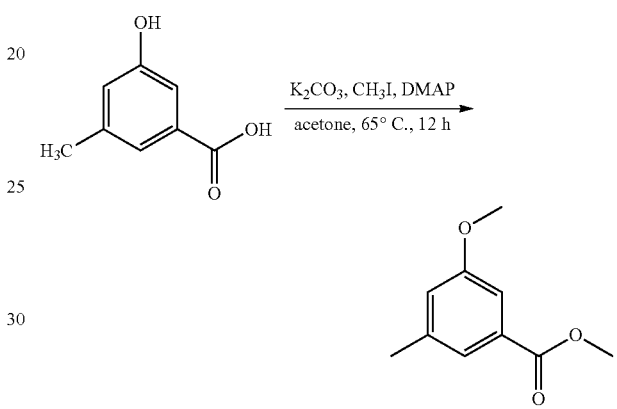

To acetone (180 mL) were added 3-hydroxy-5-methylbenzoic acid (9 g, 59.16 mmol), potassium carbonate (33 g, 237 mmol) and methyl iodide (37.2 mL, 591.6 mmol). For O-methylation, the resulting mixture was heated at 65° C. for 12 hours in the presence of a catalytic amount of dimethylaminopyridine. After vacuum distillation of the acetone, the concentrate was treated in water (300 mL) and dichloromethane (450 mL). The organic layer was dried over anhydrous magnesium sulfate and subjected to distillation. Column chromatography (silica gel, ethyl acetate-hexane 1:12 v/v) with the residue produced the title compound as a colorless liquid (9.98 g, 93.5%).

R$_f$=0.39 (hexane/EtOAc, 12:1); $^1$H NMR (CDCl$_3$) δ 2.26 (s, 3H), 3.72 (s, 3H), 3.81 (s, 3H), 6.81 (s, 1H), 7.28 (s, 1H), 7.37 (s, 1H); $^{13}$C NMR (CDCl$_3$) δ 21.34, 52.13, 55.37, 110.99, 120.23, 122.83, 131.14, 139.56, 159.51, 167.13.

Example 5

Preparation of 2-(2,6-dichloropyrimidin-4-yl)-1-(3-methoxy-5-methylphenyl)ethanone

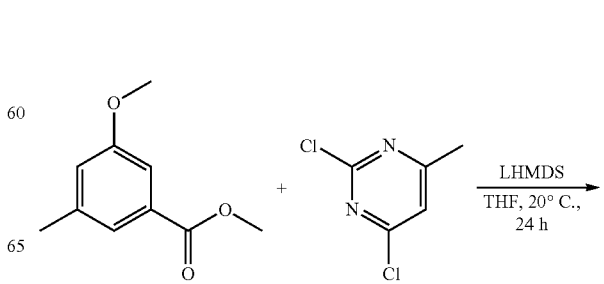

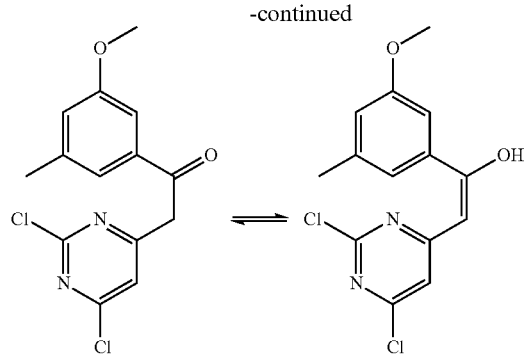

To a solution of methyl 3-methoxy-5-methylbenzoate (6.8 g, 37.7 mmol) and 2,4-dichloro-6-methylpyrimidine (7.38 g, 45.3 mmol) in tetrahydrofuran (100 mL) was dropwise added lithium hexamethyldisilazide (75.4 mL, 75.4 mmol, 1.0 M in THF) at 20° C., and stirred for 24 hours. After completion of the nucleophilic attack reaction, the reaction mixture was neutralized with a saturated ammonium chloride solution and then extracted with ethyl acetate. The organic layer was dried over anhydrous magnesium sulfate and concentrated under vacuum by distillation. Purification of the concentrate through column chromatography gave the keto/enol compound (5.9 g, 50%).

$^1$H NMR (300 MHz, CDCl$_3$) δ 2.40 (s, 3H), 3.86 (s, 3H), 5.99 (s, 1H), 6.86 (s, 1H), 6.93 (s, 1H), 7.19 (s, 1H), 7.24 (s, 1H), 13.52 (s, 1H); IR (KBr) 3443, 2975, 1558, 1118, 672 cm$^{-1}$.

Example 6

Preparation of 2-[2-chloro-6-(2(S)-hydroxypropylamino)-pyrimidin-4-yl]-1-(3-methoxy-5-methylphenyl)ethanone

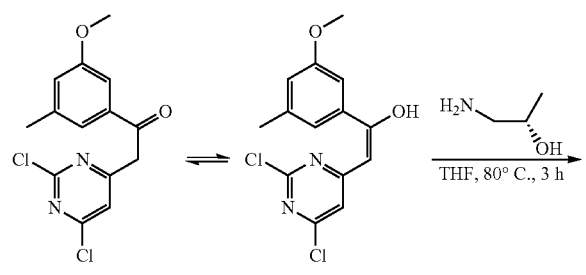

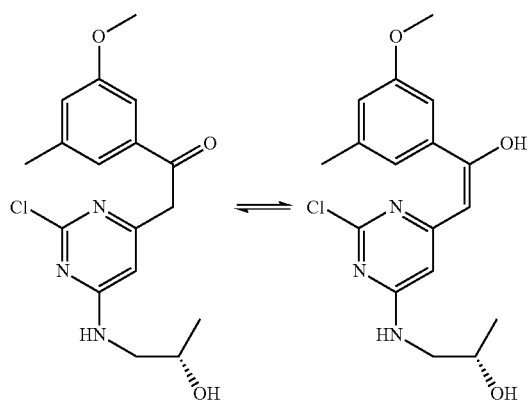

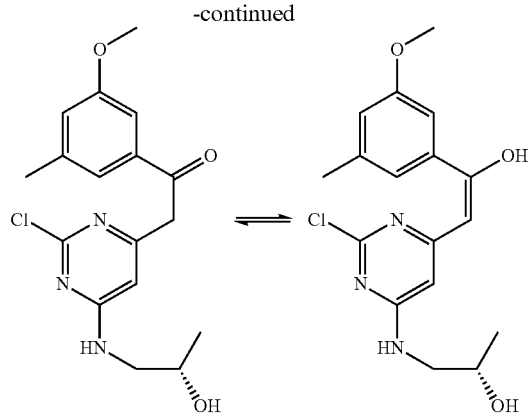

In a two-necked round-bottom flask, 2-(2,6-dichloropyrimidin-4-yl)-1-(3-methoxy-5-methylphenyl)ethanone (5.44 g, 17.54 mmol) and (S)-(+)-1-aminopropan-2-ol (4.14 mL, 52.6 mmol) were dissolved in anhydrous tetrahydrofuran (5 mL) and refluxed for 3 hours by heating. After completion of the nucleophilic substitution reaction, the reaction mixture was dissolved in ethyl acetate and washed with a saturated ammonium chloride solution and brine. The organic layer was dried over anhydrous magnesium sulfate and concentrated under vacuum by distillation. Purification of the concentrate through column chromatography gave the keto/enol tautomer compound (2.16 g, 35.2%).

$^1$H NMR (300 MHz, CDCl$_3$) δ 1.27 (s, 1H), 1.30 (d, J=6.23 Hz, 3H), 2.38 (s, 3H), 3.25-3.35 (m, 2H), 3.52-3.61 (m, 2H), 3.85 (s, 3H), 5.84 (s, 1H), 6.32 (s, 1H), 6.81 (s, 1H), 7.15 (s, 1H), 7.21 (s, 1H); IR (KBr) 3411, 3260, 2966, 1541, 1458, 1153, 814, 684 cm$^{-1}$.

Example 7

Preparation of 4-[2-chloro-6-(2(S)-hydroxypropylamino)-pyrimidin-4-yl]-3-(3-methoxy-5-methylphenyl)-1H-pyrazol

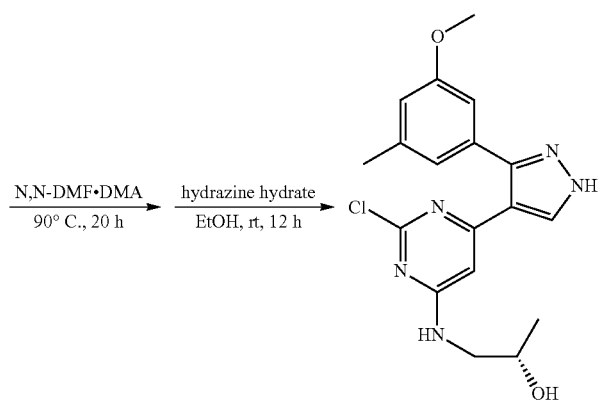

2-[2-chloro-6-(2(S)-hydroxypropylamino)pyrimidin-4-yl]-1-(3-methoxy-5-methylphenyl)ethanone (2.16 g, 6.17 mmol) was heated at 90° C. for 20 hours together with N,N-dimethylformamide dimethylacetal (8.23 mL, 61.7 mmol). Excess N,N-dimethylformamide dimethylacetal was removed by vacuum distillation, and the reaction mixture was dissolved in anhydrous ethanol (50 mL). To this solution was dropwise added hydrazine hydrate (617 μL, 12.35 mmol), and stirred at room temperature for 12 hours. After completion of the cyclization, the solvent was removed by vacuum distillation. The concentrate was treated in water and ethyl acetate, and the organic layer was dried over anhydrous magnesium sulfate, filtered and distilled under vacuum. Recrystallization in dichloromethane gave the title compound (1.01 g, 44%).

m.p. 256° C.; $^1$H NMR (300 MHz, CH$_3$OD) δ 1.11 (s, 3H), 2.38 (s, 3H), 3.13-3.17 (m, 1H), 3.42 (s, 1H), 3.80 (s, 3H), 3.83 (s, 1H), 6.55 (s, 1H), 6.88 (d, J=14.21 Hz, 3H), 8.10 (s, 1H); IR(KBr) 3416, 3166, 2928, 1572, 1284, 1153, 813, 778 cm$^{-1}$.

Example 8

Preparation of [4-[2-chloro-6-(2(S)-hydroxy-propylamino)-pyrimidin-4-yl]-3-(3-methoxy-5-methylphenyl)-pyrazol-1-yl]acetonitrile

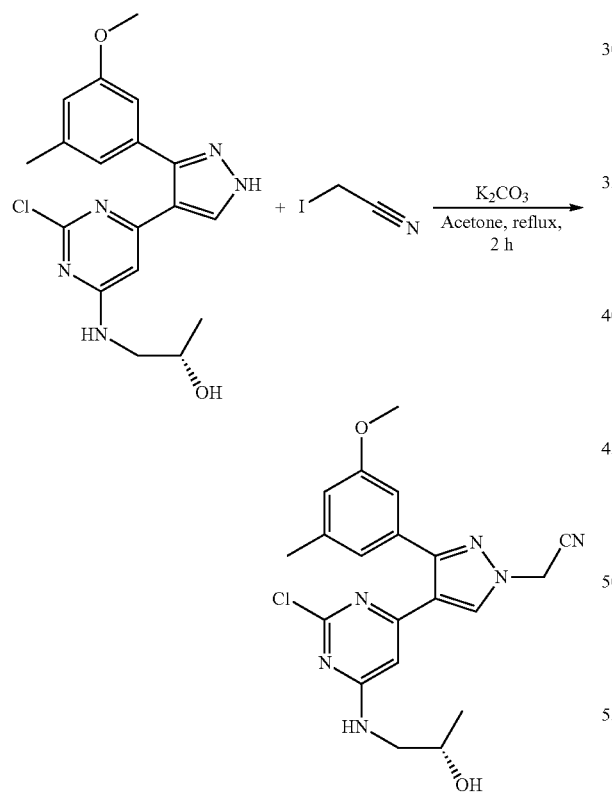

In a two-necked round-bottom flask, 4-[2-chloro-6-(2(S)-hydroxypropylamino)-pyrimidin-4-yl]-3-(3-methoxy-5-methylphenyl)-1H-pyrazol (900 mg, 2.4 mmol) was dissolved in acetone (30 mL) to which finely ground potassium carbonate (1.66 g, 12 mmol) was then added and refluxed for 2 hours. Iodoacetonitrile (0.2 mL, 3.36 mmol) was dropwise added, followed by reflux for an additional 2 hours. After completion of the reaction, the solvent was removed by vacuum distillation. The reaction mixture was dissolved in water and extracted with ethyl acetate. The organic layer was washed with brine and dried over anhydrous magnesium sulfate. The solvent was removed by vacuum distillation and the residue was purified through column chromatography to produce the title compound (430 mg, 43.4%).

m.p. 197° C.; $^1$H NMR (300 MHz, CDCl$_3$) δ 1.22 (d, J=6.1 Hz, 3H), 2.37 (s, 3H), 3.26-3.33 (m, 1H), 3.51 (s, 1H), 3.82 (s, 3H), 4.00 (s, 1H), 5.14 (s, 2H), 5.61-5.62 (m, 1H), 6.51 (s, 1H), 6.83 (d, J=15.70 Hz, 2H), 7.00 (s, 1H), 8.13 (s, 1H); IR (KBr) 3413, 2929, 1573, 1458, 1154, 783 cm$^{-1}$.

Example 9

Preparation of [4-[6-(2(S)-hydroxypropylamino)-2-pyridin-3-yl-pyrimidin-4-yl]-3-(3-methoxy-5-methylphenyl)-pyrazol-1-yl]acetonitrile

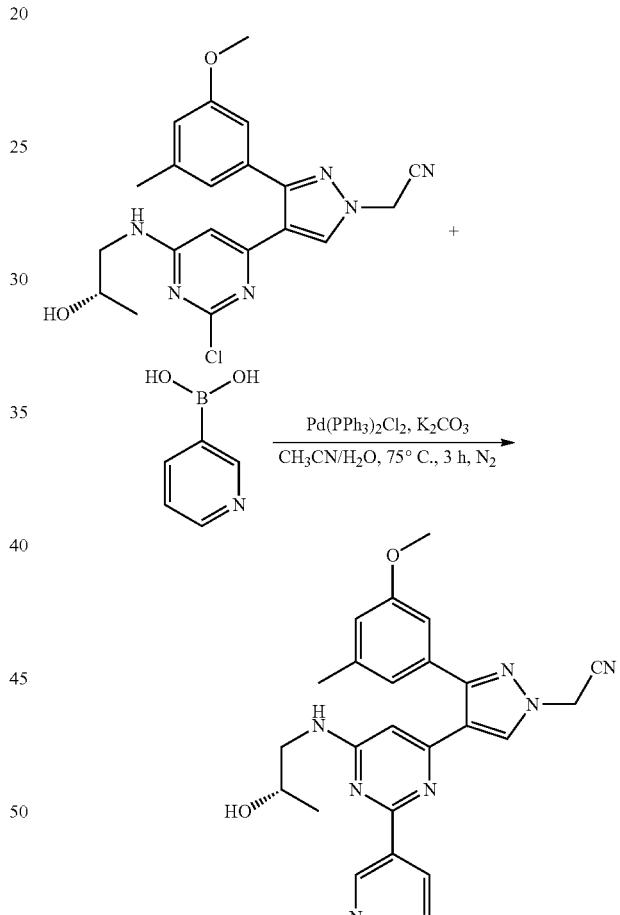

In a two-necked round-bottom flask, [4-[2-chloro-6-(2(S)-hydroxy-propylamino)-pyrimidin-4-yl]-3-(3-methoxy-5-methylphenyl)pyrazol-1-yl]acetonitrile (370 mg, 0.9 mmol), 3-pyridine boronic acid (143.27 mg, 1.17 mmol), bis(triphenylphosphine)palladium (II) dichloride (18.88 mg, 0.027 mmol), and potassium carbonate (75.98 mg, 0.72 mmol) were dissolved in a mixture of acetonitrile and water (10 mL, 1:1, v/v) through which nitrogen gas was then flowed for 10 min and heated at 75° C. for 3 hours. After completion of the Suzuki coupling reaction, the reaction mixture was dissolved in water and extracted with dichloromethane. The organic layer was washed with brine, dried over anhydrous magnesium sulfate, and distilled under vacuum. The purification of the concentrate by chromatography produced the title compound (274 mg, 67.1%).

m.p. 200° C.; $^1$H NMR (300 MHz, CDCl$_3$) δ 1.27 (d, J=6.18 Hz, 3H), 2.37 (s, 3H), 3.38-3.47 (m, 1H), 3.64 (dd, J=4.85, 6.26 Hz, 1H), 3.79 (s, 3H), 4.07-4.14 (m, 1H), 5.16 (s, 2H), 5.68 (t, J=5.78 Hz, 1H), 6.93 (t, J=22.57 Hz, 4H), 7.34-7.36 (m, 1H), 8.08 (d, J=7.94 Hz, 1H), 8.20 (s, 1H), 8.65 (d, J=4.45 Hz, 1H), 8.89 (s, 1H); IR (KBr) 3412, 2924, 1584, 1456, 1283, 1153 cm$^{-1}$.

Example 10

Preparation of [4-[6-(2(S)-hydroxypropylamino)-2-pyridin-3-yl-pyrimidin-4-yl]-3-(3-hydroxy-5-methylphenyl)-pyrazol-1-yl]acetonitrile

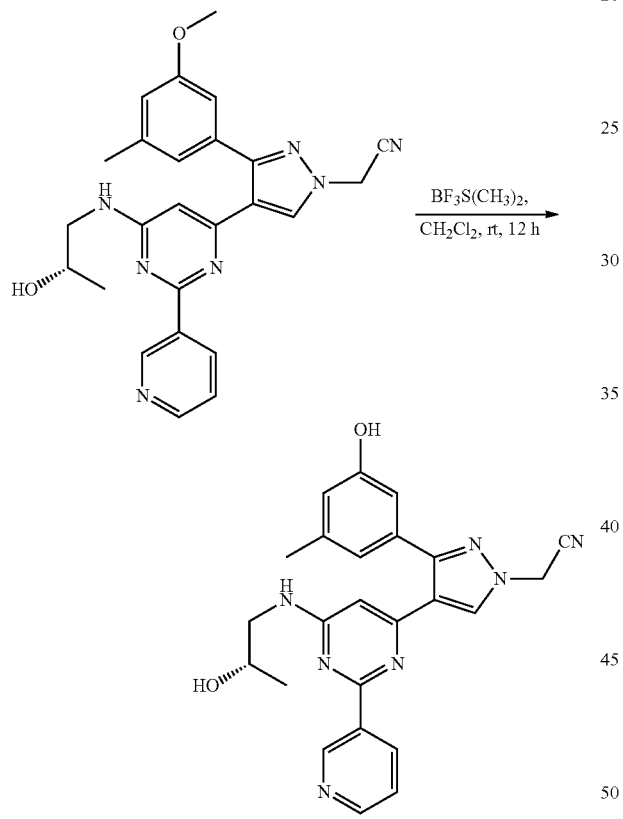

To anhydrous dichloromethane (5 mL) was added [4-[6-(2(S)-hydroxypropylamino)-2-pyridin-3-yl-pyrimidin-4-yl]-3-(3-methoxy-5-ethylphenyl)pyrazol-1-yl]acetonitrile (150 mg, 0.33 mmol) and boron trifluoride-dimethylsulfide (344 μL, 3.27 mmol) under nitrogen atmosphere. The reaction mixture was stirred for 12 hours at room temperature under nitrogen atmosphere. After completion of the demethylation, the solvent was removed by vacuum distillation, and the reaction mixture was dissolved, extracted with ethyl acetate, washed with brine, dried over anhydrous magnesium sulfate, and concentrated through vacuum distillation. Column chromatography gave the title compound (64.89 mg, 45%).

m.p. 236° C.; $^1$H NMR (400 MHz, MeOD) δ 1.09 (d, J=5.68 Hz, 3H), 2.21 (s, 3H), 3.25 (s, 1H), 3.38 (s, 1H), 3.87 (s, 1H), 5.32 (s, 2H), 6.67 (d, J=15.02 Hz, 2H), 6.76 (s, 1H), 6.86 (s, 1H), 7.38-7.41 (m, 1H), 8.00 (d, J=8.14 Hz, 1H), 8.28 (s, 1H), 8.49 (d, J=3.54 Hz, 1H), 8.81 (s, 1H); IR (KBr) 3425, 2926, 2360, 1586, 1454, 1349, 1162 cm$^{-1}$.

Example 11

Preparation of {4-[6-(2(S)-acetoxypropylamino)-2-pyridin-3-yl-pyrimidin-4-yl]-3-(3-acetoxy-5-methylphenyl)-pyrazol-3-yl}acetonitrile

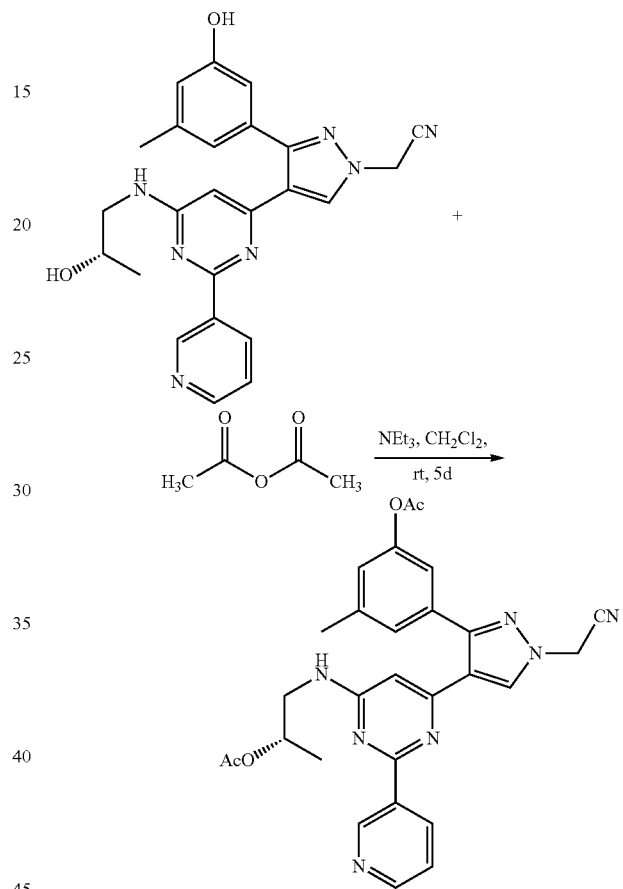

In anhydrous dichloromethane (5 mL) was dissolved [4-[6-(2(S)-hydroxypropylamino)-2-pyridin-3-yl-pyrimidin-4-yl]-3-(3-hydroxy-5-methylphenyl)pyrazol-1-yl]acetonitrile (33 mg, 0.0747 mmol), and triethylamine (31.23 μL, 0.22 mmol) and acetic anhydride (28.21 μL, 0.23 mmol) were added to the solution. The reaction mixture was stirred for 5 days at room temperature under nitrogen atmosphere. After completion of the acetylation, the reaction mixture was dissolved in water and extracted with dichloromethane. The organic layer was washed with a saturated ammonium chloride solution and a saturated sodium hydrogen carbonate solution, dried over anhydrous magnesium sulfate, concentrated by vacuum distillation, and purified through column chromatography to give the title compound (22 mg, 56%).

m.p. 230° C.; $^1$H NMR (300 MHz, CDCl$_3$) δ 1.25 (d, J=6.3 Hz, 3H), 1.99 (s, 3H), 2.18 (s, 3H), 2.33 (s, 3H), 3.49-3.53 (m, 1H), 3.65 (s, 1H), 5.09 (s, 2H), 5.11 (s, 1H), 5.38 (s, 1H), 6.85 (s, 1H), 6.94 (s, 1H), 7.08 (s, 1H), 7.24-7.30 (m, 2H), 8.05 (d, J=7.80 Hz, 1H), 8.19 (s, 1H), 8.58 (d, J=3.78 Hz, 1H), 8.96 (s, 1H); IR (KBr) 3405, 2931, 2360, 1734, 1583, 1370, 1211 cm$^{-1}$.

Example 12

Preparation of 1-(3-methoxy-5-methylphenyl)-2-(2-methylthiopyrimidin-4-yl)ethanone

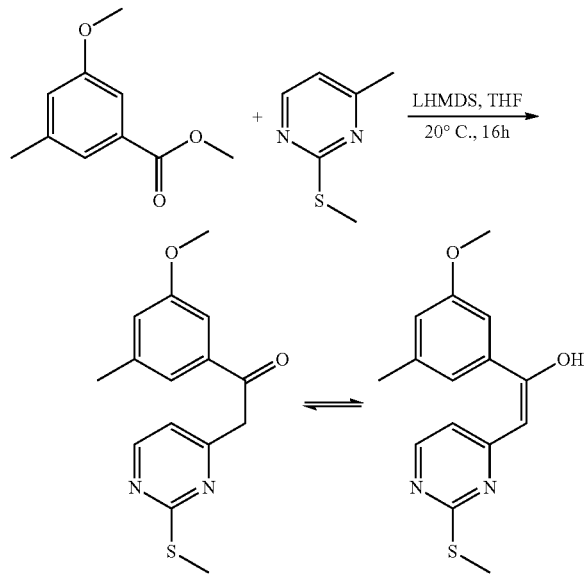

To a solution of methyl 3-methoxy-5-methylbenzoate (4.66 g, 25.86 mmol) and 4-methyl-2-(methylthio)-pyrimidine (4.32 mL, 31.03 mmol) in tetrahydrofuran (100 mL) was dropwise added lithium hexamethyldisilazide (50.68 mL, 50.68 mmol, 1M solution in THF). The reaction mixture was stirred at 20° C. for 16 hours. After completion of the nucleophilic attack reaction, the reaction mixture was neutralized with a saturated ammonium chloride solution and extracted with ethyl acetate. The organic layer was separated, dried over anhydrous magnesium sulfate, and concentrated by vacuum distillation, and the concentrate containing the title compound was used in the next reaction without further purification.

$^1$H NMR (300 MHz, CDCl$_3$) δ 2.39 (s, 3H), 2.54 (s, 3H), 3.84 (s, 3H), 4.36 (s, 2H), 6.96-6.99 (m, 2H), 7.37 (s, 1H), 7.46 (s, 1H), 8.45 (d, J=5.04 Hz, 1H); IR (KBr) 3425, 1568, 1311, 837 cm$^{-1}$.

Example 13

Preparation of [3-(3-methoxy-5-methylphenyl)-4-(2-methylthiopyrimidine-4-yl]-1H-pyrazol

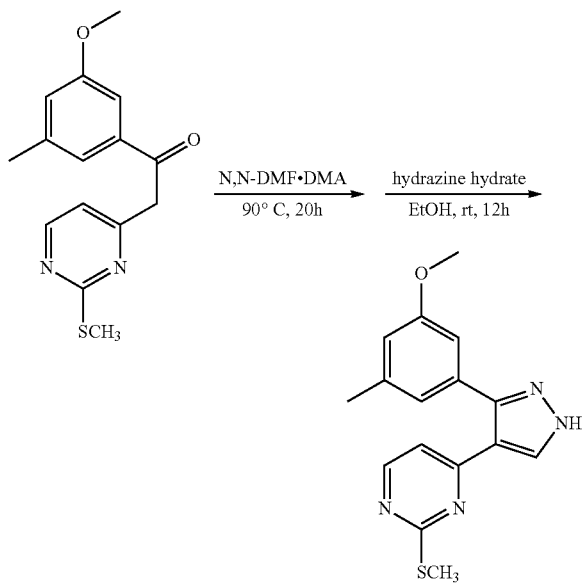

1-(3-Methoxy-5-methylphenyl)-2-(2-(methylthio)pyrimidin-4-yl)ethanone was heated with N,N-dimethylformamide dimethylacetal (34.46 mL, 258.6 mmol) at 90° C. for 20 hours with stirring. Excess N,N-dimethylformamide dimethylacetal was removed by vacuum distillation, and the reaction mixture was dissolved in anhydrous ethanol (55 mL). To this solution was dropwise added hydrazine hydrate (2.59 mL, 51.72 mmol), and stirred at room temperature for 12 hours. After completion of the cyclization, the solvent was removed by vacuum distillation. The concentrate was treated in water and ethyl acetate, and the organic layer was dried over anhydrous magnesium sulfate, filtered and distilled under vacuum. Purification by column chromatography gave the title compound (6.35 g, 78.6%).

m.p. 143° C.; $^1$H NMR (300 MHz, CDCl$_3$) δ 2.36 (s, 3H), 2.49 (s, 3H), 3.77 (s, 3H), 6.81 (s, 1H), 6.85 (s, 2H), 6.92 (s, 1H), 8.10 (s, 1H), 8.28 (s, 1H), 9.81 (s, 1H); IR (KBr) 3132, 2928, 1563, 1365, 846 cm$^{-1}$.

Example 14

Preparation of [3-(3-methoxy-5-methylphenyl)-4-(2-methylthio-pyrimidin-4-yl)-pyrazol-1-yl]acetonitrile

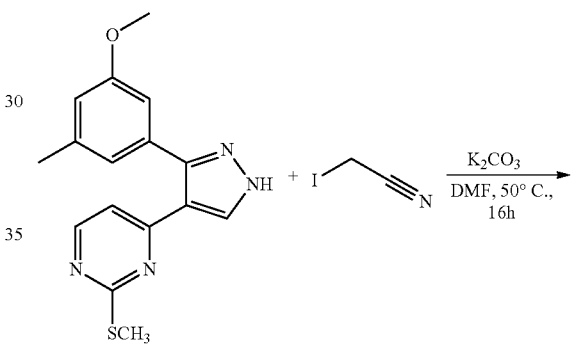

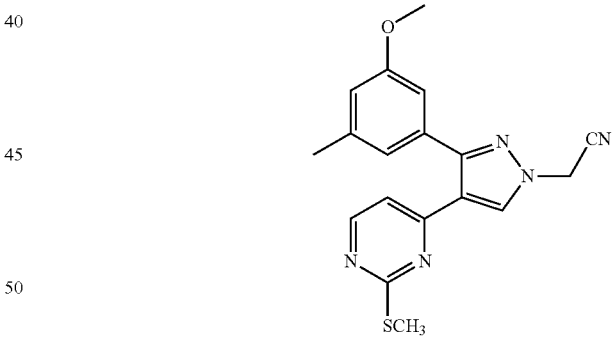

In a two-necked round-bottom flask, [3-(3-methoxy-5-methylphenyl)-4-(2-methylthiopyrimidine-4-yl]-1H-pyrazol (5 g, 16.0 mmol) was dissolved in dimethylformamide (65 mL) to which potassium carbonate (5.52 g, 40 mmol) and iodoacetonitrile (2.9 mL, 40 mmol) were added, and heated at 50° C. for 16 hours with stirring. After completion of the reaction, the reaction mixture was washed with brine and extracted with ethyl acetate. The organic layer was washed with brine and dried over anhydrous magnesium sulfate. The solvent was removed by vacuum distillation and the residue was purified through column chromatography to recover the title compound (2.1 g, 37.4%).

m.p. 117° C.; $^1$H NMR (400 MHz, CDCl$_3$) δ 2.36 (s, 3H), 2.54 (s, 3H), 3.78 (s, 3H), 5.15 (s, 2H), 6.79 (s, 1H), 6.80 (s,

1H), 6.82 (d, J=4.79 Hz, 1H), 6.92 (s, 1H), 8.26 (s, 1H), 8.30 (d, J=5.22 Hz, 1H); IR (KBr) 3429, 2926, 1571, 1460, 1324, 1157 cm$^{-1}$.

Example 15

Preparation of [4-(2-methanesulfonylpyrimidin-4-yl)-3-(3-methoxy-5-methylphenyl)-pyrazol-1-yl]acetonitrile

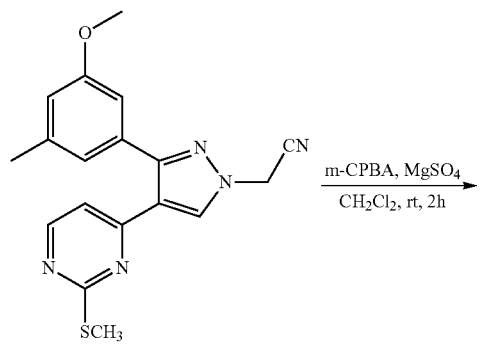

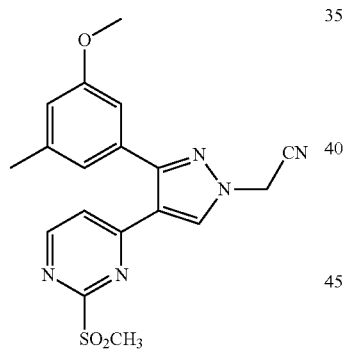

m-Chloroperbenzoic acid (4.71 g, 27.3 mmol) and anhydrous magnesium sulfate (6.57 g, 54.6 mmol) in dichloromethane (100 mL) were dissolved at room temperature for 1 hour with stirring. To this solution was added [3-(3-methoxy-5-methylphenyl)-4-(2-methylthio-pyrimidin-4-yl)pyrazol-1-yl]acetonitrile (1.6 g, 4.55 mmol) which was subjected to oxidation to sulfone by stirring for an additional two hours. After completion of the reaction, the precipitate was filtered off and washed with dichloromethane. The filtrate was washed with brine and dichloromethane, and the organic layer was separated, dried over anhydrous magnesium sulfate and concentrated through vacuum distillation. The residue was purified by column chromatography to give the title compound (1.23 g, 70.4%).

m.p. 238° C.; $^1$H NMR (300 MHz, CDCl$_3$) δ 2.30 (s, 3H), 3.26 (s, 3H), 3.73 (s, 3H), 5.10 (s, 2H), 6.73 (s, 1H), 6.77 (s, 1H), 6.82 (s, 1H), 7.23 (d, J=5.35 Hz, 1H), 8.38 (s, 1H), 8.56 (d, J=5.33 Hz, 1H); IR (Kbr) 3437, 2926, 1580, 1464, 1312, 1133 cm$^{-1}$.

Example 16

Preparation of [4-[2-(3-hydroxyazetindin-1-yl)-pyrimidin-4-yl]-3-(3-methoxy-5-methylphenyl)-pyrazol-1-yl]acetonitrile

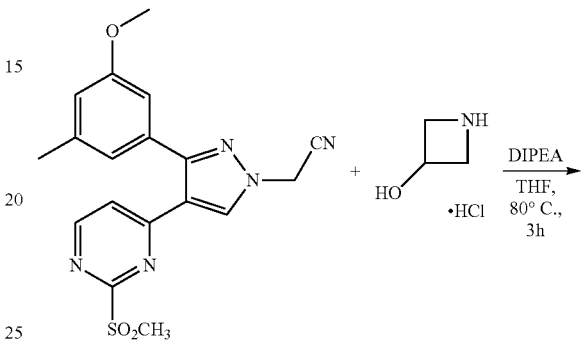

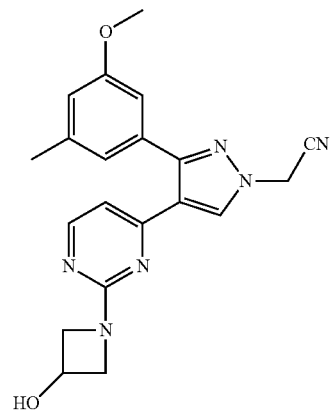

In a two-necked round-bottom flask, [4-(2-methanesulfonylpyrimidin-4-yl)-3-(3-methoxy-5-methylphenyl)pyrazol-1-yl]acetonitrile (340 mg, 0.89 mmol) and 3-hydroxyazetidine hydrochloride (486 mg, 4.44 mmol) were dissolved in anhydrous tetrahydrofuran (5 mL). To this solution was dropwise added N,N-diisopropyl ethyl amine (1.47 mL, 8.9 mmol) and refluxed for 3 hours. After completion of the nucleophilic substitution reaction, the reaction mixture was washed with water and extracted with dichloromethane. The organic layer was washed with a saturated ammonium chloride solution and brine, dried over anhydrous magnesium sulfate and concentrated through vacuum distillation. Purification by column chromatography gave the title compound (191.97 mg, 57.3%).

m.p. 186° C.; $^1$H NMR (300 MHz, CDCl$_3$) δ 2.27 (s, 3H), 2.33 (s, 1H), 3.70 (s, 3H), 3.92 (dd, J=3.81, 3.84 Hz, 2H), 4.29-4.34 (m, 2H), 4.70 (s, 1H), 5.06 (s, 2H), 6.35 (d, J=5.1

Hz, 1H), 6.71 (s, 1H), 6.77 (s, 1H), 6.87 (s, 1H), 8.06-8.07 (m, 2H); IR (KBr) 3428, 2924, 1574, 1463, 1167 cm⁻¹.

Example 17

Preparation of [4-[2-(3-hydroxyazetindin-1-yl)-pyrimidin-4-yl]-3-(3-hydroxy-5-methylphenyl)-pyrazol-1-yl]acetonitrile

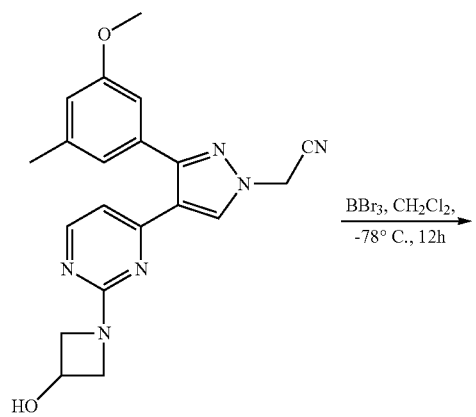

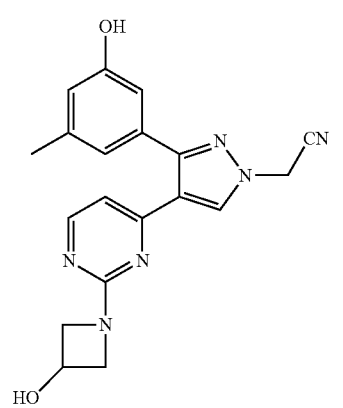

To anhydrous dichloromethane (3 mL) was added [4-[2-(3-hydroxyazetindin-1-yl)-pyrimidin-4-yl]-3-(3-methoxy-5-methylphenyl)-pyrazol-1-yl]acetonitrile (95 mg, 0.25 mmol). Under nitrogen atmosphere, boron trifluoride (97.26 μL, 1.00 mmol) was dropped at −78° C. to the solution, and stirred at room temperature for 12 hours. After completion of the demethylation, ice water and ethyl acetate were added to the reaction mixture. An aqueous dimethylamine solution (0.95 mL, 50% solution) was dropwise added until an alkaline condition was achieved, and then stirred for 1 hour. The reaction mixture was extracted with ethyl acetate and the organic layer was washed with brine, dried over anhydrous magnesium sulfate and concentrated through vacuum distillation. Column chromatography purified the title compound (22 mg, 22.4%).

m.p. 239° C.; ¹H NMR (300 MHz, DMSO-d₆) δ 2.23 (s, 3H), 3.73 (dd, J=4.27, 4.47 Hz, 2H), 4.14-4.19 (m, 2H), 4.50-4.44 (m, 1H), 5.56 (s, 2H), 6.47 (d, J=4.14 Hz, 1H), 6.60 (s, 1H), 6.71 (d, J=10.89 Hz, 2H), 8.18 (d, J=5.12 Hz, 1H), 8.38 (s, 1H); IR (KBr) 3426, 3225, 2966, 1581, 1464, 1173 cm⁻¹.

Example 18

Preparation of [4-[2-(3(S)-hydroxypyrrolidin-1-yl)-pyrimidin-4-yl]-3-(3-methoxy-5-methylphenyl)-pyrazol-1-yl]acetonitrile

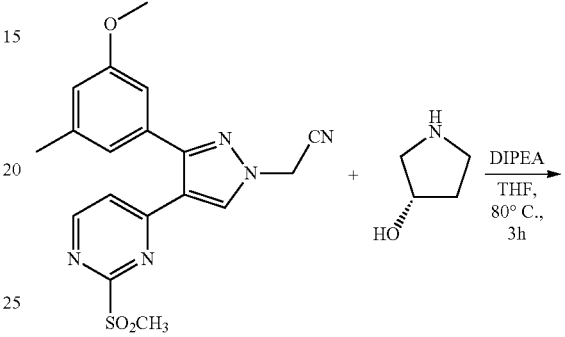

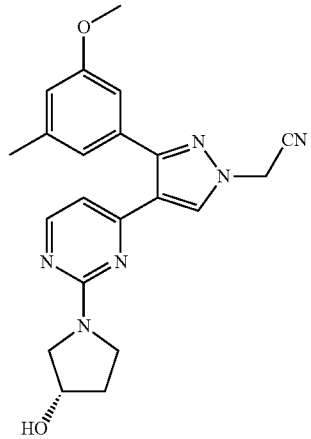

In a two-necked round-bottom flask, [4-(2-methanesulfonylpyrimidin-4-yl)-3-(3-methoxy-5-methylphenyl)pyrazol-1-yl]acetonitrile (0.77 g, 2 mmol) and (S)-3-hydroxypyrrolidine (0.81 mL, 9.99 mmol) were dissolved in anhydrous tetrahydrofuran (5 mL). To this solution was drop wise added N,N-diisopropyl ethyl amine (3.47 mL, 19.97 mmol) and refluxed for 3 hours. After completion of the nucleophilic substitution reaction, the solvent was removed by vacuum distillation. The reaction mixture was washed with water and extracted with dichloromethane. The organic layer was washed with a saturated ammonium chloride solution and brine, dried over anhydrous magnesium sulfate and concentrated through vacuum distillation. Column chromatography purified the title compound (0.5 g, 64%).

m.p. 177° C.; ¹H NMR (400 MHz, CDCl₃) δ 2.09-2.16 (m, 2H), 2.35 (s, 3H), 3.49 (d, J=7.1 Hz, 1H), 3.68-3.73 (m, 4H), 3.78 (s, 3H), 4.61 (s, 1H), 5.14 (s, 2H), 6.40 (d, J=4.54 Hz,

1H), 6.78 (s, 1H), 6.83 (s, 1H), 6.88 (s, 1H), 8.11-8.15 (m, 2H); IR (KBr) 3417, 2936, 1573, 1165 cm$^{-1}$.

Example 19

Preparation of [4-[2-(3(S)-hydroxypyrrolidin-1-yl)-pyrimidin-4-yl]-3-(3-hydroxy-5-methylphenyl)-pyrazol-1-yl]acetonitrile

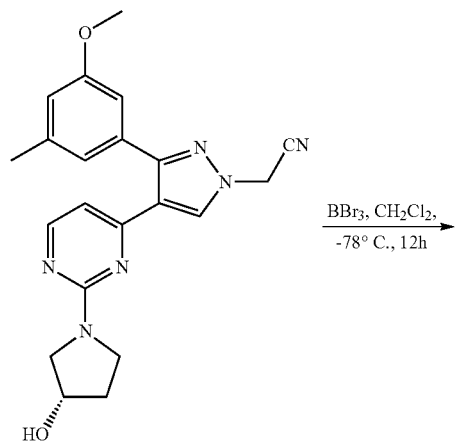

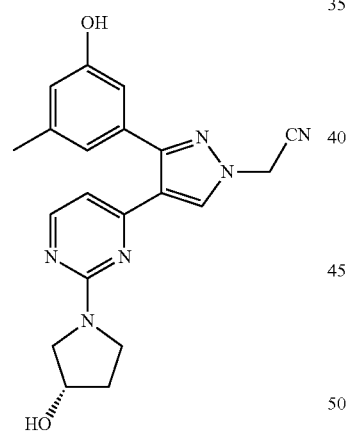

To anhydrous dichloromethane (5 mL) was added [4-[2-(3 (S)-hydroxypyrrolidin-1-yl)-pyrimidin-4-yl]-3-(3-methoxy-5-methylphenyl)-pyrazol-1-yl]acetonitrile (0.5 g, 1.28 mmol). Under nitrogen atmosphere, boron tribromide (484 μL, 5.12 mmol) was dropped at −78° C. to the solution, and stirred at room temperature for 12 hours. After completion of the demethylation, ice water and ethyl acetate were added to the reaction mixture. An aqueous dimethylamine solution (4.82 mL, 50% solution) was dropwise added until an alkaline condition was achieved, and then stirred for 1 hour. The reaction mixture was extracted with ethyl acetate and the organic layer was washed with brine, dried over anhydrous magnesium sulfate and concentrated through vacuum distillation. Column chromatography purified the title compound (158.1 mg, 32.8%).

m.p. 234° C.; $^1$H NMR (400 MHz, MeOD) δ 2.08-2.01 (m, 2H), 2.23 (s, 3H), 3.54-3.62 (m, 4H), 4.48 (s, 1H), 5.40 (s, 2H), 6.48 (d, J=5.12 Hz, 1H), 6.68 (s, 1H), 6.74 (s, 1H), 6.82 (s, 1H), 8.10 (d, J=5.25 Hz, 1H), 8.34 (s, 1H); IR (KBr) 3392, 2940, 1577, 1475, 1164 cm$^{-1}$.

Example 20

Preparation of 2-(2-chloropyridin-4-yl)-1-(3-methoxy-5-methylphenyl)ethanone

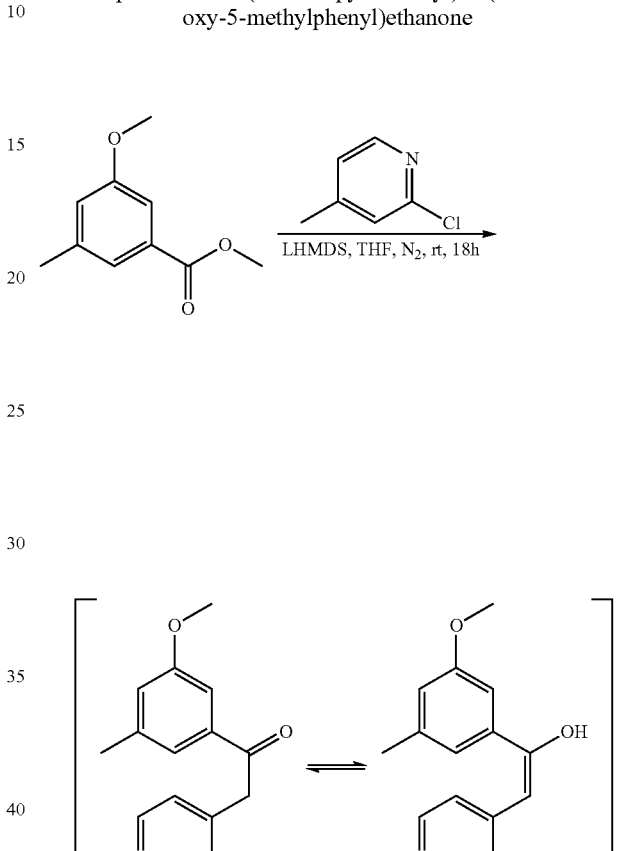

To a solution of methyl 3-methoxy-5-methylbenzoate (9.0 g, 50 mmol) and 2-chloro-4-methylpyridine (7.0 g, 55 mmol) in tetrahydrofuran (90 mL) was dropwise added lithium hexamethyldisilazide (75 mL, 75 mmol, 1M In THF) at 0° C. under a nitrogen atmosphere, and stirred at room temperature for 18 hours. After completion of the nucleophilic attack reaction, the reaction mixture was neutralized with a saturated ammonium chloride solution (150 mL) and extracted with ethyl acetate (300 mL×2). The organic layer was washed with brine, dried over anhydrous magnesium sulfate, and concentrated by vacuum distillation, and the concentrate (9.92 g, 72%) was used in the next reaction without further purification.

1H NMR (CDCl$_3$) δ 2.41 (s, 3H), 3.84 (s, 3H), 4.26 (s, 2H), 6.98 (s, 1H), 7.13 (d, J=4.5 Hz, 1H), 7.25 (s, 1H), 7.30 (s, 1H), 7.38 (s, 1H), 8.34 (d, J=4.6 Hz, 1H); $^{13}$C NMR (CDCl$_3$) δ 21.36, 21.52, 44.14, 55.41, 55.47, 110.12, 120.79, 121.82, 123.82, 125.45, 137.23, 140.16, 146.86, 149.57, 151.69, 159.97, 195.14.

Example 21

Preparation of 4-(2-chloropyridin-4-yl)-3-(3-methoxy-5-methylphenyl)-1H-pyrazol

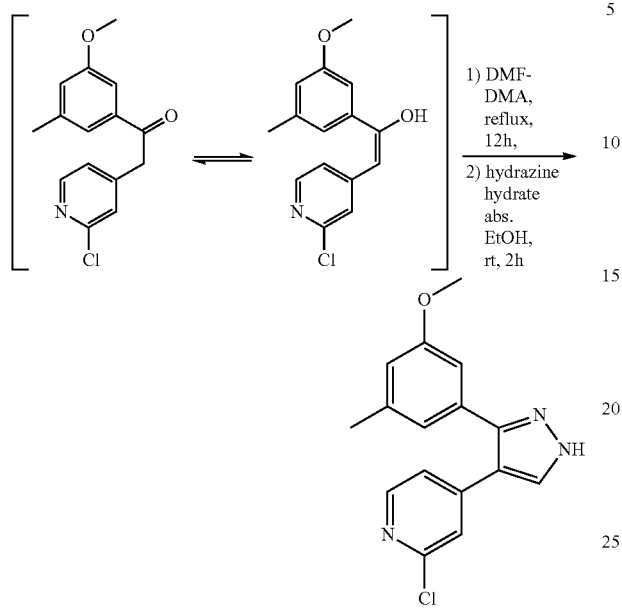

The keto-enol compound (9.1 g, 33 mmol) was refluxed for 12 hours with N,N-dimethylformamide dimethylacetal (30 mL, 255 mmol). Excess N,N-dimethylformamide dimethylacetal was removed by vacuum distillation, and the reaction mixture was dissolved in anhydrous ethanol (150 mL). To this solution was dropwise added hydrazine hydrate (3.3 g, 66 mmol), and stirred at room temperature for 2 hours. After completion of the cyclization, the solvent was removed by vacuum distillation. The concentrate was crystallized in ethyl acetate/hexane to afford the title compound as a red solid (8.0 g, 81%).

$^1$H NMR (CDCl$_3$) δ 2.33 (s, 3H), 3.75 (s, 3H), 6.78 (s, 1H), 6.80 (s, 1H), 6.85 (s, 1H), 7.13 (dd, J=1.1, 4.2 Hz, 1H), 7.32 (s, 1H), 7.76 (s, 1H), 8.25 (d, J=5.3 Hz, 1H); $^{13}$C NMR (CDCl$_3$) δ 21.54, 55.30, 111.11, 115.63, 115.89, 121.03, 121.49, 122.27, 140.41, 144.28, 149.61, 151.84, 159.91.

Example 22

Preparation of [4-(2-chloropyridin-4-yl)-3-(3-methoxy-5-methylphenyl)-pyrazol-1-yl]acetonitrile and [4-(2-chloropyridin-4-yl)-5-(3-methoxy-5-methylphenyl)-pyrazol-1-yl]acetonitrile

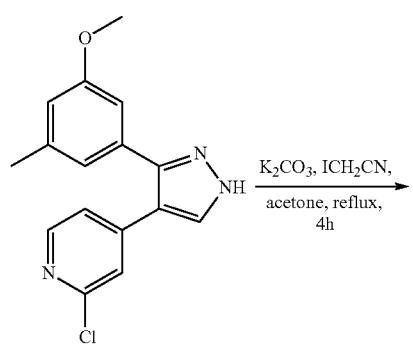

K$_2$CO$_3$, ICH$_2$CN,
acetone, reflux,
4h

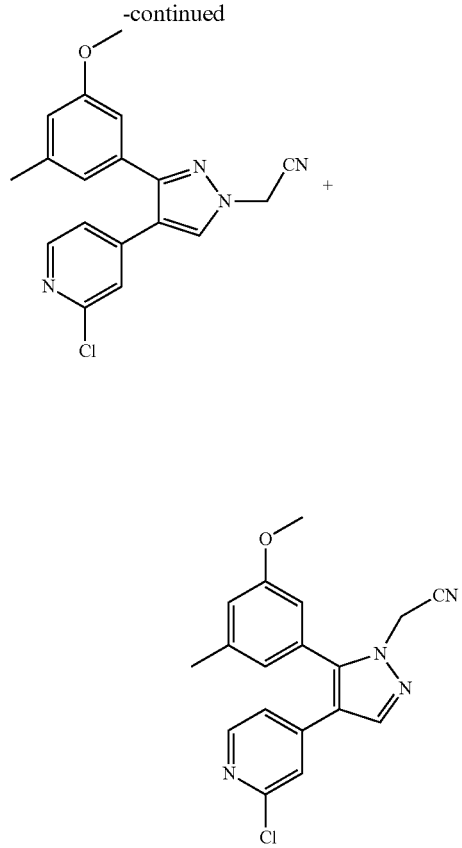

The compound obtained in Example 21 (4.6 g, 15.35 mmol) and potassium carbonate (10.6 g, 76.73 mmol) were added to acetone (100 mL) and refluxed for 2 hours by heating. To this reaction mixture was dropwise added iodoacetonitrile (1.34 mL, 18.42 mmol), and refluxed over 2 hours. The acetone was removed by vacuum distillation, and to the residue were added water (200 mL) and ethyl acetate (200 mL). The organic layer was dried over anhydrous magnesium sulfate and distillated in a vacuum. The concentrate was subjected to column chromatography (silica gel, ethyl acetate-hexane 2:3 v/v) to afford a mixture of 2:1 of [4-(2-chloropyridin-4-yl)-3-(3-methoxy-5-methylphenyl)-1H-pyrazol-1-yl]acetonitrile and [4-(2-chloropyridin-4-yl)-5-(3-methoxy-5-methylphenyl)-1H-pyrazol-1-yl]acetonitrile as yellow oil. These two regioisomers (4.78 g, 92%) were used in the next reaction step without separation.

[4-(2-Chloropyridin-4-yl)-3-(3-methoxy-5-methylphenyl)-1H-pyrazol-1-yl]acetonitrile: $^1$H NMR (CDCl$_3$) δ 2.29 (s, 3H), 3.71 (s, 3H), 5.19 (s, 2H), 6.73 (s, 1H), 6.75 (s, 1H), 6.85 (s, 1H), 7.06 (d, J=4.4 Hz, 1H), 7.26 (s, 1H), 7.79 (s, 1H), 8.24 (d, J=4.8 Hz, 1H); $^{13}$C NMR (CDCl$_3$) δ 21.53, 39.97, 55.29, 110.91, 111.12, 113.65, 115.67, 118.75, 121.59, 121.65, 122.78, 130.58, 132.37, 140.16, 143.28, 149.68, 151.45, 151.79, 159.71, 162.33.

[4-(2-Chloropyridin-4-yl)-5-(3-methoxy-5-methylphenyl)-1H-pyrazol-1-yl]acetonitrile: $^1$H NMR (CDCl$_3$) δ 2.39 (s, 3H), 3.83 (s, 3H), 4.94 (s, 2H), 6.63 (s, 1H), 6.74 (s, 1H), 6.92-6.96 (m, 2H), 7.19 (s, 1H), 7.93 (s, 1H), 8.17 (d, J=5.2 Hz, 1H); $^{13}$C NMR (CDCl$_3$) δ 21.56, 37.78, 55.48, 112.15, 113.91, 117.08, 118.16, 119.88, 121.36, 122.48, 128.46, 139.57, 141.60, 142.19, 142.85, 149.78, 151.95, 160.48.

General Synthesis Route

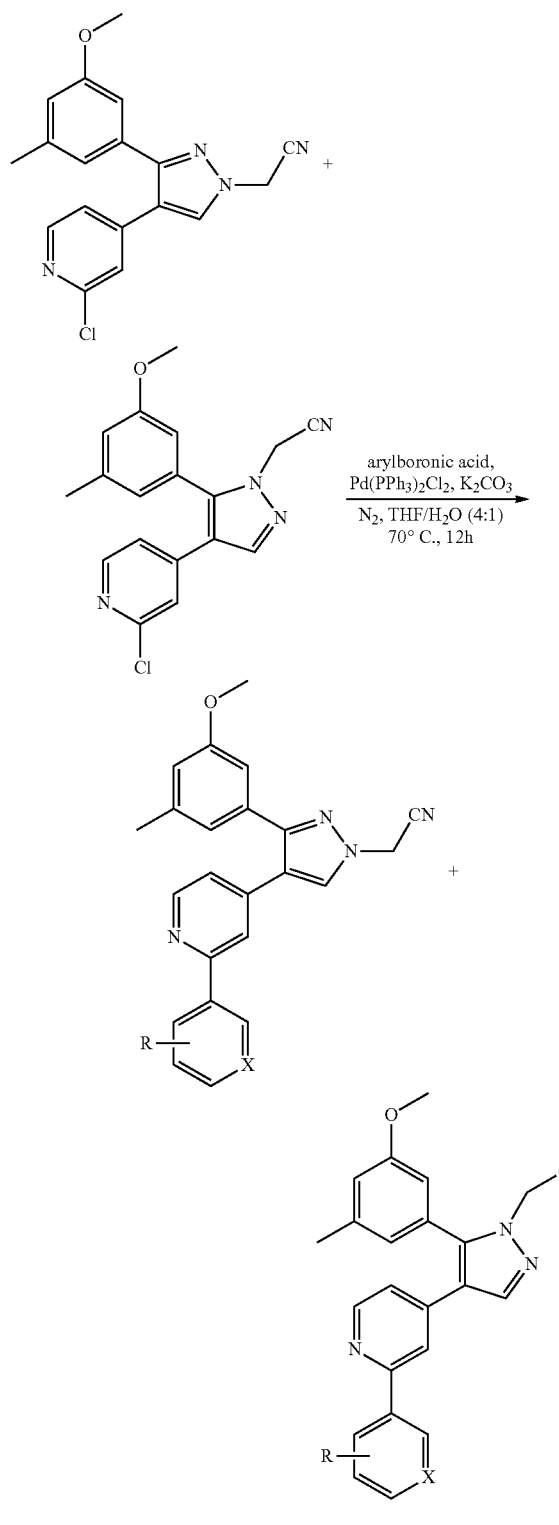

To a solvent mixture of THF and water (4:1, 10 mL) were added the mixture prepared in Example 22 (300 mg, 0.89 mmol), an appropriate arylboronic acid (0.974 mmol), dichlorobis(triphenylphosphine)palladium (II) (31 mg, 0.044 mmol) and potassium carbonate (130 mg, 0.89 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Example 23

Preparation of [3-(3-methoxy-5-methylphenyl)-4-(2-phenylpyridin-4-yl)-pyrazol-1-yl]acetonitrile

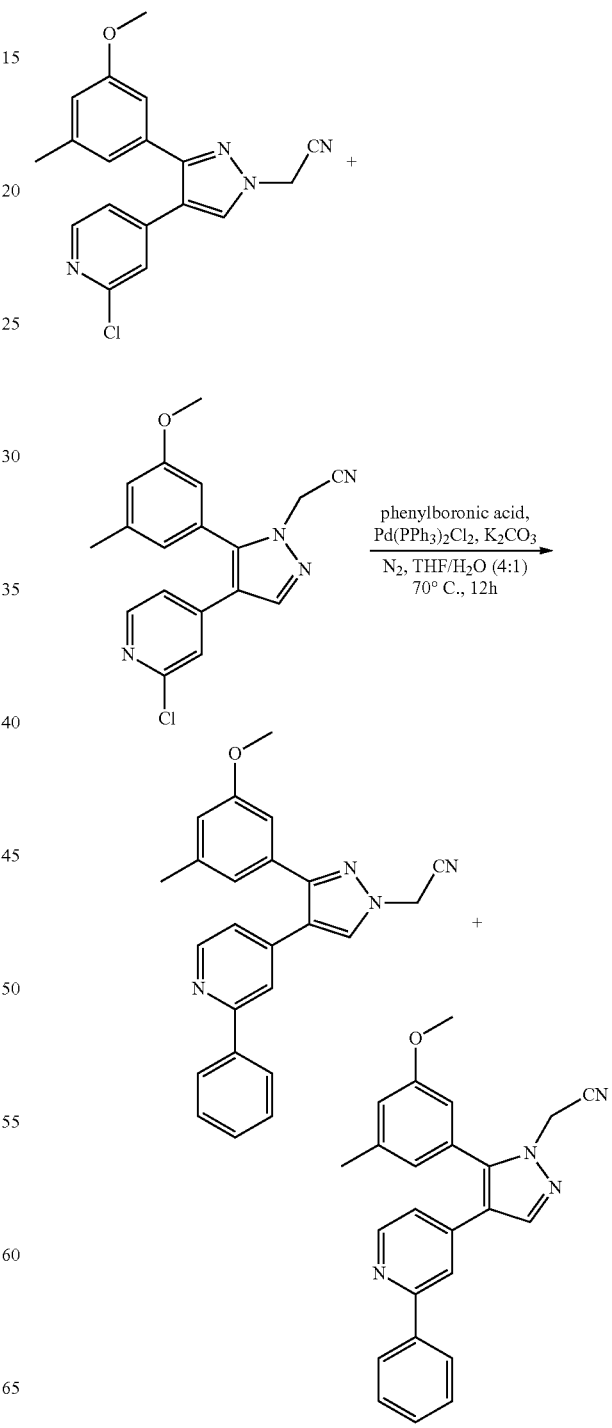

To a solvent mixture of THF and water (4:1, 10 mL) were added the mixture prepared in Example 22 (300 mg, 0.89 mmol), phenylboronic acid (0.12 g, 0.974 mmol), dichlorobis (triphenylphosphine)palladium (II) (31 mg, 0.044 mmol) and potassium carbonate (130 mg, 0.89 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:3, v/v): (166 mg, 74%); m.p. 55-56° C.; $^1$H NMR (CDCl$_3$) δ 2.32 (s, 3H), 3.71 (s, 3H), 5.14 (s, 2H), 6.79 (s, 1H), 6.84 (s, 1H), 6.96 (s, 1H), 7.13 (d, J=4.9 Hz, 1H), 7.41-7.48 (m, 3H), 7.65 (s, 1H), 7.79 (s, 1H), 7.88 (d, J=6.9 Hz, 2H), 8.61 (d, J=5.1 Hz, 1H); $^{13}$C NMR (CDCl$_3$) δ21.51, 39.86, 55.25, 110.90, 113.61, 115.61, 119.78, 120.42, 121.24, 121.76, 126.89, 128.78, 129.11, 130.05, 132.90, 139.19, 139.98, 140.77, 149.89, 151.46, 157.75, 159.75.

Example 24

Preparation of [3-(3-methoxy-5-methylphenyl)-4-(2-(pyridin-3-yl)pyridin-4-yl)-pyrazol-1-yl]acetonitrile

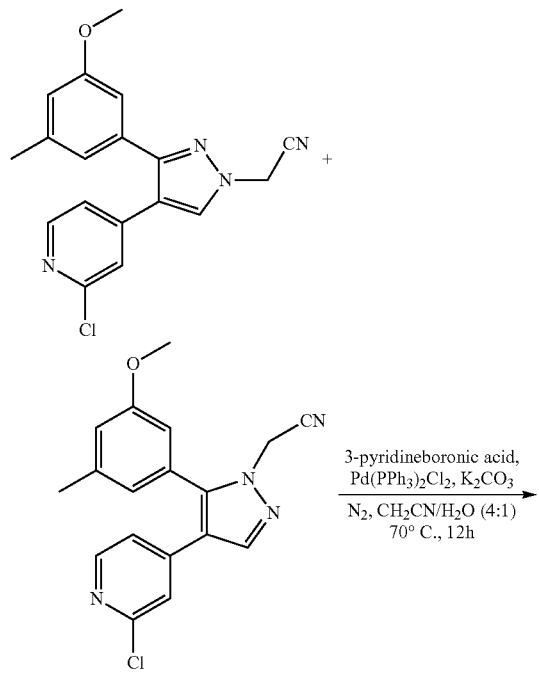

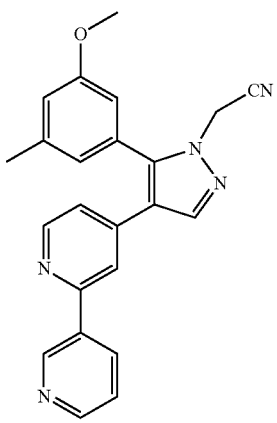

To a solvent mixture of acetonitrile and water (4:1, 10 mL) were added the mixture prepared in Example 22 (100 mg, 0.30 mmol), 3-pyridineboronic acid (40.5 mg, 0.33 mmol), dichlorobis(triphenylphosphine)palladium (II) (10 mg, 0.015 mmol) and potassium carbonate (41 mg, 0.295 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 2:1, v/v): (180 mg, 80%); m.p. 72-73° C.; $^1$H NMR (CDCl$_3$) δ 2.28 (s, 3H), 3.69 (s, 3H), 5.17 (s, 2H), 6.76 (s, 1H), 6.80 (s, 1H), 6.91 (s, 1H), 7.17 (dd, J=1.2, 3.9 Hz, 1H), 7.35 (dd, J=2.7, 4.8 Hz, 1H), 7.62 (s, 1H), 7.84 (s, 1H), 8.18 (d, J=8.1 Hz, 1H), 8.56-8.60 (m, 2H), 9.00 (d, J=1.3 Hz, 1H) $^{13}$C NMR (CDCl$_3$) δ 21.50, 39.91, 55.25, 111.12, 113.66, 115.49, 119.72, 119.98, 121.72, 121.80, 123.61, 130.20, 132.77, 134.33, 134.72, 140.03, 141.06, 148.11, 149.94, 150.25, 151.48, 155.00, 159.75.

Example 25

Preparation of [3-(3-methoxy-5-methylphenyl)-4-(2-(2-acetylphenyl)pyridin-4-yl)-pyrazol-1-yl]acetonitrile

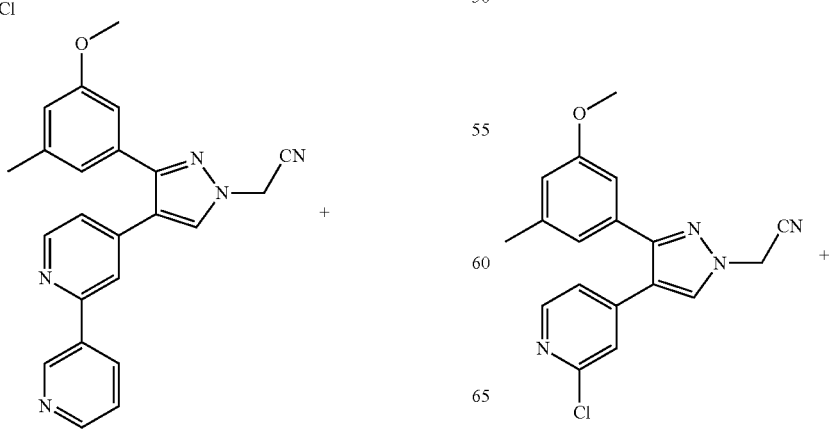

-continued

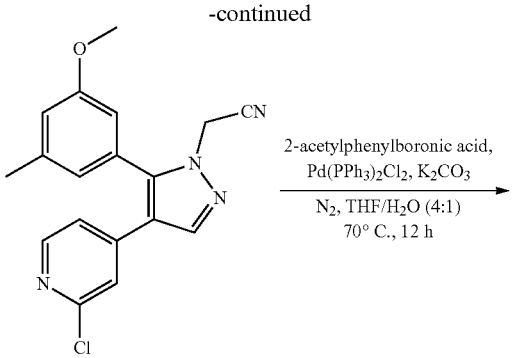

2-acetylphenylboronic acid,
Pd(PPh₃)₂Cl₂, K₂CO₃
─────────────────→
N₂, THF/H₂O (4:1)
70° C., 12 h

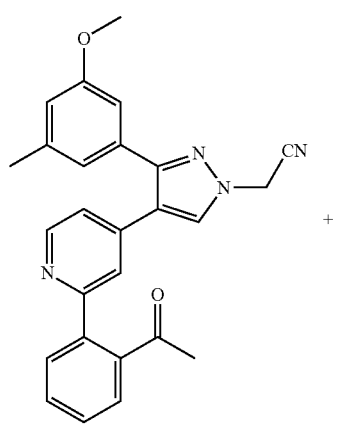

+

+

To a solvent mixture of THF and water (4:1, 10 mL) were added the mixture prepared in Example 22 (320 mg, 0.95 mmol), 2-acetylphenylboronic acid (0.19 g, 1.13 mmol), dichlorobis(triphenylphosphine)palladium(II) (33 mg, 0.05 mmol) and potassium carbonate (131 mg, 0.95 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (152 mg, 61%); m.p. 63-64° C.; ¹H NMR (CDCl₃) δ 2.19 (s, 3H), 2.28 (s, 3H), 3.70 (s, 3H), 5.16 (s, 2H), 6.75 (s, 1H), 6.79 (s, 1H), 6.90 (s, 1H), 7.11 (d, J=4.1 Hz, 1H), 7.40-7.55 (m, 4H), 7.65 (dd, J=4.8, 7.2 Hz, 1H), 7.81 (s, 1H), 8.48 (d, J=5.1 Hz, 1H).

Example 26

Preparation of [3-(3-methoxy-5-methylphenyl)-4-(2-(3-acetylphenyl)pyridin-4-yl)-pyrazol-1-yl]acetonitrile

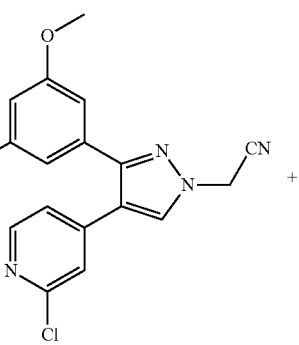

+

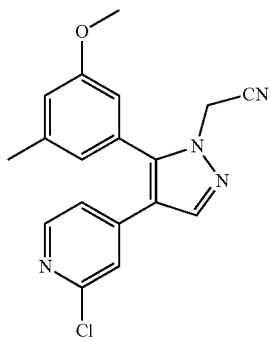

3-acetylphenylboronic acid,
Pd(PPh₃)₂Cl₂, K₂CO₃
─────────────────→
N₂, THF/H₂O (4:1)
70° C., 12 h

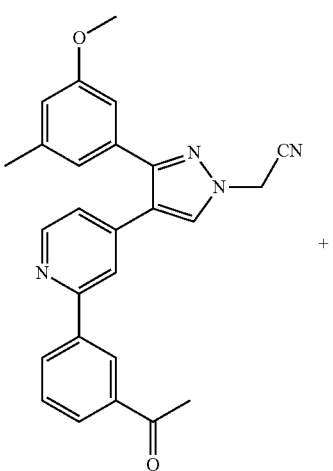

+

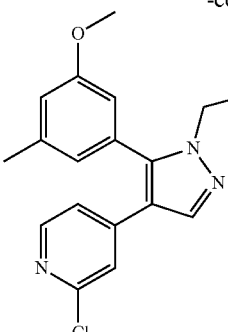

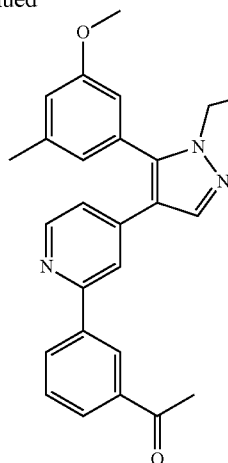

To a solvent mixture of THF and water (4:1, 10 mL) were added the mixture prepared in Example 22 (320 mg, 0.95 mmol), 3-acetylphenyl boronic acid (0.19 g, 1.13 mmol), dichlorobis(triphenylphosphine)palladium (II) (33 mg, 0.05 mmol) and potassium carbonate (131 mg, 0.95 mmol), and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (197 mg, 79%); m.p. 73-74° C.; $^1$H NMR (CDCl$_3$) δ 2.27 (s, 3H), 2.60 (s, 3H), 3.67 (s, 3H), 5.19 (s, 2H), 6.76 (s, 1H), 6.80 (s, 1H), 6.91 (s, 1H), 7.13 (s, 1H), 7.49 (bs, 1H), 7.64 (s, 1H), 7.85 (s, 1H), 7.95 (d, J=5.4 Hz, 1H), 8.04 (d, J=5.7 Hz, 1H), 8.39 (s, 1H), 8.56 (s, 1H); $^{13}$C NMR (CDCl$_3$) δ 21.51, 26.78, 39.89, 55.23, 111.03, 113.93, 115.51, 119.76, 119.90, 121.63, 121.77, 126.71, 128.60, 128.76, 129.11, 130.54, 131.45, 132.06, 132.92, 137.52, 139.61, 140.00, 141.09, 149.91, 151.38, 156.47, 159.69, 198.16.

Example 27

Preparation of [3-(3-methoxy-5-methylphenyl)-4-(2-(4-acetylphenyl)pyridin-4-yl)-pyrazol-1-yl]acetonitrile

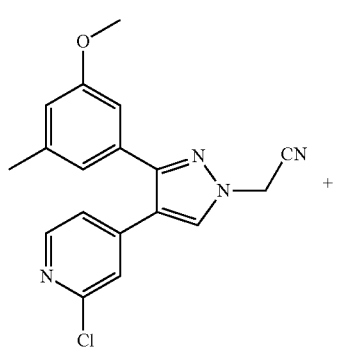

+

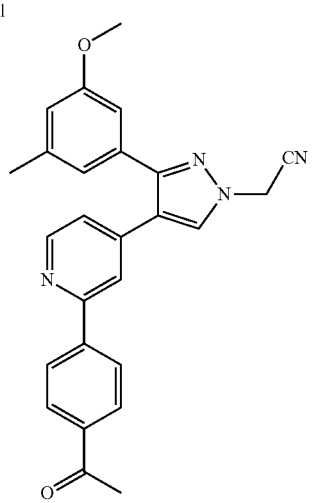

+

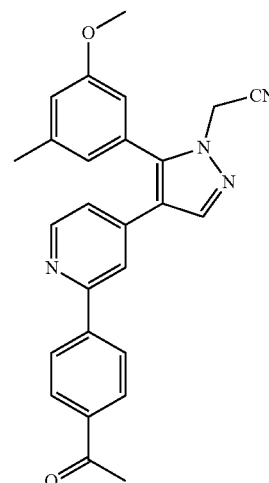

To a solvent mixture of THF and water (4:1, 10 mL) were added the mixture prepared in Example 22 (320 mg, 0.95 mmol), 4-acetylphenyl boronic acid (0.19 g, 1.13 mmol), dichlorobis(triphenylphosphine)palladium (II) (33 mg, 0.05 mmol) and potassium carbonate (131 mg, 0.95 mmol), and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (170 mg, 68%); m.p. 99-100° C.; $^1$H NMR (CDCl$_3$) δ 2.32 (s, 3H), 2.65 (s, 3H), 3.72 (s, 3H), 5.20 (s, 2H), 6.79 (s, 1H), 6.82 (s, 1H), 6.94 (s, 1H), 7.20 (d, J=5.1 Hz, 1H), 7.69 (s, 1H), 7.88 (s, 1H), 7.95 (d, J=8.4 Hz, 2H), 8.02 (d, J=8.4 Hz, 2H), 8.63 (d, J=5.1 Hz, 1H); $^{13}$C NMR (CDCl$_3$) δ 21.54, 26.80, 39.95, 55.27, 110.97, 113.53, 115.58, 120.20, 121.74, 121.88, 127.00, 128.82, 130.02, 132.77, 137.19, 140.06, 140.95, 143.39, 150.15, 151.54, 156.35, 159.77, 197.91.

Example 28

Preparation of [3-(3-methoxy-5-methylphenyl)-4-(2-(2-acetamidophenyl)pyridin-4-yl)-pyrazol-1-yl]acetonitrile

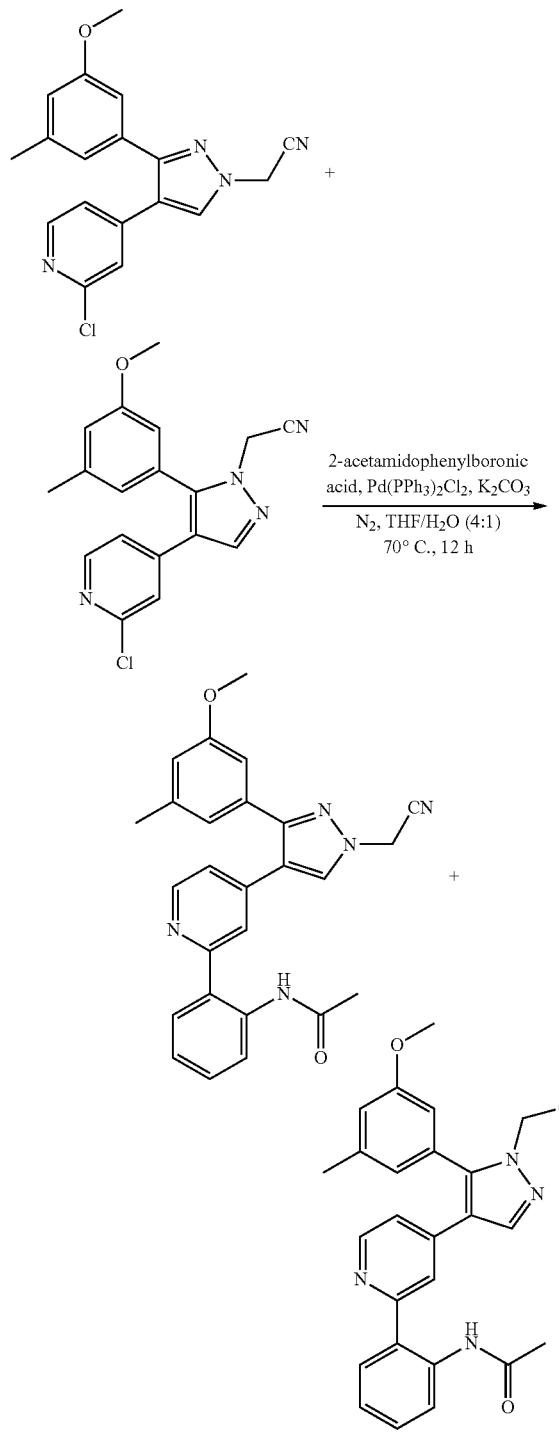

To a solvent mixture of THF and water (4:1, 10 mL) were added the mixture prepared in Example 22 (310 mg, 0.92 mmol), 2-acetamidophenyl boronic acid (0.20 g, 1.10 mmol), dichlorobis(triphenylphosphine)palladium (II) (33 mg, 0.05 mmol) and potassium carbonate (130 mg, 0.92 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 2:1, v/v): (201 mg, 78%); m.p. 80-81° C.; $^1$H NMR (CDCl$_3$) δ 2.18 (s, 3H), 2.33 (s, 3H), 3.74 (s, 3H), 5.19 (s, 2H), 6.80 (s, 1H), 6.82 (s, 1H), 6.94 (s, 1H), 7.07 (t, J=7.4 Hz, 1H), 7.16 (d, J=4.5 Hz, 1H), 7.35-7.40 (m, 2H), 7.47 (d, J=5.4 Hz, 1H), 7.87 (s, 1H), 8.48-8.53 (m, 2H), 12.10 (s, 1H).

Example 29

Preparation of [3-(3-methoxy-5-methylphenyl)-4-(2-(3-acetamidophenyl)pyridin-4-yl)-pyrazol-1-yl]acetonitrile

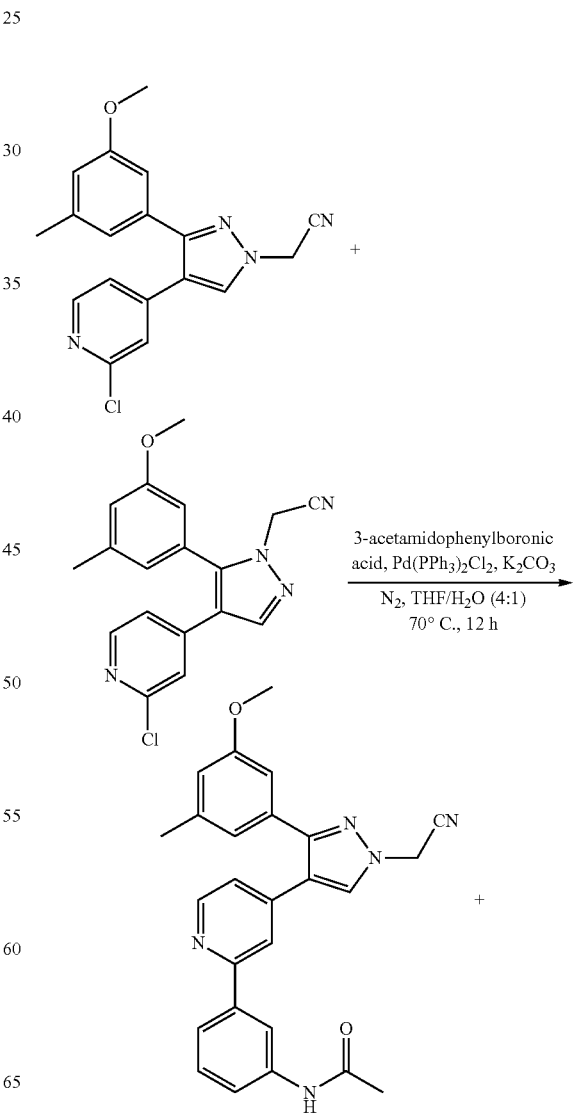

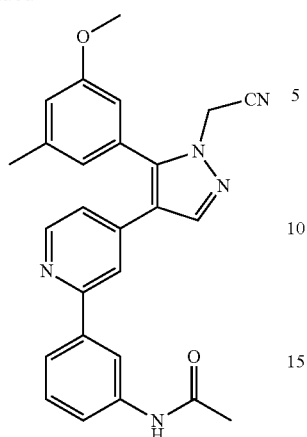

To a solvent mixture of THF and water (4:1, 10 mL) were added the mixture prepared in Example 22 (320 mg, 0.95 mmol), 3-acetamidophenyl boronic acid (0.20 g, 1.13 mmol), dichlorobis(triphenylphosphine)palladium (II) (34 mg, 0.05 mmol) and potassium carbonate (131 mg, 0.95 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 2:1, v/v): (194 mg, 75%); m.p. 103-105° C.; $^1$H NMR (CDCl$_3$) δ 2.13 (s, 3H), 2.47 (s, 3H), 3.68 (s, 3H), 5.14 (s, 2H), 6.74 (s, 1H), 6.78 (s, 1H), 6.89 (s, 1H), 7.03 (d, J=4.7 Hz, 1H), 7.28-7.34 (m, 1H), 7.51-7.57 (m, 2H), 7.62 (d, J=7.8 Hz, 1H), 7.71 (s, 1H), 8.09 (s, 1H), 8.27 (s, 1H), 8.47 (d, J=4.8 Hz, 1H); $^{13}$C NMR (CDCl$_3$) δ 21.48, 24.44, 39.80, 55.27, 110.92, 113.82, 115.56, 118.46, 119.72, 120.02, 120.70, 121.51, 121.82, 122.60, 129.42, 130.37, 132.93, 138.68, 139.83, 139.99, 140.96, 149.59, 151.33, 157.11, 159.65, 169.06.

Example 30

Preparation of [3-(3-methoxy-5-methylphenyl)-4-(2-(4-cyanophenyl)pyridin-4-yl)-pyrazol-1-yl]acetonitrile

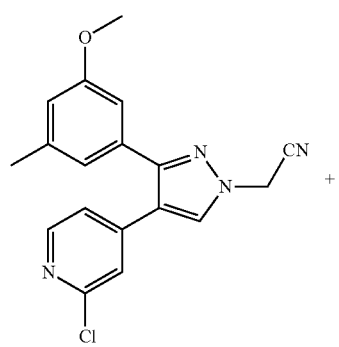

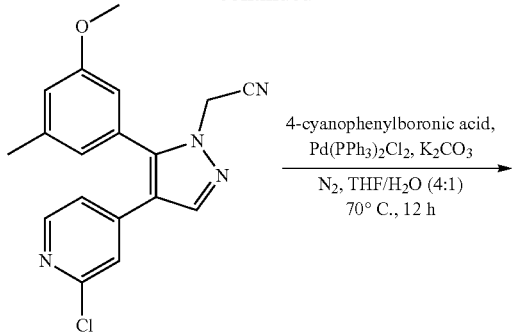

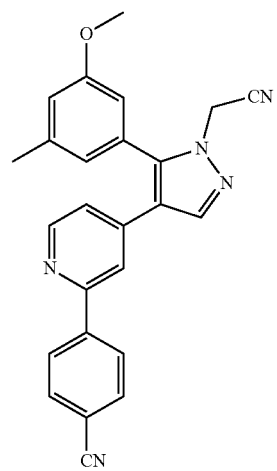

To a solvent mixture of THF and water (4:1, 10 mL) were added the mixture prepared in Example 22 (320 mg, 0.95 mmol), 4-cyanophenylboronic acid (0.17 g, 1.13 mmol), dichlorobis(triphenylphosphine)palladium (II) (34 mg, 0.05 mmol) and potassium carbonate (131 mg, 0.95 mmol), and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (196 mg, 82%); m.p. 83-84° C.; $^1$H NMR (CDCl$_3$) δ 2.31 (s, 3H), 3.71 (s, 3H), 5.19 (s, 2H), 6.79 (s, 1H), 6.82 (s, 1H), 6.93 (s, 1H), 7.22 (d, J=4.6 Hz, 1H), 7.66 (s, 1H), 7.71 (d, J=8.3 Hz, 2H), 7.87 (s, 1H), 7.97 (d, J=8.3 Hz, 2H), 8.63 (d, J=5.1 Hz, 1H); $^{13}$C NMR (CDCl$_3$) δ 21.50, 39.96, 55.27, 111.11, 112.47, 113.57, 115.51, 118.78, 119.97, 120.10, 121.75, 122.22, 127.38, 130.09, 132.53, 132.80, 140.06, 141.17, 143.30, 150.26, 151.51, 155.44, 159.81.

Example 31

Preparation of [3-(3-methoxy-5-methylphenyl)-4-(2-(4-dimethylaminophenyl)pyridin-4-yl)-pyrazol-1-yl] acetonitrile

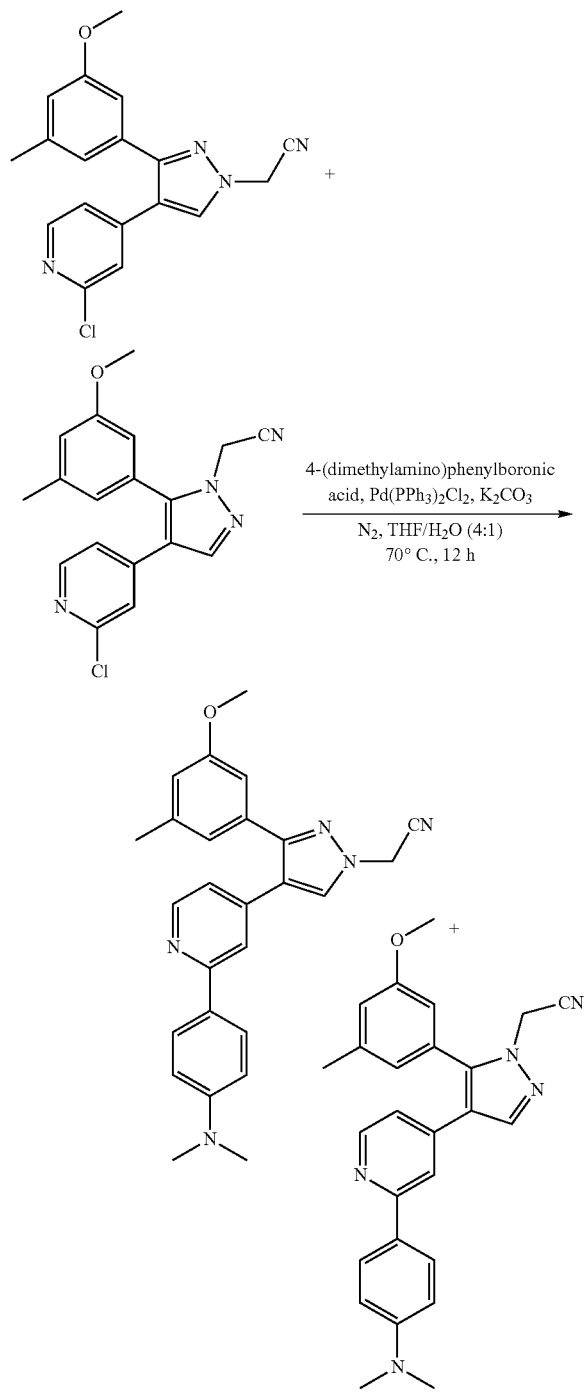

To a solvent mixture of THF and water (4:1, 10 mL) were added the mixture prepared in Example 22 (320 mg, 0.95 mmol), 4-(dimethylamino)phenylboronic acid (0.19 g, 1.13 mmol), dichlorobis(triphenylphosphine)palladium (II) (34 mg, 0.05 mmol) and potassium carbonate (131 mg, 0.95 mmol), and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (197 mg, 79%); m.p. 98-99° C.; $^1$H NMR (CDCl$_3$) δ 2.31 (s, 3H), 3.01 (s, 6H), 3.70 (s, 3H), 5.10 (s, 2H), 6.75-6.78 (m, 3H), 6.84 (s, 1H), 6.97-7.00 (m, 2H), 7.56 (s, 1H), 7.72 (s, 1H), 7.80 (d, J=8.8 Hz, 2H), 8.52 (d, J=5.0 Hz, 1H); $^{13}$C NMR (CDCl$_3$) δ 21.53, 39.79, 40.34, 55.25, 110.68, 112.16, 113.70, 115.67, 118.33, 119.88, 120.69, 121.74, 126.77, 127.72, 130.10, 132.99, 139.89, 140.46, 149.55, 151.13, 151.35, 157.78, 159.68.

Example 32

Preparation of [3-(3-methoxy-5-methylphenyl)-4-(2-(4-phenoxyphenyl)pyridin-4-yl)-pyrazol-1-yl]acetonitrile

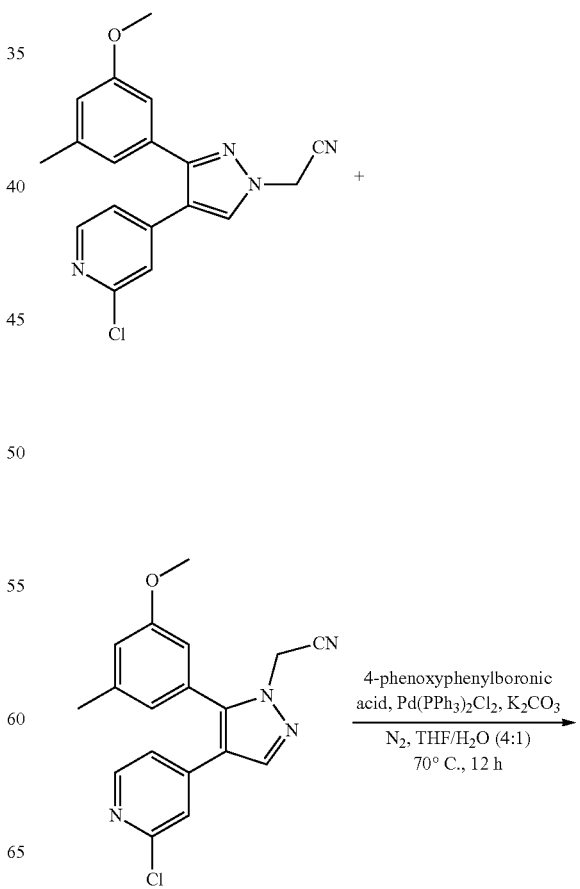

129.81, 129.94, 130.86, 132.40, 132.82, 140.09, 142.48, 148.36, 151.65, 156.10, 156.43, 158.98, 159.81.

Example 33

Preparation of [5-(3-methoxy-5-methylphenyl)-4-(2-phenyl)pyridin-4-yl)-pyrazol-1-yl]acetonitrile

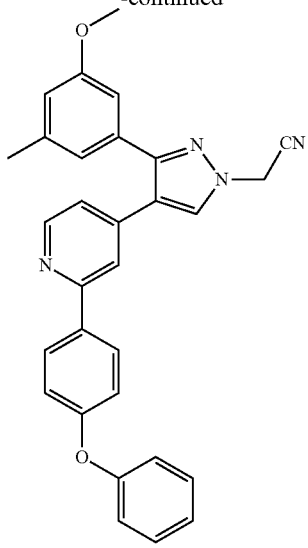

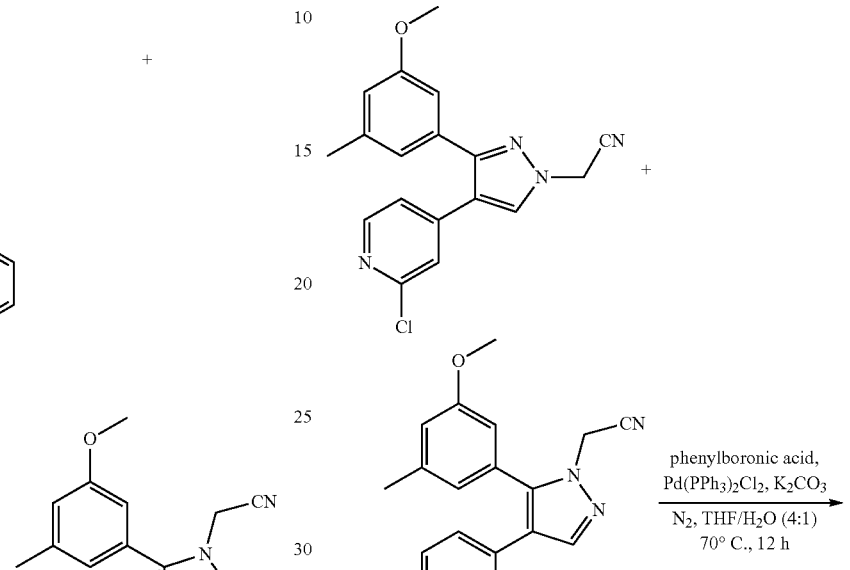

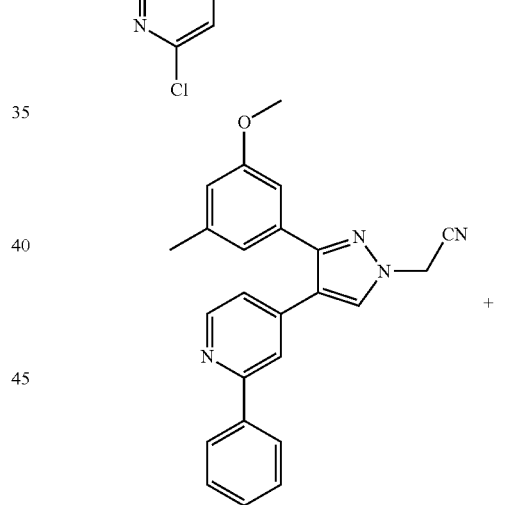

To a solvent mixture of THF and water (4:1, 10 mL) were added the mixture prepared in Example 22 (320 mg, 0.95 mmol), 4-phenoxyphenyl boronic acid (0.24 g, 1.13 mmol), dichlorobis(triphenylphosphine)palladium (II) (34 mg, 0.05 mmol) and potassium carbonate (131 mg, 0.95 mmol), and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:3, v/v): (201 mg, 72%); m.p. 80-81° C.; $^1$H NMR (CDCl$_3$) δ 2.31 (s, 3H), 3.72 (s, 3H), 5.18 (s, 2H), 6.79 (s, 1H), 6.83 (s, 1H), 6.94 (s, 1H), 7.04 (d, 8.0 Hz, 4H), 7.13-7.22 (m, 2H), 7.37 (t, J=73 Hz, 2H), 7.64 (s, 1H), 7.79 (d, J=8.3 Hz, 2H), 7.94 (s, 1H), 8.57 (d, J=5.0 Hz, 1H); $^{13}$C NMR (CDCl$_3$) δ 21.53, 39.89, 55.28, 111.05, 113.70, 115.65, 118.72, 119.42, 119.67, 119.74, 121.03, 121.80, 123.92, 128.57,

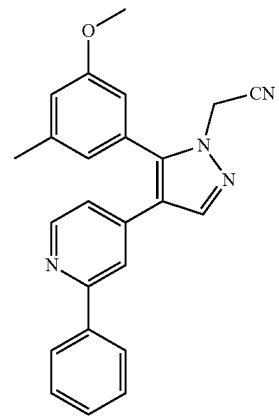

To a solvent mixture of THF and water (4:1, 10 mL) were added the mixture prepared in Example 22 (100 mg, 0.30 mmol), phenylboronic acid (43.9 mg, 0.36 mmol), dichlorobis(triphenylphosphine)palladium (II) (11 mg, 0.02 mmol) and potassium carbonate (42 mg, 0.30 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:3, v/v): (70 mg, 62%); m.p. 51-52° C.; $^1$H NMR (CDCl$_3$) δ 2.41 (s, 3H), 3.81 (s, 3H), 4.95 (s, 2H), 6.76 (s, 1H), 6.82 (s, 1H), 6.95 (s, 1H), 7.06 (d, J=4.5 Hz, 1H), 7.41-7.44 (m, 3H), 7.58 (s, 1H), 7.80 (d, J=6.3 Hz, 2H), 8.01 (s, 1H), 8.53 (d, J=4.8 Hz, 1H) $^{13}$C NMR (CDCl$_3$) δ 21.57, 37.76, 55.49, 112.31, 114.07, 116.90, 118.29, 119.60, 119.70, 122.75, 126.83, 128.71, 129.03, 129.11, 139.21, 139.61, 140.45, 141.47, 141.89, 149.88, 157.70, 160.51.

Example 34

Preparation of [5-(3-methoxy-5-methylphenyl)-4-(2-(pyridin-3-yl)pyridin-4-yl)-pyrazol-1-yl]acetonitrile

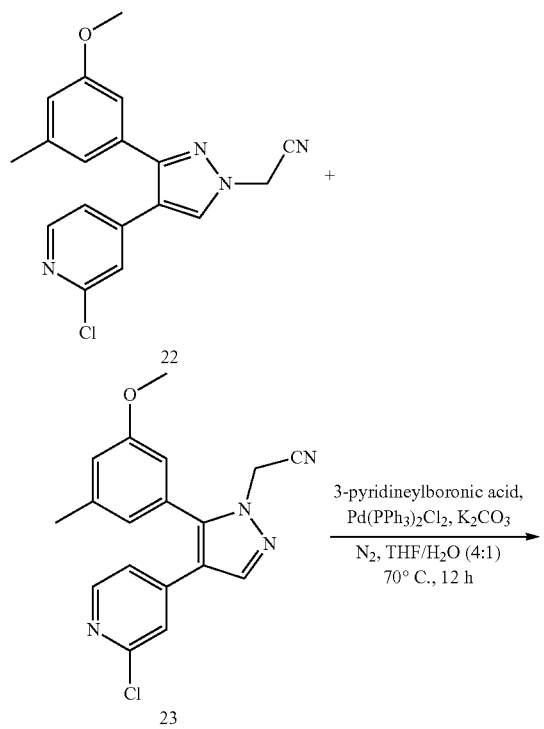

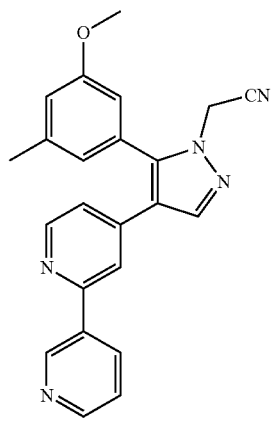

25b

To a solvent mixture of THF and water (4:1, 10 mL) were added the mixture prepared in Example 22 (300 mg, 0.89 mmol), 3-pyridineboronic acid (0.13 g, 1.06 mmol), dichlorobis(triphenylphosphine)palladium (II) (31 mg, 0.04 mmol) and potassium carbonate (130 mg, 0.89 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 2:1, v/v): (62 mg, 55%); m.p. 81-82° C.; $^1$H NMR (CDCl$_3$) δ 2.39 (s, 3H), 3.80 (s, 3H), 4.95 (s, 2H), 6.73 (s, 1H), 6.80 (s, 1H), 6.94 (s, 1H), 7.11 (d, J=5.0 Hz, 1H), 7.34 (dd, J=3.0, 4.8 Hz, 1H), 7.54 (s, 1H), 8.00 (s, 1H), 8.15 (d, J=7.8 Hz, 1H), 8.54 (d, J=5.1 Hz, 1H), 8.60 (d, J=4.4 Hz, 1H), 8.89 (s, 1H); $^{13}$C NMR (CDCl$_3$) δ 21.62, 37.79, 55.50, 112.38, 114.08, 116.81, 118.15, 119.21, 120.35, 122.59, 123.59, 128.90, 134.30, 134.78, 139.57, 140.71, 141.57, 141.97, 148.02, 149.92, 150.34, 154.99, 160.48.

Example 35

Preparation of [5-(3-methoxy-5-methylphenyl)-4-(2-acetylphenyl)pyridin-4-yl)-pyrazol-1-yl]acetonitrile

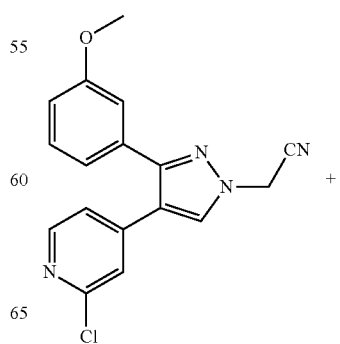

-continued

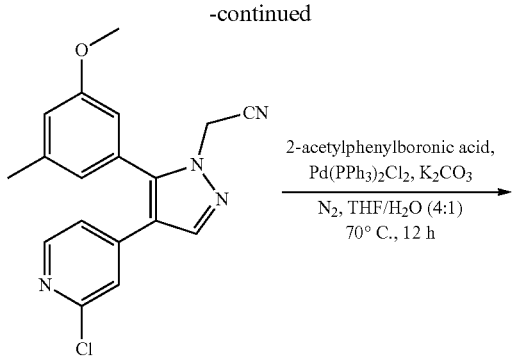

2-acetylphenylboronic acid,
Pd(PPh₃)₂Cl₂, K₂CO₃
───────────────→
N₂, THF/H₂O (4:1)
70° C., 12 h

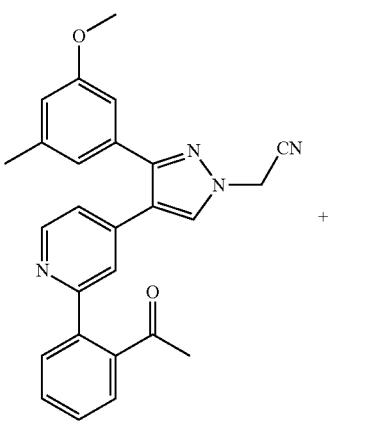

+

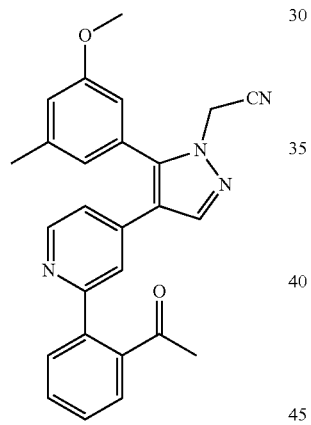

To a solvent mixture of THF and water (4:1, 10 mL) were added the mixture prepared in Example 22 (320 mg, 0.95 mmol), 2-acetylphenyl boronic acid (0.19 g, 1.13 mmol), dichlorobis(triphenylphosphine)palladium (II) (33 mg, 0.05 mmol) and potassium carbonate (131 mg, 0.95 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (102 mg, 82%); m.p. 58-59° C.; ¹H NMR (CDCl₃) δ 2.19 (s, 3H), 2.39 (s, 3H), 3.79 (s, 3H), 4.95 (s, 2H), 6.72 (s, 1H), 6.79 (s, 1H), 6.92 (s, 1H), 7.06 (d, J=4.3 Hz, 1H), 7.34 (d, J=7.5 Hz, 1H), 7.39-7.48 (m, 4H), 7.98 (s, 1H), 8.43 (d, J=5.1 Hz, 1H); ¹³C NMR (CDCl₃) δ 21.59, 30.48, 37.80, 55.47, 112.20, 114.17, 116.92, 119.23, 119.92, 119.96, 122.67, 127.60, 128.68, 128.93, 128.98, 130.23, 138.65, 139.60, 140.59, 141.46, 141.54, 141.95, 149.48, 157.79, 160.44, 204.11.

Example 36

Preparation of [5-(3-methoxy-5-methylphenyl)-4-(2-(3-acetylphenyl)pyridin-4-yl)-pyrazol-1-yl]acetonitrile

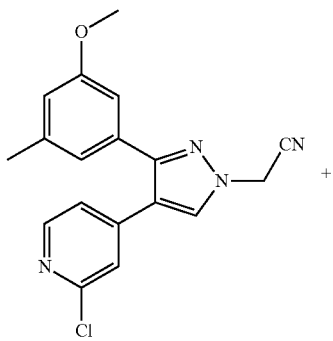

+

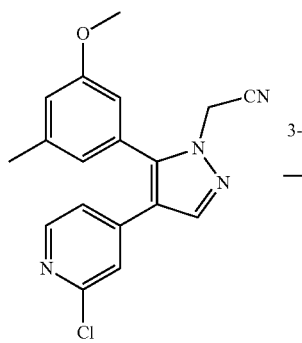

3-acetylphenylboronic acid,
Pd(PPh₃)₂Cl₂, K₂CO₃
───────────────→
N₂, THF/H₂O (4:1)
70° C., 12 h

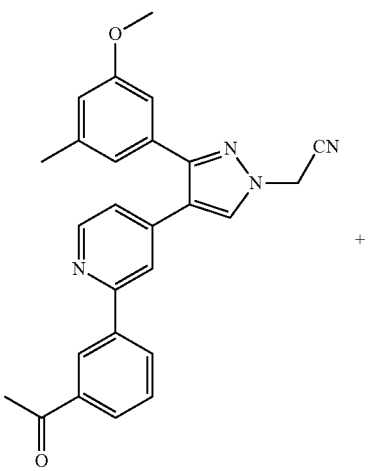

+

-continued

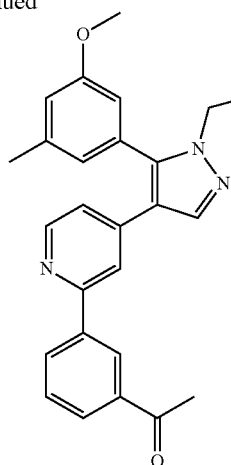

To a solvent mixture of THF and water (4:1, 10 mL) were added the mixture prepared in Example 22 (320 mg, 0.95 mmol), 3-acetylphenylboronic acid (0.19 g, 1.13 mmol), dichlorobis(triphenylphosphine)palladium (II) (33 mg, 0.05 mmol) and potassium carbonate (131 mg, 0.95 mmol), and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (96 mg, 77%); m.p. 65-66° C.; ¹H NMR (CDCl₃) δ 2.39 (s, 3H), 2.62 (s, 3H), 3.79 (s, 3H), 4.96 (s, 2H), 6.74 (s, 1H), 6.80 (s, 1H), 6.95 (s, 1H), 7.10 (bs, 1H), 7.50 (t, J=7.5 Hz, 1H), 7.56 (s, 1H), 7.94-8.00 (m, 3H), 8.29 (s, 1H), 8.52 (d, J=4.2 Hz, 1H); ¹³C NMR (CDCl₃) δ 21.59, 26.78, 37.77, 55.78, 112.33, 114.14, 116.93, 118.18, 119.32, 120.14, 122.64, 126.60, 128.68, 129.01, 131.39, 137.53, 139.59, 139.72, 140.66, 141.54, 141.93, 150.05, 156.54, 160.45, 197.89.

Example 37

Preparation of [5-(3-methoxy-5-methylphenyl)-4-(2-(4-acetylphenyl)pyridin-4-yl)-pyrazol-1-yl]acetonitrile

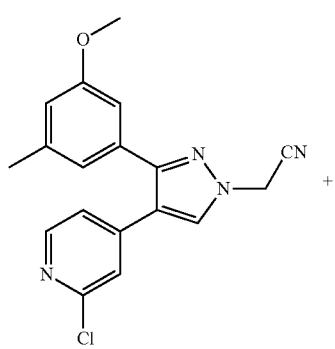

+

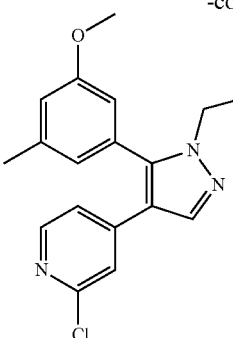

4-acetylphenylboronic acid, Pd(PPh₃)₂Cl₂, K₂CO₃
————————————→
N₂, THF/H₂O (4:1)
70° C., 12 h

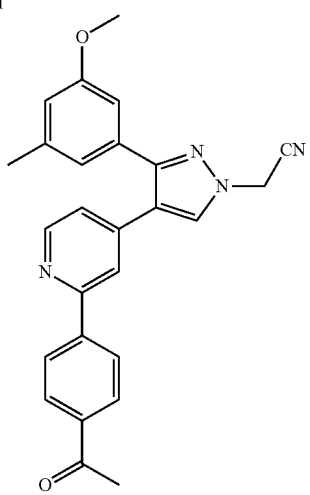

+

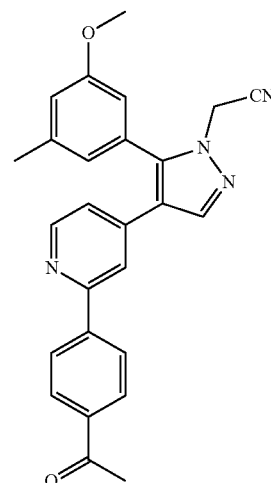

To a solvent mixture of THF and water (4:1, 10 mL) were added the mixture prepared in Example 22 (320 mg, 0.95 mmol), 4-acetylphenyl boronic acid (0.19 g, 1.13 mmol), dichlorobis(triphenylphosphine)palladium (II) (33 mg, 0.05 mmol) and potassium carbonate (131 mg, 0.95 mmol), and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (93 mg, 75%); m.p. 156-157° C.; ¹H NMR (CDCl₃) δ 2.42 (s, 3H), 2.65 (s, 3H), 3.82 (s, 3H), 4.97 (s, 2H), 6.75 (s, 1H), 6.82 (s, 1H), 6.96 (s, 1H), 7.12 (d, J=4.9 Hz, 1H), 7.60 (s, 1H), 7.87 (d, J=8.1 Hz, 2H), 7.99-8.02 (m, 3H), 8.56 (d, J=5.1 Hz, 1H); $^{13}$C NMR (CDCl$_3$) δ 21.60, 26.78, 37.78, 55.52, 112.34, 114.02, 116.86, 118.62, 119.33, 120.38, 122.67, 126.90, 128.76, 129.01, 137.12, 139.56, 140.61, 141.58, 141.96, 143.49, 150.20, 156.29, 160.54, 197.88.

Example 38

Preparation of [5-(3-methoxy-5-methylphenyl)-4-(2-(2-acetamidophenyl)pyridin-4-yl)-pyrazol-1-yl]acetonitrile

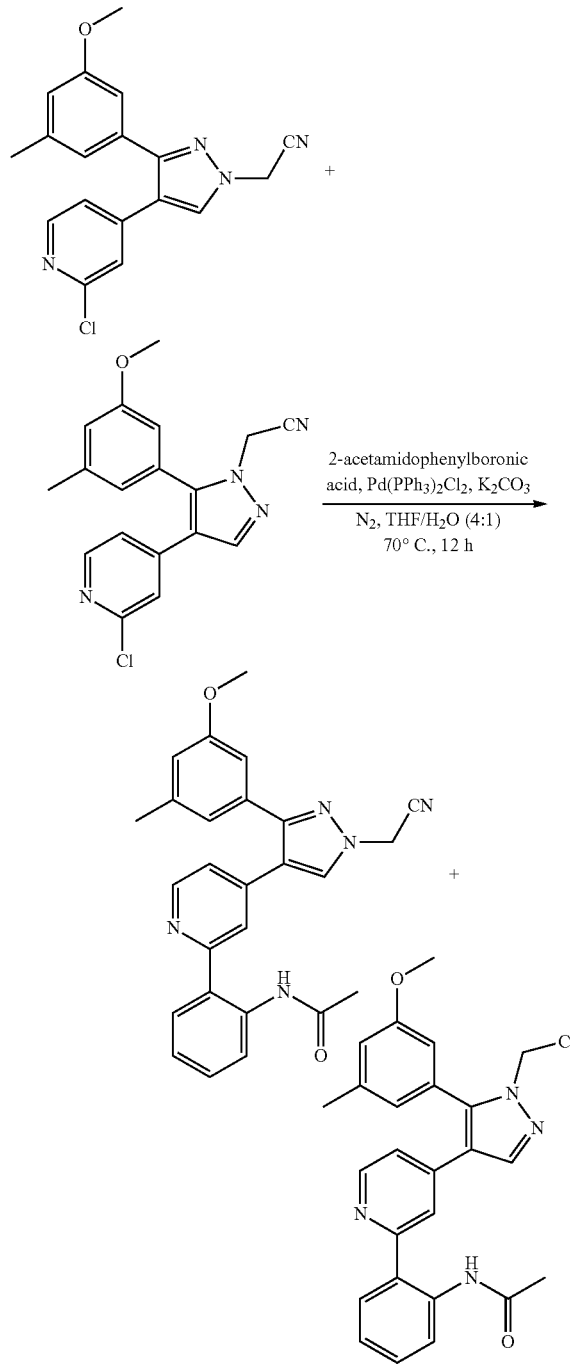

To a solvent mixture of THF and water (4:1, 10 mL) were added the mixture prepared in Example 22 (0.31 g, 0.92 mmol), 2-acetamidophenyl boronic acid (0.10 g, 1.10 mmol), dichlorobis(triphenylphosphine)palladium (II) (33 mg, 0.05 mmol) and potassium carbonate (130 mg, 0.92 mmol), and stirred at 70° C. for 12 hours under to nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 2:1, v/v): (89 mg, 69%); m.p. 87-88° C.; $^1$H NMR (CDCl$_3$) δ 2.16 (s, 3H), 2.42 (s, 3H), 3.82 (s, 3H), 4.96 (s, 2H), 6.75 (s, 1H), 6.82 (s, 1H), 6.96 (s, 1H), 7.06 (t, J=7.4 Hz, 1H), 7.13 (d, J=4.8 Hz, 1H), 7.21 (d, J=7.6 Hz, 1H), 7.37 (t, J=7.6 Hz, 1H), 7.52 (s, 1H), 8.01 (s, 1H), 8.48 (d, J=5.5 Hz, 2H), 12.05 (s, 1H); $^{13}$C NMR (CDCl$_3$) δ 21.65, 25.31, 37.8, 55.53, 112.42, 114.07, 116.78, 119.20, 119.35, 120.62, 121.82, 122.65, 123.30, 125.6, 128.68, 128.94, 130.00, 137.56, 139.54, 141.37, 141.65, 142.07, 147.80, 158.43, 160.55, 168.62, 198.95.

Example 39

Preparation of [5-(3-methoxy-5-methylphenyl)-4-(2-(3-acetamidophenyl)pyridin-4-yl)-pyrazol-1-yl]acetonitrile

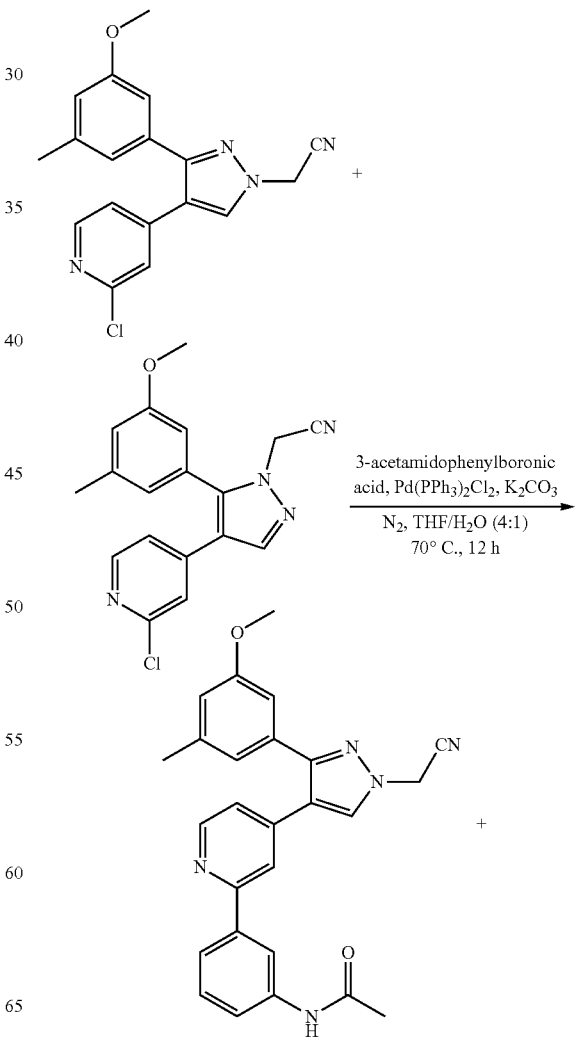

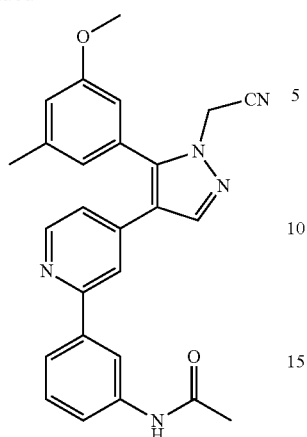

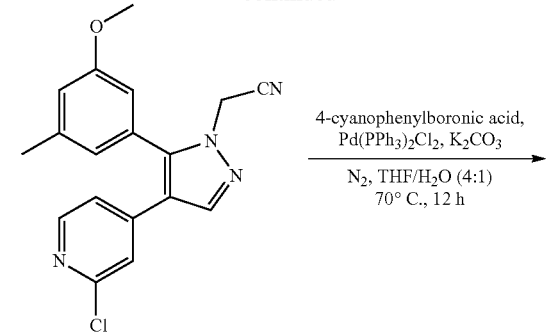

To a solvent mixture of THF and water (4:1, 10 mL) were added the mixture prepared in Example 22 (320 mg, 0.95 mmol), 3-acetamidophenyl boronic acid (0.11 g, 1.13 mmol), dichlorobis(triphenylphosphine)palladium (II) (34 mg, 0.05 mmol) and potassium carbonate (131 mg, 0.95 mmol), and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 2:1, v/v): (81 mg, 63%); m.p. 97-98° C.; $^1$H NMR (CDCl$_3$) δ 2.15 (s, 3H), 2.39 (s, 3H), 3.81 (s, 3H), 4.95 (s, 2H), 6.74 (s, 1H), 6.79 (s, 1H), 6.93 (s, 1H), 7.01 (d, J=4.7 Hz, 1H), 7.32-7.37 (m, 1H), 7.43 (d, J=7.7 Hz, 1H), 7.57 (s, 1H), 7.75-7.77 (m, 2H), 7.98 (s, 1H), 7.99 (s, 1H), 8.46 (d, J=4.8 Hz, 1H); $^{13}$C NMR (CDCl$_3$) δ 21.56, 24.51, 37.76, 55.52, 112.24, 114.07, 117.00, 118.36, 119.50, 119.89, 120.67, 122.39, 122.78, 129.08, 129.39, 138.57, 139.60, 139.92, 140.49, 141.52, 141.88, 149.81, 157.12, 160.45, 168.55.

Example 40

Preparation of [5-(3-methoxy-5-methylphenyl)-4-(2-(4-cyanophenyl)pyridin-4-yl)-pyrazol-1-yl]acetonitrile

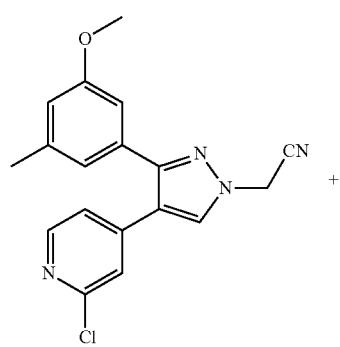

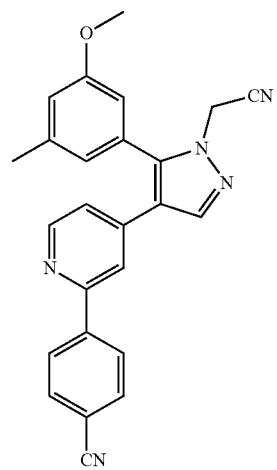

To a solvent mixture of THF and water (4:1, 10 mL) were added the mixture prepared in Example 22 (320 mg, 0.95 mmol), 4-cyanophenylboronic acid (0.17 g, 1.13 mmol), dichlorobis(triphenylphosphine)palladium (II) (34 mg, 0.05 mmol) and potassium carbonate (131 mg, 0.95 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (92 mg, 77%); m.p. 161-162° C.; $^1$H NMR (CDCl$_3$) δ 2.42 (s, 3H), 3.85 (s, 3H), 4.96 (s, 2H), 6.75 (s, 1H), 6.82 (s, 1H), 6.96 (s, 1H), 7.13 (d, J=4.9 Hz, 1H), 7.58 (s, 1H), 7.71 (d, J=8.1 Hz, 2H), 7.91 (d, J=8.1 Hz, 2H), 8.02 (s, 1H), 8.56 (d, J=5.1 Hz, 1H); $^{13}$C NMR (CDCl$_3$) δ 21.58, 37.80, 55.51, 112.40, 112.47, 113.95, 116.85, 118.53, 118.73, 119.20, 120.71, 122.65, 127.30, 129.01, 132.48, 139.51, 140.82, 141.60, 142.00, 143.39, 150.32, 155.46, 160.59.

Example 41

Preparation of [5-(3-methoxy-5-methylphenyl)-4-(2-(4-dimethylaminophenyl)pyridin-4-yl)-pyrazol-1-yl]acetonitrile

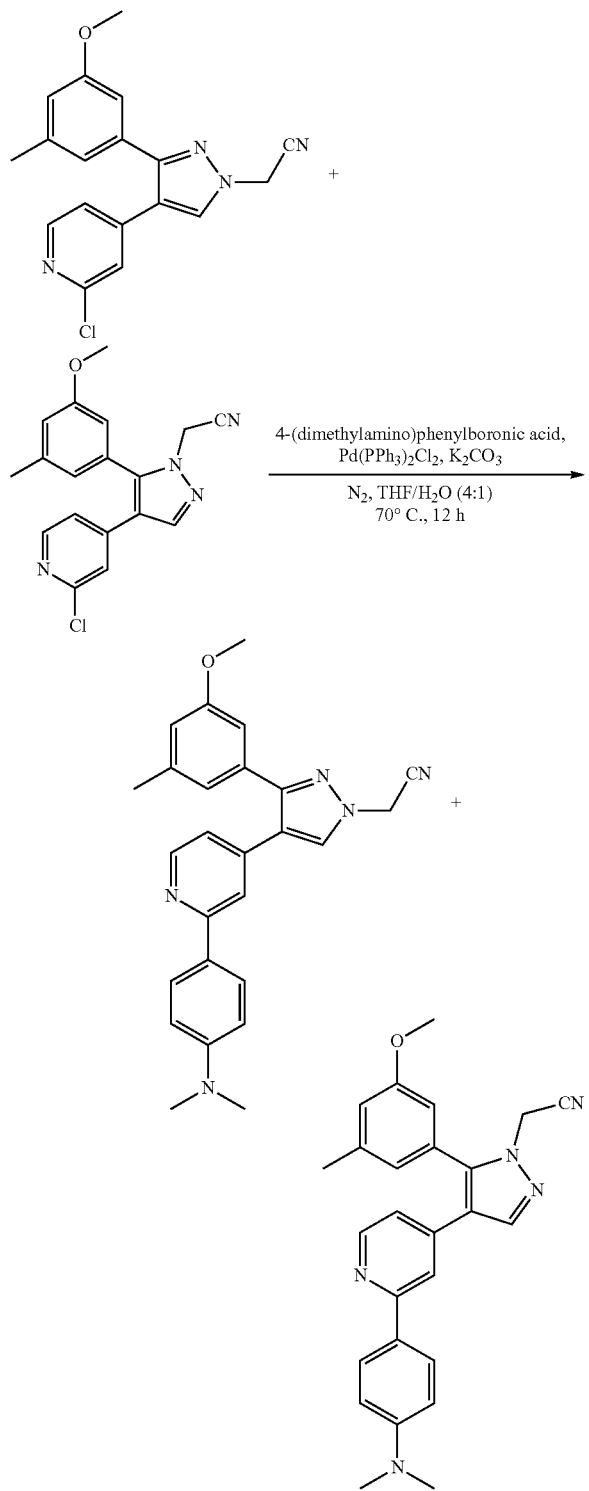

To a solvent mixture of THF and water (4:1, 10 mL) were added the mixture prepared in Example 22 (320 mg, 0.95 mmol), 4-(dimethylamino)phenylboronic acid (0.19 g, 1.13 mmol), dichlorobis(triphenylphosphine)palladium (II) (34 mg, 0.05 mmol) and potassium carbonate (131 mg, 0.95 mmol), and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (62 mg, 50%); m.p. 150-151° C.; $^1$H NMR (CDCl$_3$) δ 2.41 (s, 3H), 3.02 (s, 6H), 3.81 (s, 3H), 4.95 (s, 2H), 6.76-6.81 (m, 4H), 6.91-6.93 (m, 2H), 7.50 (s, 1H), 7.73 (d, J=8.6 Hz, 2H), 8.00 (s, 1H), 8.46 (d, J=5.1 Hz, 1H); $^{13}$C NMR (CDCl$_3$) δ 21.58, 37.74, 40.38, 55.48, 112.12, 114.12, 116.82, 116.95, 118.33, 119.98, 122.82, 127.04, 127.63, 129.23, 139.68, 139.94, 141.33, 141.70, 149.68, 151.05, 157.84, 160.42.

Example 42

Preparation of [5-(3-methoxy-5-methylphenyl)-4-(2-(4-phenoxyphenyl)pyridin-4-yl)-pyrazol-1-yl]acetonitrile

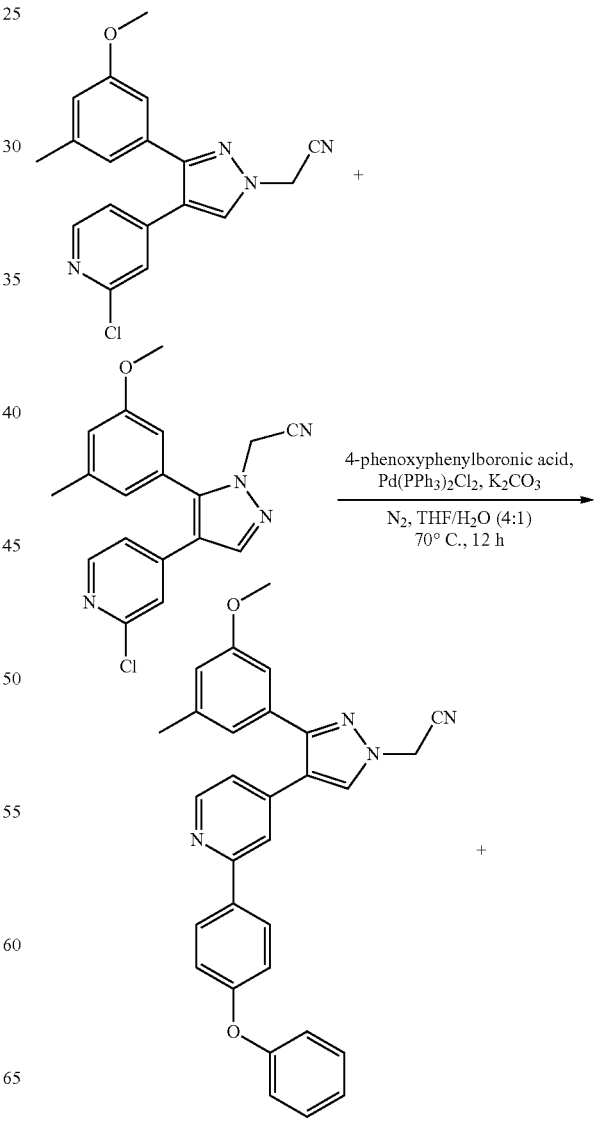

-continued

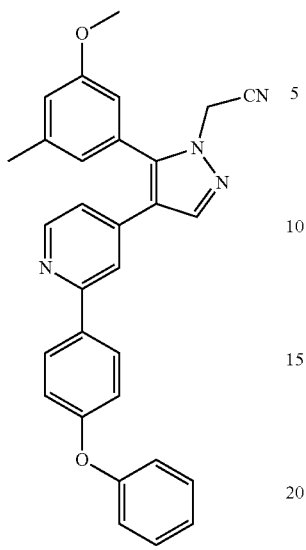

To a solvent mixture of THF and water (4:1, 10 mL) were added the mixture prepared in Example 22 (320 mg, 0.95 mmol), 4-phenoxyphenyl boronic acid (0.24 g, 1.13 mmol), dichlorobis(triphenylphosphine)palladium (II) (34 mg, 0.05 mmol) and potassium carbonate (0.13 g, 0.95 mmol), and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:3, v/v): (96 mg, 69%); m.p. 69-70° C.; $^1$H NMR (CDCl$_3$) δ 2.41 (s, 3H), 3.81 (s, 3H), 4.96 (s, 2H), 6.76 (s, 1H), 6.82 (s, 1H), 6.95 (s, 1H), 7.05 (d, 7.3 Hz, 5H), 7.14 (t, J=7.1 Hz, 1H), 7.36 (t, J=7.1 Hz, 2H), 7.56 (s, 1H), 7.78 (d, J=8.0 Hz, 2H), 8.01 (s, 1H), 8.51 (d, J=3.8 Hz, 1H); $^{13}$C NMR (CDCl$_3$) δ 21.59, 37.78, 55.50, 112.34, 114.14, 116.90, 117.87, 118.75, 119.23, 119.46, 122.73, 123.69, 128.38, 129.07, 129.88, 133.77, 139.63, 140.88, 141.50, 141.99, 149.50, 156.74, 156.77, 158.46, 160.43.

General Synthesis Route

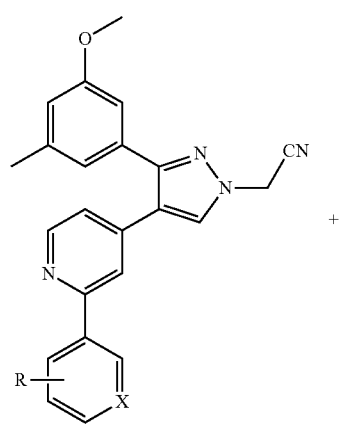 +

-continued

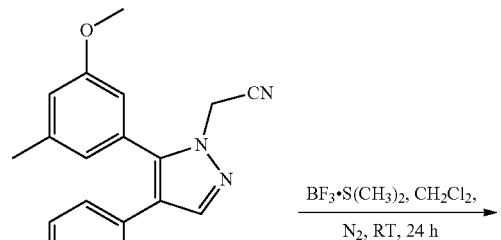

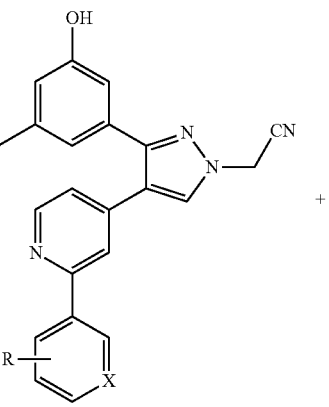

To a solution of the methoxy compound (0.12 mmol) in dichloromethane (4 mL) was dropwise added borontrifluoride-dimethylsulfide (0.13 mL, 1.2 mmol) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification

Example 43

Preparation of [3-(3-hydroxy-5-methylphenyl)-4-(2-phenylpyridin-4-yl)-pyrazol-1-yl]acetonitrile

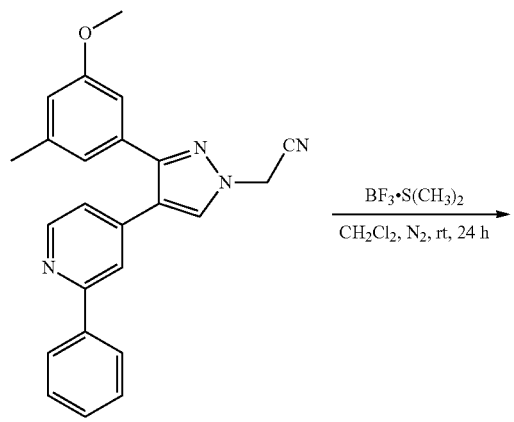

Borontrifluoride-dimethylsulfide (0.13 mL, 1.2 mmol) was dropwise added to a solution of the methoxy compound (45.6 mg, 0.12 mmol) prepared in Example 23 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (31 mg, 70%).

m.p. 110-111° C.; $^1$H NMR (CDCl$_3$) δ 2.31 (s, 3H), 5.09 (s, 2H), 6.54 (s, 1H), 6.73 (s, 1H), 6.98-7.03 (m, 2H), 7.28-7.32 (m, 3H), 7.51 (s, 1H), 7.62-7.65 (m, 3H), 8.30 (s, 1H); $^{13}$C NMR (CDCl$_3$) δ 1.51, 39.82, 112.71, 113.60, 117.21, 119.73, 120.33, 120.77, 121.35, 127.14, 128.79, 129.29, 130.37, 132.21, 138.30, 140.62, 141.52, 148.83, 149.41, 150.24, 151.30, 156.81, 157.68.

Example 44

Preparation of [3-(3-hydroxy-5-methylphenyl)-4-(2-(pyridin-3-yl)pyridin-4-yl)-pyrazol-1-yl]acetonitrile

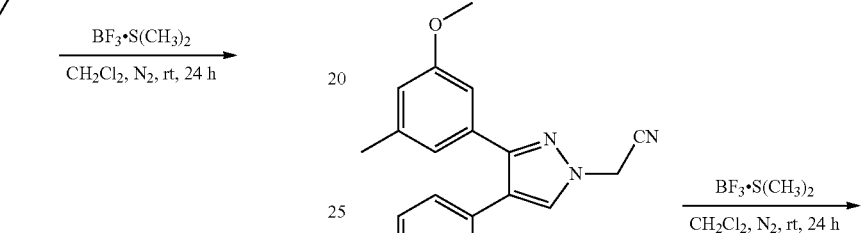

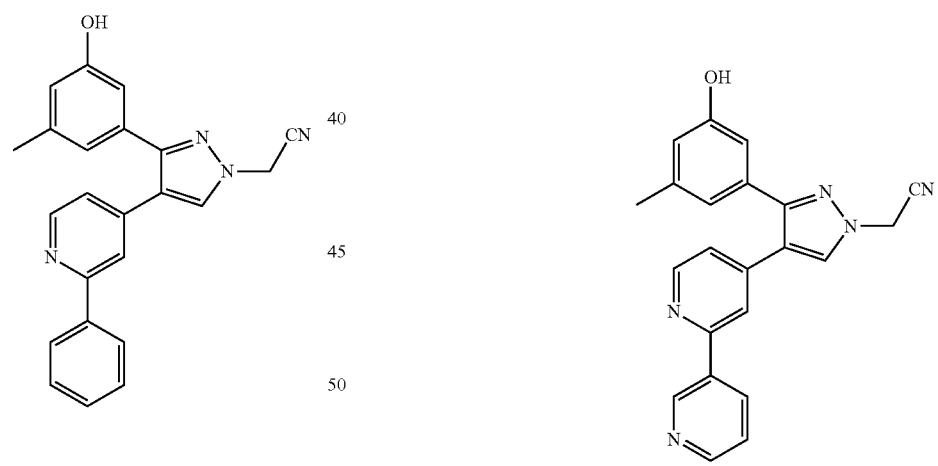

Borontrifluoride-dimethylsulfide (0.09 mL, 0.79 mmol) was dropwise added to a solution of the methoxy compound (30.5 mg, 0.08 mmol) prepared in Example 24 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (35 mg, 79%).

m.p. 127-128° C.; $^1$H NMR (CDCl$_3$) δ 2.26 (s, 3H), 5.13 (s, 2H), 6.68 (s, 1H), 6.70 (s, 1H), 6.92 (s, 1H), 7.12 (d, J=4.9 Hz, 1H), 7.31 (dd, J=2.9, 4.8 Hz, 1H), 7.55 (s, 1H), 7.79 (s, 1H), 8.13 (d, J=7.9 Hz, 1H), 8.40-8.45 (m, 2H), 8.77 (s, 1H); $^{13}$C NMR (CDCl$_3$) δ 1.45, 39.86, 113.05, 133.68, 117.25, 119.61, 119.72, 120.38, 122.04, 124.06, 130.46, 132.42, 134.82, 135.12, 140.54, 141.23, 146.95, 148.77, 149.84, 151.54, 154.08, 157.28.

Example 45

Preparation of [3-(3-hydroxy-5-methylphenyl)-4-(2-(2-(acetylphenyl)pyridin-4-yl)-pyrazol-1-yl]acetonitrile

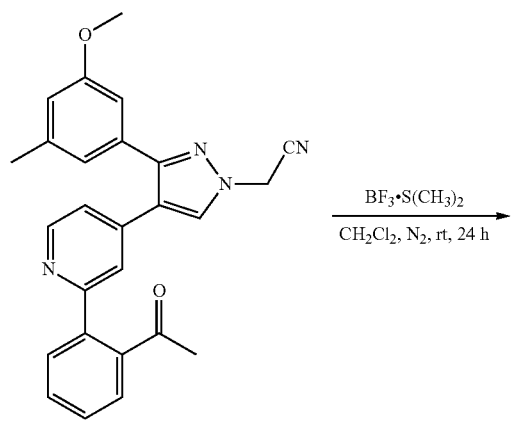

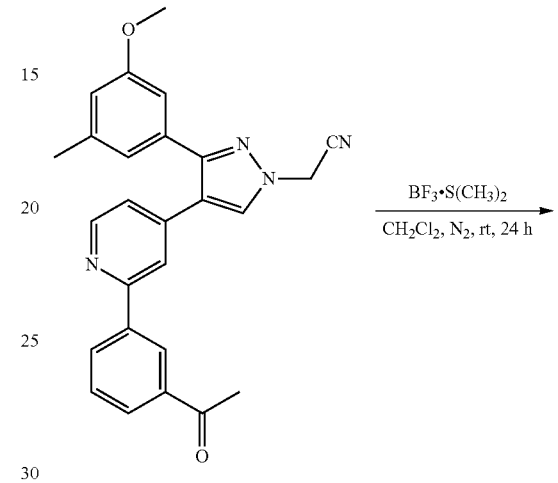

m.p. 105-106° C.; $^1$H NMR (CDCl$_3$) δ 0.27 (s, 3H), 2.39 (s, 3H), 5.14 (s, 2H), 6.52 (s, 1H), 6.64 (s, 1H), 7.01 (s, 1H), 7.11 (d, J=5.0 Hz, 1H), 7.35-7.48 (m, 5H), 7.72 (s, 1H), 8.45 (d, J=5.1 Hz, 1H).

Example 46

Preparation of [3-(3-hydroxy-5-methylphenyl)-4-(2-(3-(acetylphenyl)pyridin-4-yl)-pyrazol-1-yl]acetonitrile

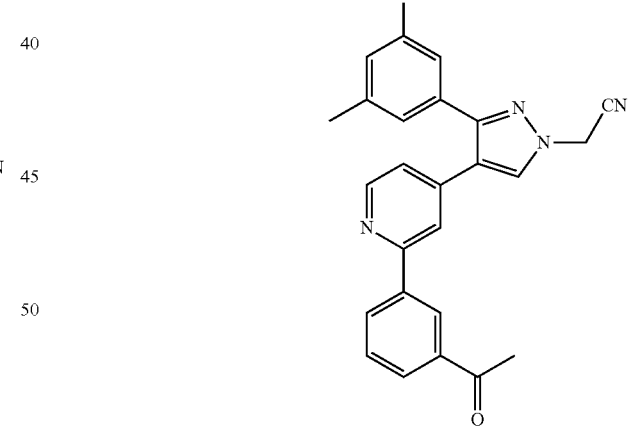

Borontrifluoride-dimethylsulfide (0.13 mL, 1.2 mmol) was dropwise added to a solution of the methoxy compound (50.7 mg, 0.12 mmol) prepared in Example 25 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (21 mg, 43%).

Borontrifluoride-dimethylsulfide (0.13 mL, 1.2 mmol) was dropwise added to a solution of the methoxy compound (50.7 mg, 0.12 mmol) prepared in Example 26 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (30 mg, 61%).

m.p. 84-85° C.; $^1$H NMR (CDCl$_3$) δ 2.29 (s, 3H), 2.49 (s, 3H), 5.16 (s, 2H), 6.59 (s, 1H), 6.73 (s, 1H), 6.97 (s, 1H), 7.11

(d, J=4.8 Hz, 1H), 7.36 (t, J=7.7 Hz, 1H), 7.53 (s, 1H), 7.77 (s, 1H), 7.83 (t, J=7.2 Hz, 2H), 8.05 (s, 1H), 8.35 (d, J=5.1 Hz, 1H).

Example 47

Preparation of [3-(3-hydroxy-5-methylphenyl)-4-(2-(4-(acetylphenyl)pyridin-4-yl)-pyrazol-1-yl]acetonitrile

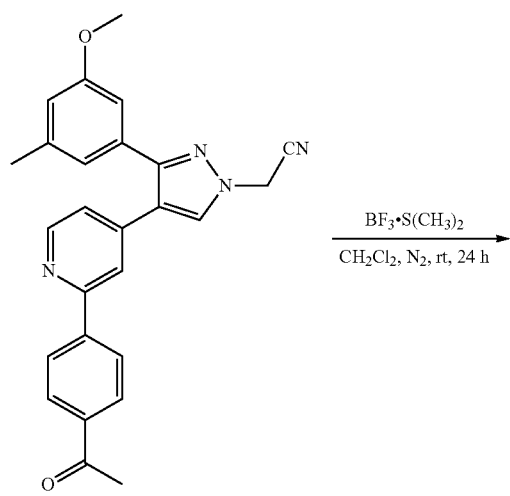

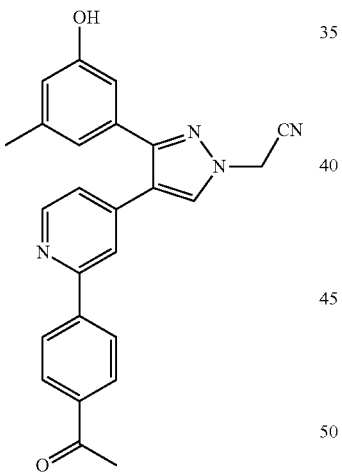

Borontrifluoride-dimethylsulfide (0.25 mL, 2.37 mmol) was dropwise added to a solution of the methoxy compound (0.1 g, 0.24 mmol) prepared in Example 27 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (22 mg, 44%).

m.p. 106-108° C.; $^1$H NMR (CDCl$_3$) δ 0.33 (s, 3H), 2.59 (s, 3H), 5.19 (s, 2H), 6.61 (s, 1H), 6.77 (s, 1H), 6.98 (s, 1H), 7.17 (d, J=4.8 Hz, 1H), 7.60 (s, 1H), 7.74 (d, J=8.0 Hz, 2H), 7.83 (s, 1H), 7.88 (d, J=8.0 Hz, 2H), 8.48 (d, J=4.8 Hz, 1H).

Example 48

Preparation of [3-(3-hydroxy-5-methylphenyl)-4-(2-(2-(acetamidophenyl)pyridin-4-yl)-pyrazol-1-yl] acetonitrile

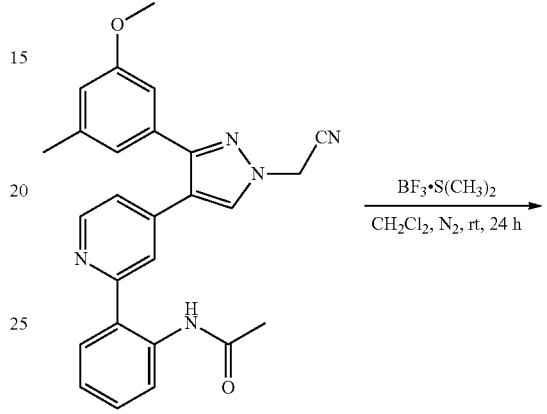

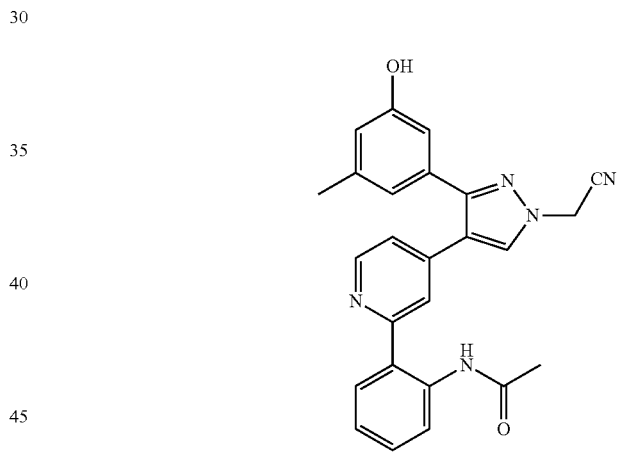

Borontrifluoride-dimethylsulfide (0.13 mL, 12 mmol) was dropwise added to a solution of the methoxy compound (52.5 mg, 0.12 mmol) prepared in Example 28 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (33 mg, 66%).

m.p. 150-151° C.; $^1$H NMR (DMSO-d$_6$) δ 2.06 (s, 3H), 2.23 (s, 3H), 5.60 (s, 2H), 6.65 (s, 2H), 6.76 (s, 1H), 7.14 (t, J=7.4 Hz, 1H), 7.27 (d, J=4.5 Hz, 1H), 7.39 (t, J=7.4 Hz, 1H), 7.56 (d, J=7.5 Hz, 1H), 7.74 (s, 1H), 8.26 (d, J=7.1 Hz, 1H), 8.44 (s, 1H), 8.61 (d, J=4.8 Hz, 1H), 9.48 (s, 1H), 11.79 (s, 1H); $^{13}$C NMR (DMSO) δ 1.50, 25.12, 112.96, 116.25, 116.56, 118.39, 120.23, 121.16, 121.97, 122.20, 123.98, 126.88, 129.63, 130.07, 133.09, 133.72, 137.59, 139.72, 142.27, 148.68, 150.64, 157.76, 157.86, 168.46.

Example 49

Preparation of [3-(3-hydroxy-5-methylphenyl)-4-(2-(3-(acetamidophenyl)pyridin-4-yl)-pyrazol-1-yl]acetonitrile

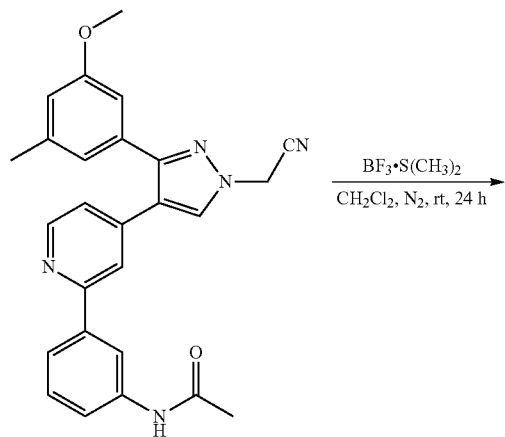

Borontrifluoride-dimethylsulfide (0.13 mL, 12 mmol) was dropwise added to a solution of the methoxy compound (52.5 mg, 0.12 mmol) prepared in Example 29 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (37 mg, 72%).

$^1$H NMR (CD$_3$OD) δ 2.14 (s, 3H), 2.24 (s, 3H), 5.39 (s, 2H), 6.70 (s, 2H), 6.79 (s, 1H), 7.21 (d, J=3.6 Hz, 1H), 7.35-7.43 (m, 2H), 7.60-7.65 (m, 2H), 8.03 (s, 1H), 8.14 (s, 1H), 8.43 (d, J=4.6 Hz, 1H); $^{13}$C NMR (CD$_3$OD) δ 20.14, 22.56, 38.96, 112.58, 114.43, 116.08, 118.56, 118.94,

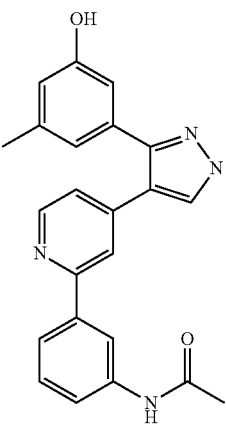

120.11, 120.48, 120.66, 121.15, 121.27, 122.38, 128.87, 131.65, 133.19, 139.02, 139.55, 139.75, 142.03, 148.93, 151.40, 157.26, 170.33.

Example 50

Preparation of [3-(3-hydroxy-5-methylphenyl)-4-(2-(4-(cyanophenyl)pyridin-4-yl)-pyrazol-1-yl]acetonitrile

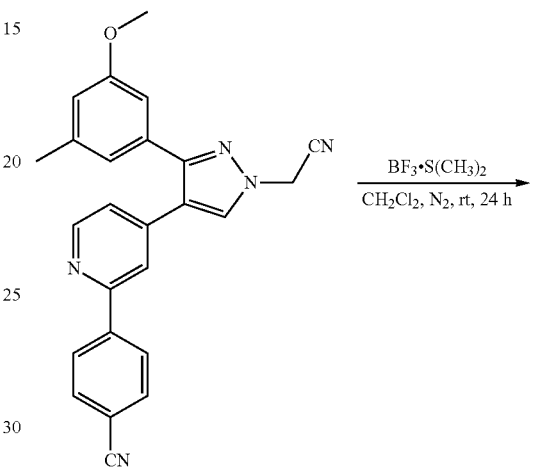

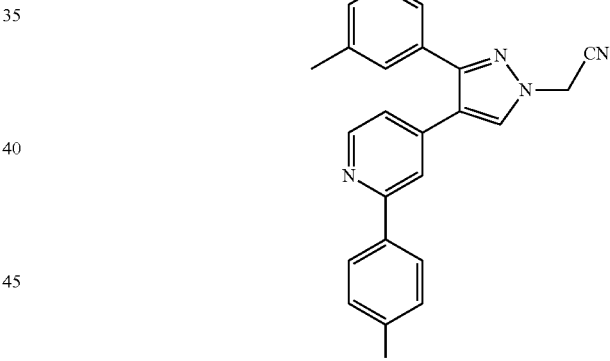

Borontrifluoride-dimethylsulfide (0.13 mL, 1.2 mmol) was dropwise added to a solution of the methoxy compound (48.6 mg, 0.12 mmol) prepared in Example 30 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (38 mg, 81%).

m.p. 147-149° C.; $^1$H NMR (CDCl$_3$) δ 2.27 (s, 3H), 5.18 (s, 2H), 6.66 (s, 1H), 6.71 (s, 1H), 6.92 (s, 1H), 7.19 (d, J=4.9 Hz, 1H), 7.59-7.64 (m, 3H), 7.80-7.84 (m, 3H), 8.51 (d, J=5.1 Hz, 1H); $^{13}$C NMR (CDCl$_3$) δ 21.37, 39.94, 112.47, 112.71, 113.50, 117.05, 118.58, 119.64, 120.60, 121.23, 122.22, 127.53, 130.27, 132.51, 132.59, 140.57, 141.52, 142.90, 149.56, 151.42, 155.48, 156.43.

Example 51

Preparation of [3-(3-hydroxy-5-methylphenyl)-4-(2-(4-(dimethylaminophenyl)pyridin-4-yl)-pyrazol-1-yl]acetonitrile

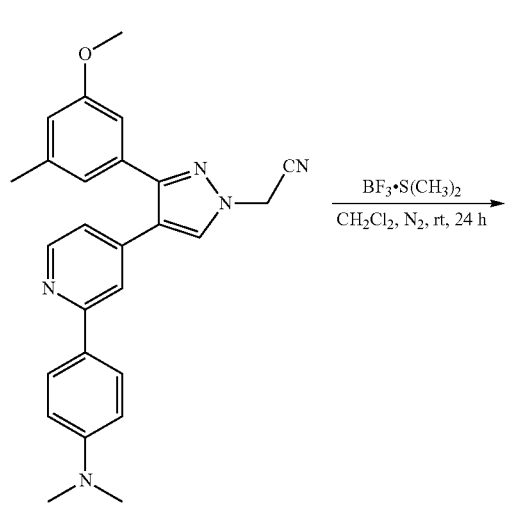

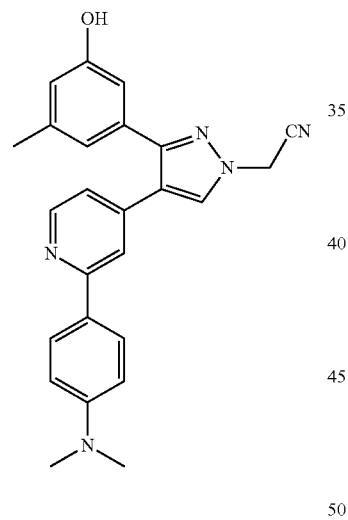

Borontrifluoride-dimethylsulfide (0.13 mL, 1.2 mmol) was dropwise added to a solution of the methoxy compound (50.1 mg, 0.12 mmol) prepared in Example 31 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (37 mg, 75%).

m.p. 138-139° C.; $^1$H NMR (CDCl$_3$) δ 2.29 (s, 3H), 2.92 (s, 6H), 4.99 (s, 2H), 6.60-6.62 (m, 3H), 6.73 (s, 1H), 6.83 (d, J=4.3 Hz, 1H), 6.96 (s, 1H), 7.41 (s, 1H), 7.54-7.57 (m, 3H), 8.11 (d, J=4.8 Hz, 1H); $^{13}$C NMR (CDCl$_3$) δ 21.45, 39.58, 40.22, 112.14, 112.87, 113.69, 117.15, 119.17, 119.94, 120.39, 125.73, 128.03, 130.51, 132.53, 140.40, 141.31, 148.21, 151.12, 151.27, 156.95, 157.46.

Example 52

Preparation of [3-(3-hydroxy-5-methylphenyl)-4-(2-(4-(phenoxyphenyl)pyridin-4-yl)-pyrazol-1-yl]acetonitrile

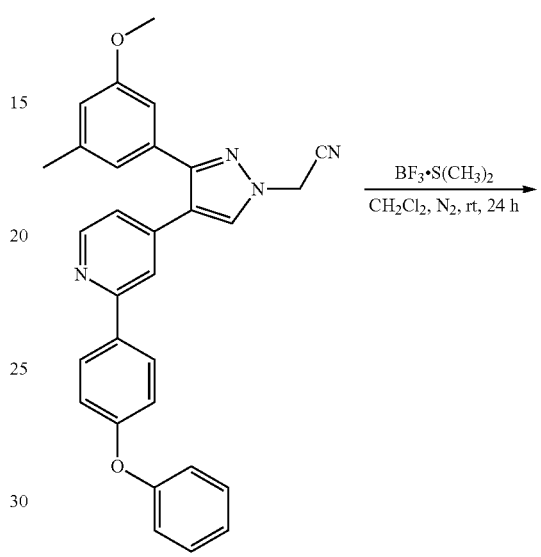

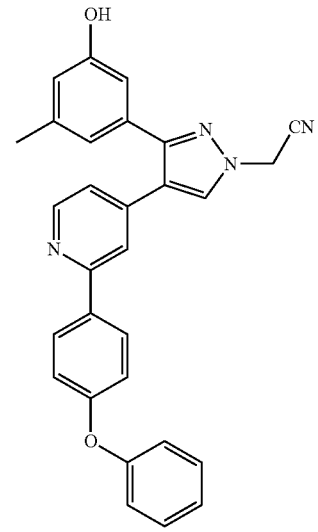

Borontrifluoride-dimethylsulfide (0.13 mL, 1.2 mmol) was dropwise added to a solution of the methoxy compound (56.7 mg, 0.12 mmol) prepared in Example 32 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (34 mg, 62%).

m.p. 104-105° C.; $^1$H NMR (CDCl$_3$) δ 2.29 (s, 3H), 5.09 (s, 2H), 6.62 (s, 1H), 6.71 (s, 1H), 6.90-7.01 (m, 6H), 7.13 (t, 7.2 Hz, 1H), 7.34 (t, J=7.7 Hz, 2H), 7.49 (s, 1H), 7.58 (d, J=8.4

Hz, 2H), 7.68 (s, 1H), 8.28 (d, J=4.8 Hz, 1H); $^{13}$C NMR (CDCl$_3$) δ 21.47, 39.81, 112.66, 117.23, 118.49, 119.43, 119.83, 120.32, 120.52, 121.02, 123.84, 128.67, 129.90, 130.37, 132.36, 133.15, 140.57, 141.54, 148.89, 151.23, 156.42, 156.72, 157.08, 158.56.

Example 53

Preparation of [5-(3-hydroxy-5-methylphenyl)-4-(2-phenylpyridin-4-yl)-pyrazol-1-yl]acetonitrile

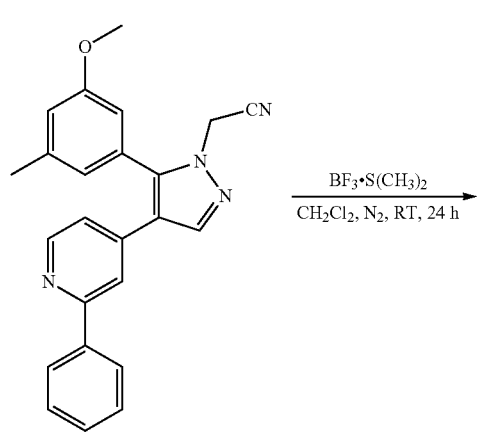

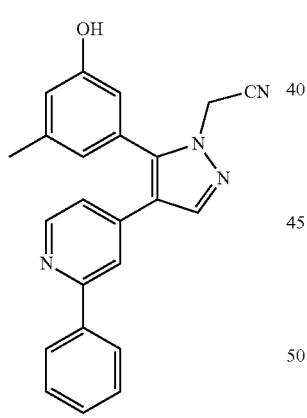

Borontrifluoride-dimethylsulfide (0.13 mL, 1.2 mmol) was dropwise added to a solution of the methoxy compound (45.6 mg, 0.12 mmol) prepared in Example 33 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (22 mg, 51%).

m.p. 96-97° C.; $^1$H NMR (CDCl$_3$) δ 2.38 (s, 3H), 4.90 (s, 2H), 6.37 (s, 1H), 6.71 (s, 1H), 6.87 (s, 1H), 6.95 (d, J=3.9 Hz, 1H), 7.37 (bs, 3H), 7.53 (s, 1H), 7.69 (d, J=3.0 Hz, 2H), 7.96 (s, 1H), 8.37 (d, J=5.1 Hz, 1H).

Example 54

Preparation of [5-(3-hydroxy-5-methylphenyl)-4-(2-(pyridin-3-yl)pyridin-4-yl)-pyrazol-1-yl]acetonitrile

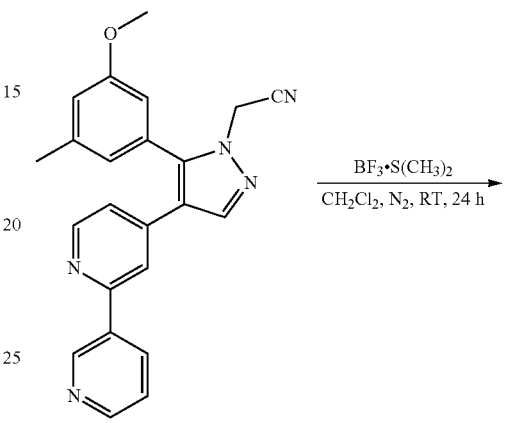

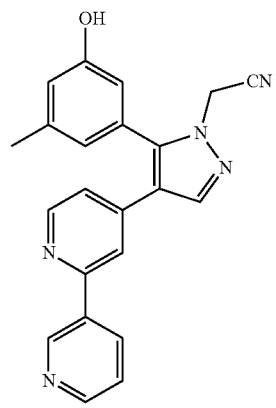

Borontrifluoride-dimethylsulfide (0.13 mL, 1.2 mmol) was dropwise added to a solution of the methoxy compound (45.7 mg, 0.12 mmol) prepared in Example 34 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (24 mg, 55%).

m.p. 109-110° C.; $^1$H NMR (CDCl$_3$) δ 2.36 (s, 3H), 5.00 (s, 2H), 6.72 (s, 2H), 6.94 (s, 1H), 7.23 (d, J=4.2 Hz, 1H), 7.40

(dd, J=2.7, 5.0 Hz, 1H), 7.48 (s, 1H), 8.00 (s, 1H), 8.26 (d, J=7.8 Hz, 1H), 8.54-8.55 (m, 2H), 8.70 (s, 1H).

Example 55

Preparation of [5-(3-hydroxy-5-methylphenyl)-4-(2-(2-acetylphenyl)pyridin-4-yl)-pyrazol-1-yl]acetonitrile

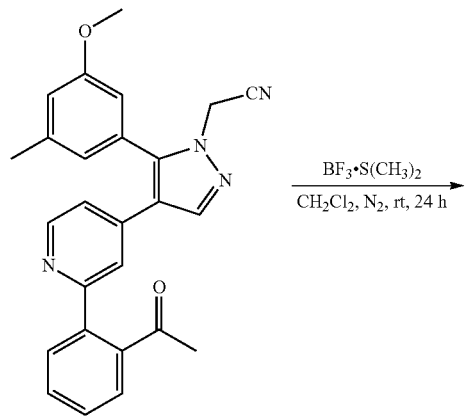

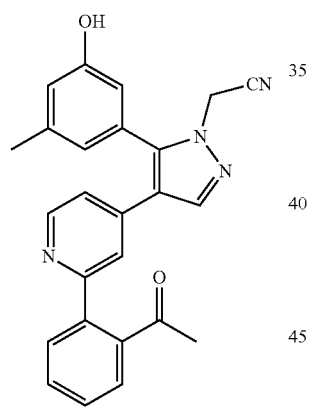

Borontrifluoride-dimethylsulfide (0.13 mL, 1.2 mmol) was dropwise added to a solution of the methoxy compound (50.7 mg, 0.12 mmol) prepared in Example 35 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (23 mg, 47%).

m.p. 96-97° C.; $^1$H NMR (CDCl$_3$) δ 2.24 (s, 3H), 2.31 (s, 3H), 4.90 (s, 2H), 6.34 (s, 1H), 6.64 (s, 1H), 6.79 (s, 1H), 6.98 (d, J=4.5 Hz, 1H), 7.24-7.27 (m, 1H), 7.34 (s, 1H), 7.38 (dd, J=2.4, 3.3 Hz, 2H), 7.52 (dd, J=2.1, 3.3 Hz, 1H), 7.93 (s, 1H), 8.28 (d, J=5.3 Hz, 1H); $^{13}$C NMR (CDCl$_3$) δ 21.42, 29.97, 37.64, 113.79, 113.93, 118.75, 120.14, 120.50, 121.32, 127.92, 128.29, 128.90, 129.36, 130.71, 138.40, 139.52, 140.61, 141.20, 141.54, 142.31, 148.60, 157.73, 157.87, 202.39.

Example 56

Preparation of [5-(3-hydroxy-5-methylphenyl)-4-(2-(3-acetylphenyl)pyridin-4-yl)-pyrazol-1-yl]acetonitrile

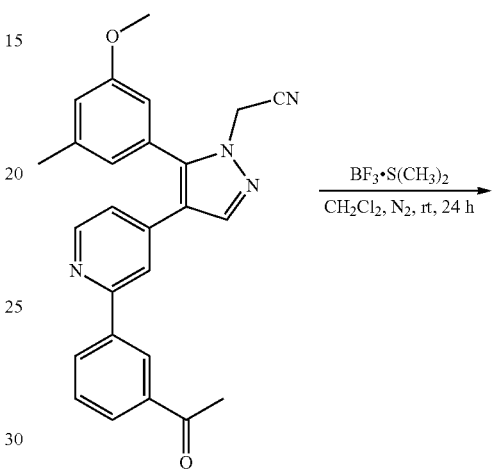

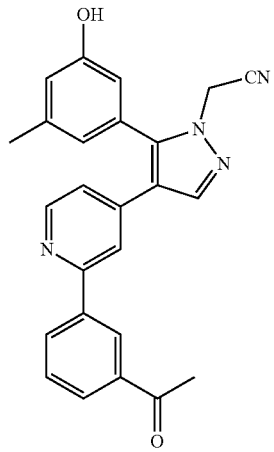

Borontrifluoride-dimethylsulfide (0.13 mL, 1.2 mmol) was dropwise added to a solution of the methoxy compound (50.7 mg, 0.12 mmol) prepared in Example 36 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (32 mg, 65%).

m.p. 123-125° C.; $^1$H NMR (CDCl$_3$) δ 2.34 (s, 3H), 2.58 (s, 3H), 4.95 (s, 2H), 6.37 (s, 1H), 6.69 (s, 1H), 6.87 (s, 1H), 7.00 (d, J=5.0 Hz, 1H), 7.44 (t, J=7.5 Hz, 1H), 7.53 (s, 1H), 7.89-7.95 (m, 3H), 8.19 (s, 1H), 8.37 (d, J=5.1 Hz, 1H), 9.51 (s, 1H); $^{13}$C NMR (CDCl$_3$) δ 21.51, 26.80, 37.66, 114.02, 114.09, 118.73, 118.95, 119.21, 120.55, 121.27, 126.96, 128.32, 129.03, 129.23, 131.81, 137.26, 139.15, 139.69, 141.50, 141.72, 142.24, 149.21, 156.63, 157.89, 198.40.

Example 57

Preparation of [5-(3-hydroxy-5-methylphenyl)-4-(2-(4-acetylphenyl)pyridin-4-yl)-pyrazol-1-yl]acetonitrile

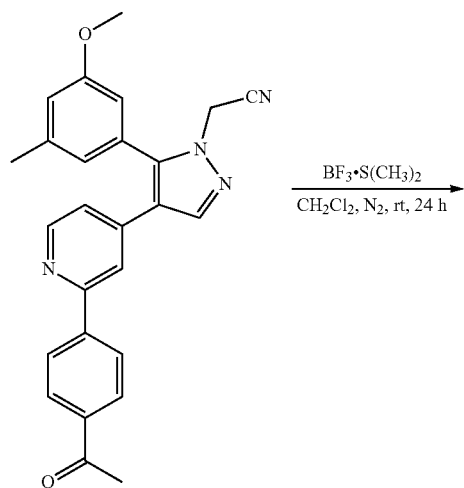

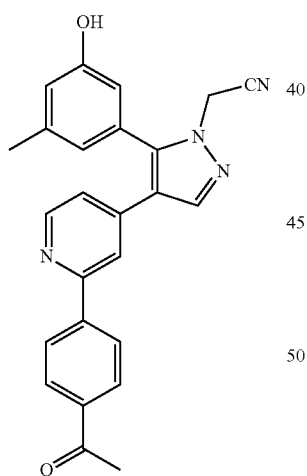

Borontrifluoride-dimethylsulfide (0.25 mL, 2.37 mmol) was dropwise added to a solution of the methoxy compound (0.1 g, 0.24 mmol) prepared in Example 37 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (21 mg, 42%).

m.p. 215-216° C.; $^1$H NMR (CDCl$_3$) δ 2.37 (s, 3H), 2.61 (s, 3H), 4.95 (s, 2H), 6.56 (s, 1H), 6.73 (s, 1H), 6.91 (s, 1H), 7.11 (s, 1H), 7.51 (s, 1H), 7.75 (d, J=7.6 Hz, 2H), 7.92-7.98 (m, 3H), 8.46 (s, 1H).

Example 58

Preparation of [5-(3-hydroxy-5-methylphenyl)-4-(2-(2-acetamidophenyl)pyridin-4-yl)-pyrazol-1-yl]acetonitrile

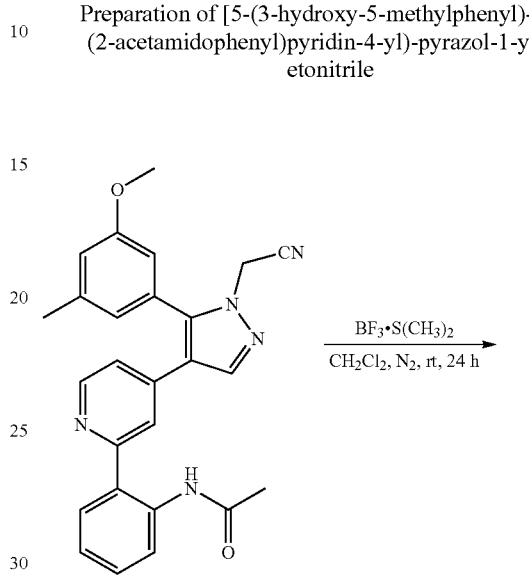

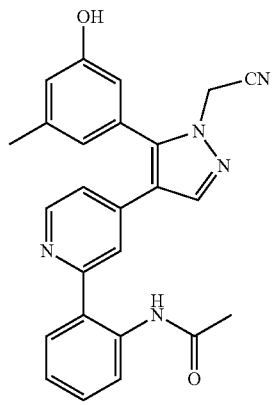

Borontrifluoride-dimethylsulfide (0.13 mL, 1.2 mmol) was dropwise added to a solution of the methoxy compound (52.5 mg, 0.12 mmol) prepared in Example 38 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (29 mg, 58%).

m.p. 133-134° C.; $^1$H NMR (CDCl$_3$) δ 2.13 (s, 3H), 2.37 (s, 3H), 4.92 (s, 2H), 6.68 (s, 1H), 6.74 (s, 1H), 6.94 (s, 1H), 7.02

(t, J=7.4 Hz, 1H), 7.12 (d, J=5.1 Hz, 1H), 7.20-7.27 (m, 2H), 7.50 (s, 1H), 7.99 (s, 1H), 8.37 (d, J=8.1 Hz, 1H), 8.44 (d, J=5.1 Hz, 1H), 12.14 (s, 1H).

Example 59

Preparation of [5-(3-hydroxy-5-methylphenyl)-4-(2-(3-acetamidophenyl)pyridin-4-yl)-pyrazol-1-yl]acetonitrile

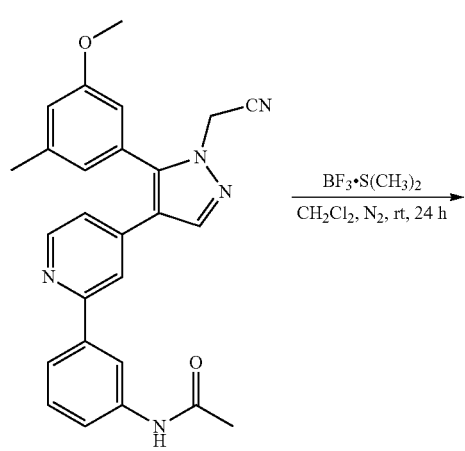

Borontrifluoride-dimethylsulfide (0.13 mL, 1.2 mmol) was dropwise added to a solution of the methoxy compound (52.5 mg, 0.12 mmol) prepared in Example 39 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (28 mg, 55%).

m.p. 142-143° C.; $^1$H NMR (CD$_3$OD) δ 2.16 (s, 3H), 2.36 (s, 3H), 5.14 (s, 2H), 6.66 (s, 1H), 6.75 (s, 1H), 6.89 (s, 1H), 7.23 (d, J=5.1 Hz, 1H), 7.36 (d, J=3.9 Hz, 2H), 7.65 (bs, 2H), 7.97 (s, 1H), 8.17 (s, 1H), 8.41 (d, J=5.2 Hz, 1H); $^{13}$C NMR (CD$_3$OD) δ 20.07, 22.46, 37.03, 113.48, 114.37, 117.72, 118.52, 118.69, 118.76, 119.85, 120.61, 121.12, 122.30, 128.80, 129.11, 139.00, 139.26, 139.62, 141.44, 141.61, 142.38, 149.04, 157.39, 158.40, 170.35.

Example 60

Preparation of [5-(3-hydroxy-5-methylphenyl)-4-(2-(4-cyanophenyl)pyridin-4-yl)-pyrazol-1-yl]acetonitrile

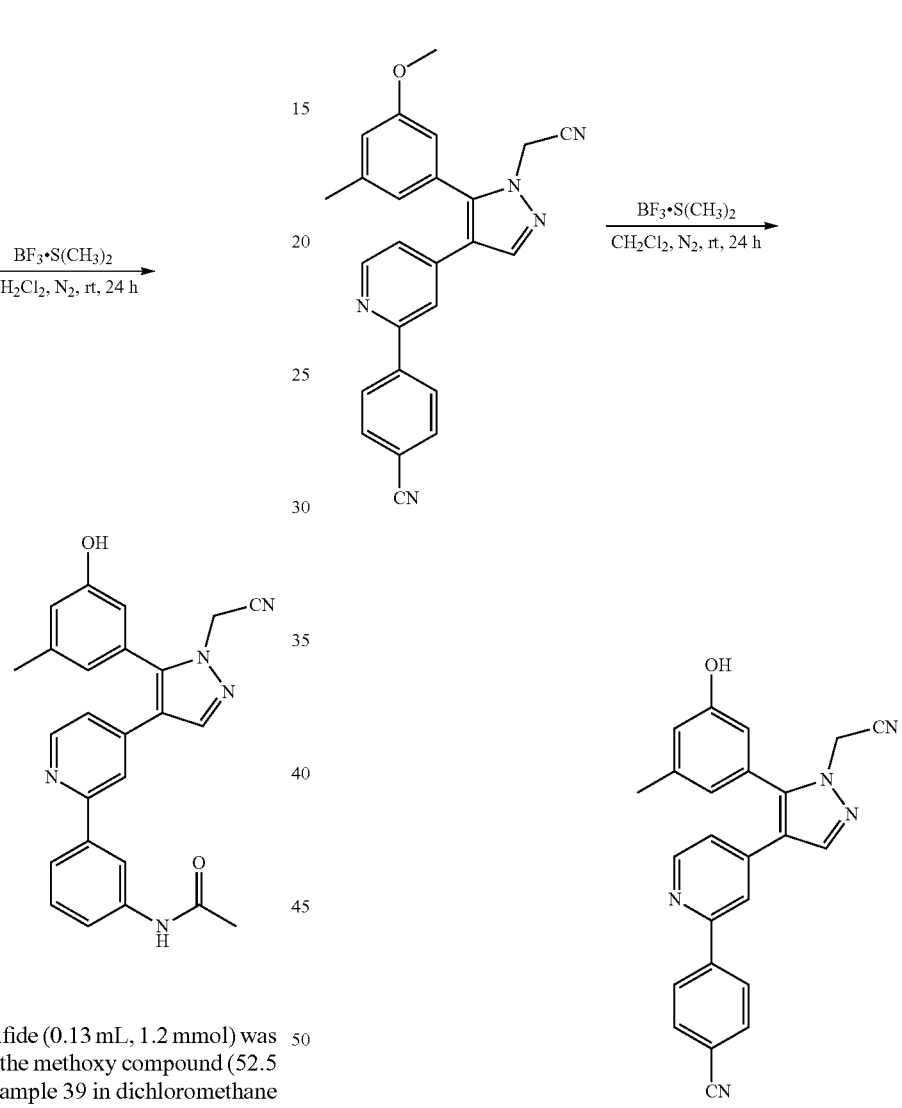

Borontrifluoride-dimethylsulfide (0.13 mL, 1.2 mmol) was dropwise added to a solution of the methoxy compound (48.6 mg, 0.12 mmol) prepared in Example 40 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (34 mg, 72%).

m.p. 225-227° C.; $^1$H NMR (CDCl$_3$) δ 2.37 (s, 3H), 4.96 (s, 2H), 6.61 (s, 1H), 6.75 (s, 1H), 6.90 (s, 1H), 7.14 (d, J=5.1 Hz,

1H), 7.54 (s, 1H), 7.66 (d, J=8.1 Hz, 2H), 7.83 (d, J=8.4 Hz, 2H), 8.00 (s, 1H), 8.50 (d, J=5.2 Hz, 1H).

Example 61

Preparation of [5-(3-hydroxy-5-methylphenyl)-4-(2-(4-dimethylaminophenyl)pyridin-4-yl)-pyrazol-1-yl]acetonitrile

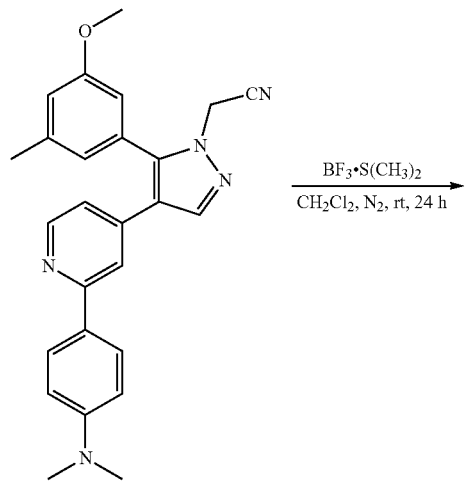

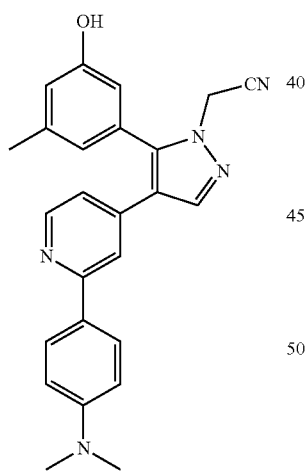

Borontrifluoride-dimethylsulfide (0.13 mL, 1.2 mmol) was dropwise added to a solution of the methoxy compound (50.1 mg, 0.12 mmol) prepared in Example 41 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (19 mg, 39%).

m.p. 153-154° C.; $^1$H NMR (CD$_3$OD) δ 2.40 (s, 3H), 3.09 (s, 6H), 5.20 (s, 2H), 6.72-6.86 (m, 4H), 6.98 (s, 1H), 7.46-7.56 (m, 3H), 7.84 (s, 1H), 8.33 (d, J=5.7 Hz, 1H), 8.41 (s, 1H).

Example 62

Preparation of [5-(3-hydroxy-5-methylphenyl)-4-(2-(4-phenoxyphenyl)pyridin-4-yl)-pyrazol-1-yl]acetonitrile

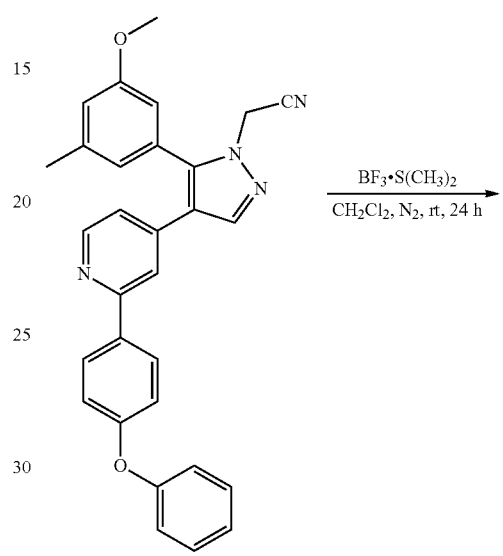

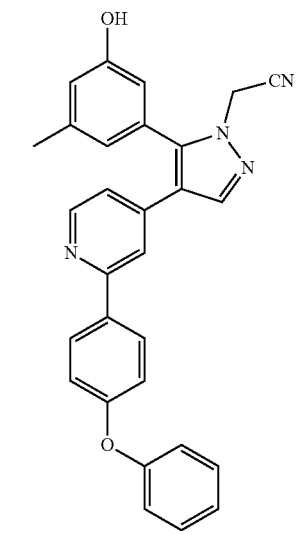

Borontrifluoride-dimethylsulfide (0.13 mL, 1.2 mmol) was dropwise added to a solution of the methoxy compound (56.7 mg, 0.12 mmol) prepared in Example 42 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL) and the organic layer was dried over anhydrous magnesium sulfate and distilled under vacuum. Purification through column chromatography (silica gel, ethyl acetate) afforded pure hydroxy products (34 mg, 61%).

m.p. 101-102° C.; $^1$H NMR (CDCl$_3$) δ 2.36 (s, 3H), 4.91 (s, 2H), 6.45 (s, 1H), 6.72 (s, 1H), 6.86 (s, 1H), 6.94-7.03 (m,

5H), 7.15 (t, 7.4 Hz, 1H), 7.36 (t, J=8.0 Hz, 2H), 7.49 (s, 1H), 7.65 (d, J=8.6 Hz, 2H), 7.95 (s, 1H), 8.32 (d, J=5.3 Hz, 1H), 9.11 (s, 1H) $^{13}$C NMR (CDCl$_3$) δ 21.47, 37.67, 113.97, 114.03, 118.68, 118.88, 118.98, 119.28, 119.58, 121.62, 123.80, 128.62, 129.90, 133.57, 139.59, 141.19, 141.71, 142.15, 149.05, 156.53, 157.20, 157.79, 158.47.

Example 63

Preparation of 2-(2-chloropyridin-5-yl)-1-(3-methoxy-5-methylphenyl)ethanone

To a solution of methyl 3-methoxy-5-methylbenzoate (9.0 g, 50 mmol) and 2-chloro-5-methylpyridine (7.0 g, 55 mmol) in tetrahydrofuran (90 mL) was dropwise added lithium hexamethyldisilazide (75 mL, 75 mmol, 1M In THF) at 0° C. under nitrogen atmosphere, and stirred at room temperature for 18 hours. After completion of the nucleophilic attack reaction, the reaction mixture was neutralized with a saturated ammonium chloride solution (150 mL) and extracted with ethyl acetate (300 mL×2). The organic layer was washed with brine, dried over anhydrous magnesium sulfate, and concentrated by vacuum distillation, and the concentrate (7.58 g, 55%) was used in the next reaction without further purification.

$^1$H NMR (CDCl$_3$) δ 2.29 (s, 3H), 3.74 (s, 3H), 3.83 (s, 2H), 6.84 (s, 1H), 7.14 (s, 1H), 7.29 (s, 1H), 7.35-7.39 (m, 2H), 8.12 (s, 1H); $^{13}$C NMR (CDCl$_3$) δ 17.55, 21.23, 52.00, 55.26, 111.11, 120.06, 122.73, 123.65, 131.09, 132.09, 139.48, 139.62, 148.43, 149.70, 159.49, 167.06.

Example 64

Preparation of 4-(2-chloropyridin-5-yl)-3-(3-methoxy-5-methylphenyl)-1H-pyrazol

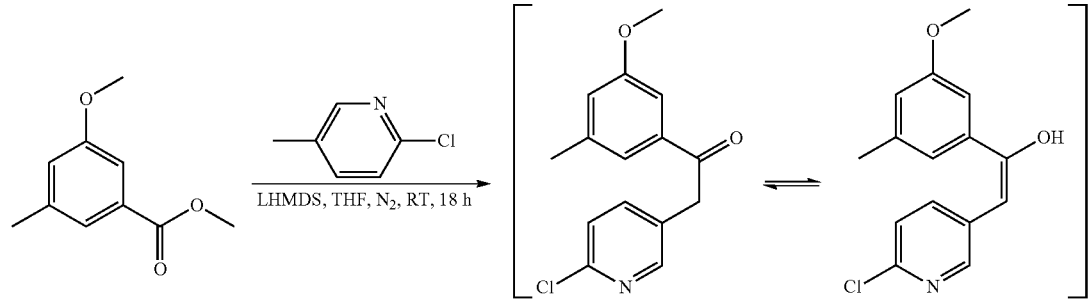

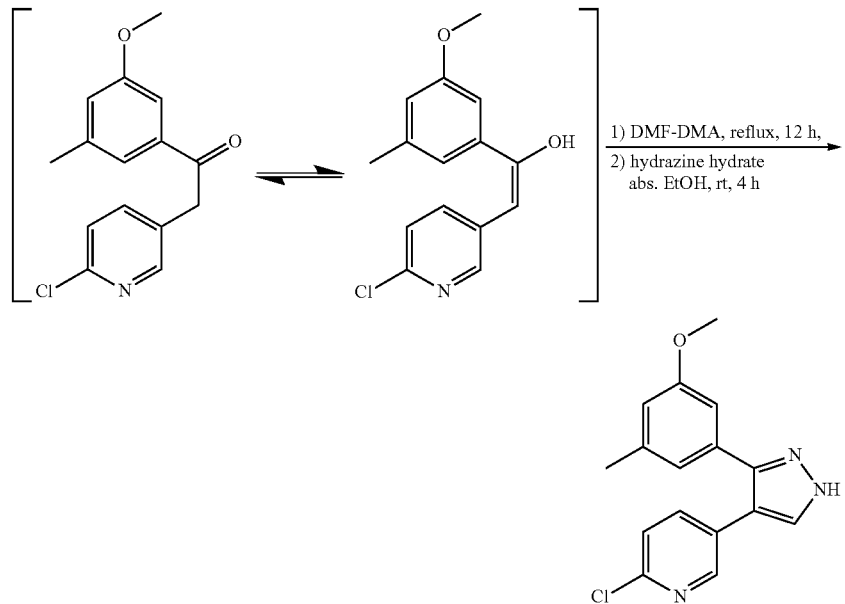

The keto-enol compound (7.28 g, 26.5 mmol) prepared in Example 63 was refluxed for 12 hours with N,N-dimethylformamide dimethylacetal (24 mL, 204 mmol). Excess N,N-dimethylformamide dimethylacetal was removed by vacuum distillation, and the reaction mixture was dissolved in anhydrous ethanol (150 mL). To this solution was dropwise added hydrazine hydrate (2.65 g, 53 mmol), and stirred at room temperature for 4 hours. The solvent was removed by vacuum distillation. The concentrate was purified through column chromatography (silica gel, ethyl acetate-hexane, 1:2, v/v) to afford the title compound as a red liquid (4.92 g, 62%).

$^1$H NMR (CDCl$_3$) δ 2.29 (s, 3H), 3.71 (s, 3H), 6.74 (s, 2H), 6.82 (s, 1H), 7.25 (d, J=8.3 Hz, 1H), 7.55 (d, J=8.3 Hz, 1H), 7.68 (s, 1H), 8.38 (s, 1H), 12.25 (s, 1H); $^{13}$C NMR (CDCl$_3$) δ 21.53, 55.50, 110.99, 114.96, 115.19, 121.30, 123.93, 128.18, 131.31, 138.10, 140.29, 148.56, 149.33, 159.90.

Example 65

Preparation of 4-(2-chloropyridin-5-yl)-3-(3-methoxy-5-methylphenyl)-1H-pyrazol-1-yl)acetonitrile and 4-(2-chloropyridin-5-yl)-5-(3-methoxy-5-methylphenyl)-1H-pyrazol-1-yl)acetonitrile

Example 65-1

Preparation of 4-(2-chloropyridin-5-yl)-3-(3-methoxy-5-methylphenyl)-pyrazol-1-yl)acetonitrile The compound obtained in Example 64 (4.6 g, 15.35 mmol) and potassium carbonate (10.6 g, 76.73 mmol) were added to acetone (100 mL) and refluxed for 2 hours. To this reaction mixture was dropwise added iodoacetonitrile (1.34 mL, 18.42 mmol), and refluxed over 2 hours. The acetone was removed by vacuum distillation, and the residue was treated in water (200 mL) and ethyl acetate (200 mL). The organic layer was dried over anhydrous magnesium sulfate and distillated in a vacuum. The concentrate was subjected to column chromatography (silica gel, ethyl acetate-hexane 2:3 v/v) to afford a mixture of 2:1 of regioisomers as yellow oil. These two regioisomers (4.16 g, 80%) were used in the next reaction step without separation.

Example 65-2

Preparation of 4-(2-chloropyridin-5-yl)-5-(3-methoxy-5-methylphenyl)-pyrazol-1-yl)acetonitrile $^1$H NMR (CDCl$_3$) δ 2.28 (s, 3H), 3.66 (s, 3H), 5.16 (s, 2H), 6.71 (s, 2H), 6.84 (s, 1H), 7.24 (d, J=8.3 Hz, 1H), 7.49 (dd, J=2.3, 5.9 Hz, 1H), 7.70 (s, 1H), 8.32 (s, 1H); $^{13}$C NMR (CDCl$_3$) δ 21.57, 39.89, 55.23, 110.80, 113.76, 115.28, 117.76, 121.47, 124.02, 127.24, 129.92, 132.57, 138.58, 140.12, 148.71, 149.92, 151.17, 159.69, 162.33.

General Synthesis Route

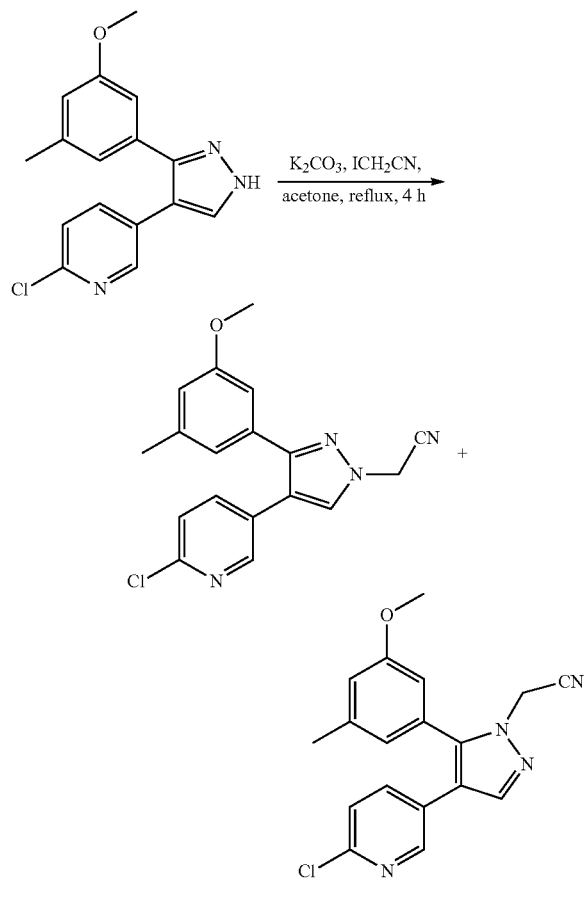
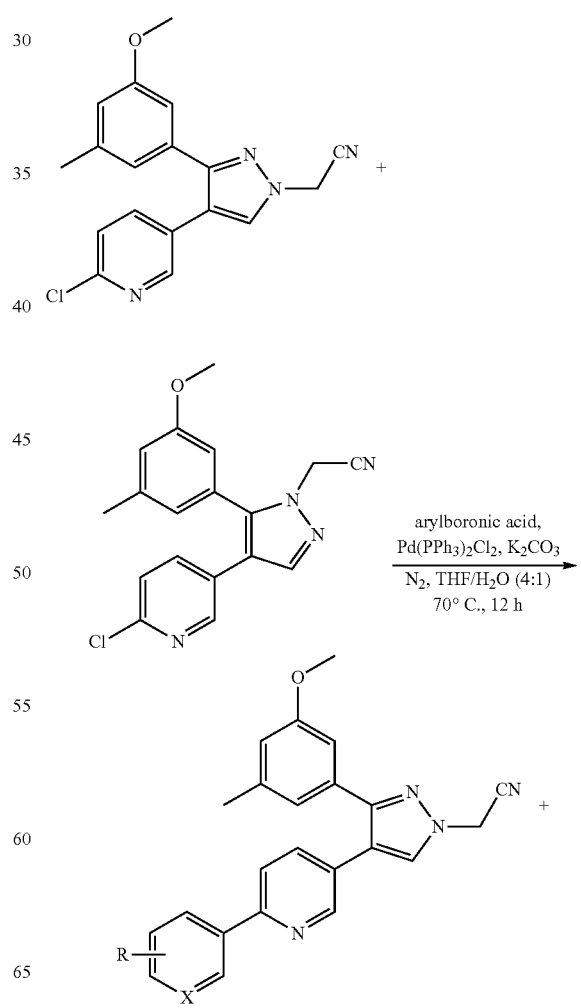

-continued

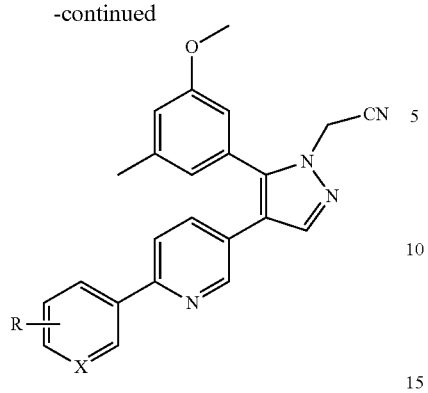

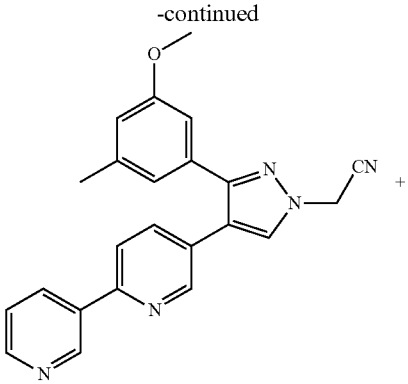

To a solvent mixture of THF and water (4:1, 10 mL) were added the mixture prepared in Example 65 (300 mg, 0.89 mmol), an appropriate arylbronic acid (0.974 mmol), dichlorobis(triphenylphosphine)palladium (II) (31 mg, 0.044 mmol) and potassium carbonate (130 mg, 0.89 mmol). The reaction system was purged with nitrogen gas for 10 min, and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Example 66

Preparation of [4-(2-pyridin-3-yl)pyridin-5-yl)-3-(3-methoxy-5-methylphenyl)-pyrazol-1-yl]acetonitrile

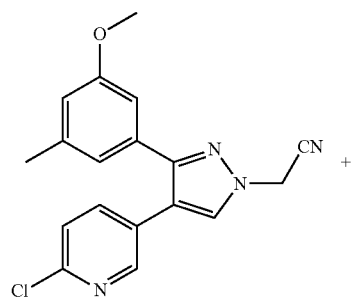

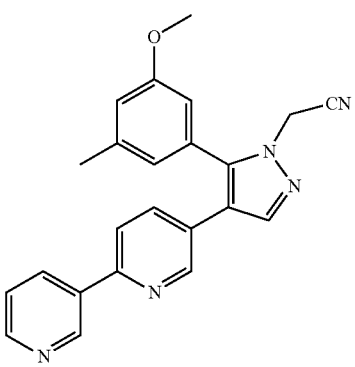

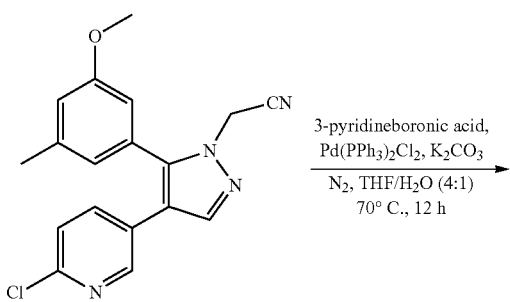

To a solvent mixture of THF and water (4:1, 10 mL) were added the mixture prepared in Example 65 (0.3 g, 0.89 mmol), 3-pyridineboronic acid (0.13 g, 1.07 mmol), dichlorobis(triphenylphosphine)palladium (II) (32 mg, 0.05 mmol) and potassium carbonate (0.13 g, 0.89 mmol). The reaction system was purged with nitrogen gas for 10 min, and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:3, v/v): (176 mg); m.p. 66-67° C.; $^1$H NMR (CDCl$_3$) δ 2.27 (s, 3H), 3.67 (s, 3H), 5.16 (s, 2H), 6.71 (s, 1H), 6.76 (s, 1H), 6.90 (s, 1H), 7.36-7.40 (m, 1H), 7.62-7.69 (m, 2H), 7.73 (s, 1H), 8.29 (d, J=7.7 Hz, 1H), 8.62-8.65 (m, 2H), 9.19 (s, 1H); $^{13}$C NMR (CDCl$_3$) δ 21.51, 39.85, 55.18, 110.91, 113.73, 115.30, 118.78, 119.96, 121.57, 123.62, 127.41, 129.76, 132.92, 134.10, 134.35, 136.58, 139.97, 148.09, 149.28, 149.93, 151.30, 153.13, 159.71.

Example 67

Preparation of [4-(2-(2-acetylphenyl)pyridin-5-yl)-3-(3-methoxy-5-methylphenyl)-pyrazol-1-yl]acetonitrile

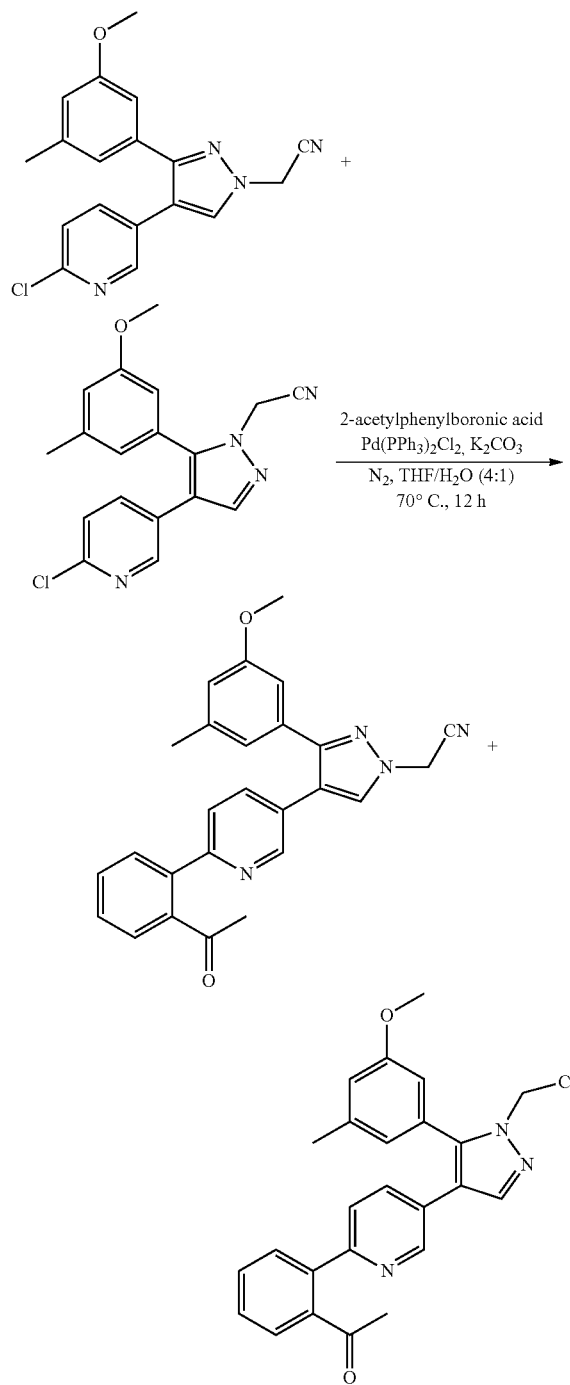

To a solvent mixture of THF and water (4:1, 10 mL) were added the mixture prepared in Example 65 (400 mg, 1.18 mmol), 2-acetylphenyl boronic acid (023 g, 1.42 mmol), dichlorobis(triphenylphosphine)palladium (II) (41 mg, 0.06 mmol) and potassium carbonate (0.16 g, 1.18 mmol). The reaction system was purged with nitrogen gas for 10 min, and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (155 mg); m.p. 176-177° C.; $^1$H NMR (CDCl$_3$) δ 2.25 (s, 3H), 2.28 (s, 3H), 3.70 (s, 3H), 5.14 (s, 2H), 6.72 (s, 1H), 6.76 (s, 1H), 6.89 (s, 1H), 7.44-7.65 (m, 6H), 7.70 (s, 1H), 8.54 (s, 1H); $^{13}$C NMR (CDCl$_3$) δ 21.51, 30.58, 39.79, 55.19, 110.80, 113.82, 115.30, 118.66, 121.54, 121.89, 127.06, 127.63, 128.80, 128.96, 130.02, 130.36, 132.92, 136.56, 138.15, 139.93, 141.68, 148.55, 151.23, 155.76, 159.71, 204.39.

Example 68

Preparation of [4-(2-(3-acetylphenyl)pyridin-5-yl)-3-(3-methoxy-5-methylphenyl)-pyrazol-1-yl]acetonitrile

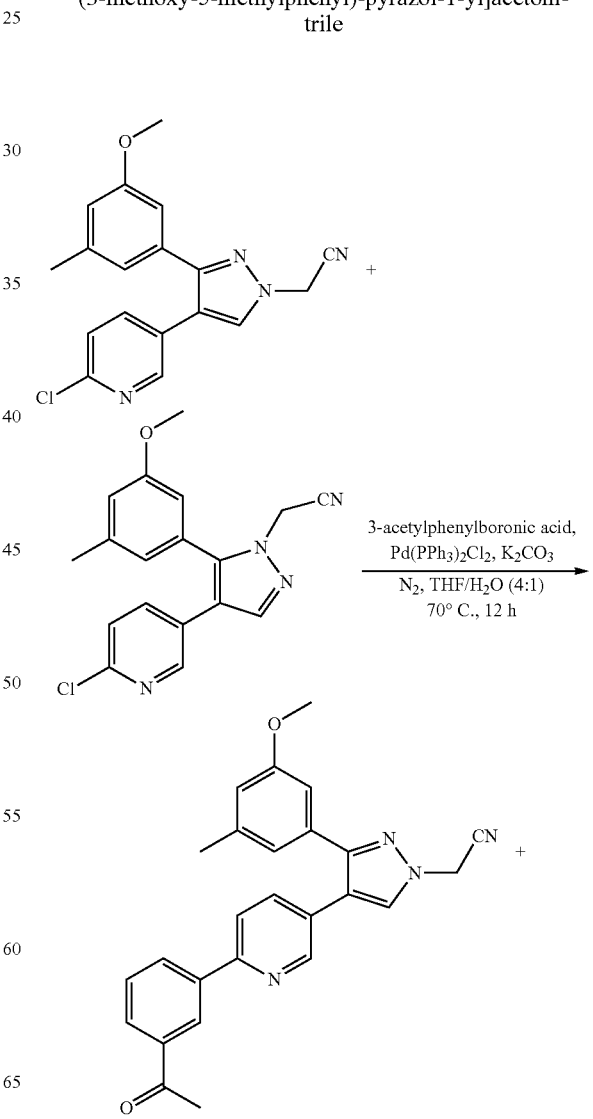

-continued

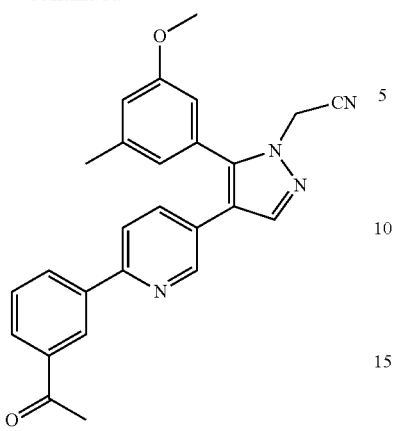

To a solvent mixture of THF and water (4:1, 10 mL) were added the mixture prepared in Example 65 (320 mg, 0.95 mmol), 3-acetylphenylboronic acid (0.19 g, 1.13 mmol), dichlorobis(triphenylphosphine)palladium (II) (33 mg, 0.04 mmol) and potassium carbonate (0.13 g, 0.95 mmol). The reaction system was purged with nitrogen gas for 10 min, and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (202 mg); m.p. 73-74° C.; $^1$H NMR (CDCl$_3$) δ 2.27 (s, 3H), 2.65 (s, 3H), 3.66 (s, 3H), 5.16 (s, 2H), 6.71 (s, 1H), 6.77 (s, 1H), 6.91 (s, 1H), 7.54 (t, J=7.7 Hz, 1H), 7.60-7.72 (m, 3H), 8.97 (d, J=7.5 Hz, 1H), 8.19 (d, J=7.5 Hz, 1H), 8.58 (s, 1H), 8.63 (s, 1H); $^{13}$C NMR (CDCl$_3$) δ 21.55, 26.83, 39.84, 55.19, 110.91, 113.92, 115.23, 118.77, 120.03, 121.58, 126.53, 127.18, 128.77, 129.14, 129.93, 131.22, 133.02, 136.57, 137.63, 139.31, 139.97, 149.01, 151.22, 154.56, 159.68, 198.12.

Example 69

Preparation of [4-(2-(2-pyridin-3-yl)pyridin-5-yl)-5-(3-methoxy-5-methylphenyl)-pyrazol-1-yl]acetonitrile

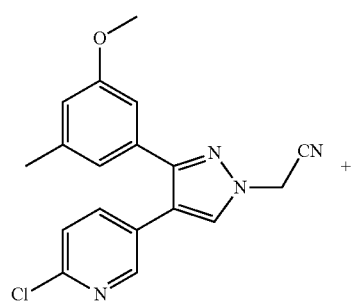

-continued

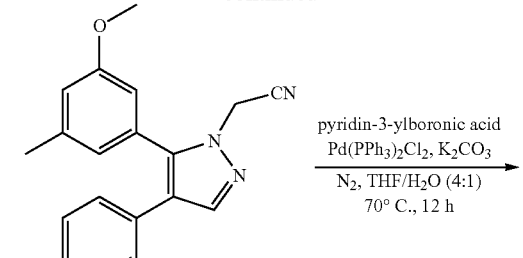

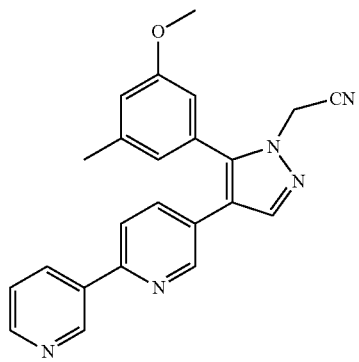

To a solvent mixture of THF and water (4:1, 10 mL) were added the mixture prepared in Example 65 (0.3 g, 0.89 mmol), 3-pyridineboronic acid (0.13 g, 1.07 mmol), dichlorobis(triphenylphosphine)palladium (II) (32 mg, 0.05 mmol) and potassium carbonate (0.13 g, 0.89 mmol). The reaction system was purged with nitrogen gas for 10 min, and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:3, v/v): (87 mg); m.p. 64-65° C.; in NMR (CDCl$_3$) δ 2.37 (s, 3H), 3.79 (s, 3H), 4.94 (s, 2H), 6.71 (s, 1H), 6.77 (s, 1H), 6.88 (s, 1H), 7.36-7.40 (m, 1H), 7.60-7.67 (m, 2H), 7.92 (s, 1H), 8.27 (d, J=7.7 Hz, 1H), 8.60-8.62 (m, 2H), 9.15 (s, 1H); $^{13}$C NMR (CDCl$_3$) δ 21.60, 37.81, 55.41, 112.42, 114.14, 116.71, 118.30, 120.26, 122.69, 123.62, 127.25, 128.99, 134.09, 134.43, 135.01, 139.48, 141.21, 141.39, 147.98, 148.25, 149.80, 152.64, 160.40.

Example 70

Preparation of [4-(2-(2-acetylphenyl)pyridin-5-yl)-5-(3-methoxy-5-methylphenyl)-pyrazol-1-yl]acetonitrile

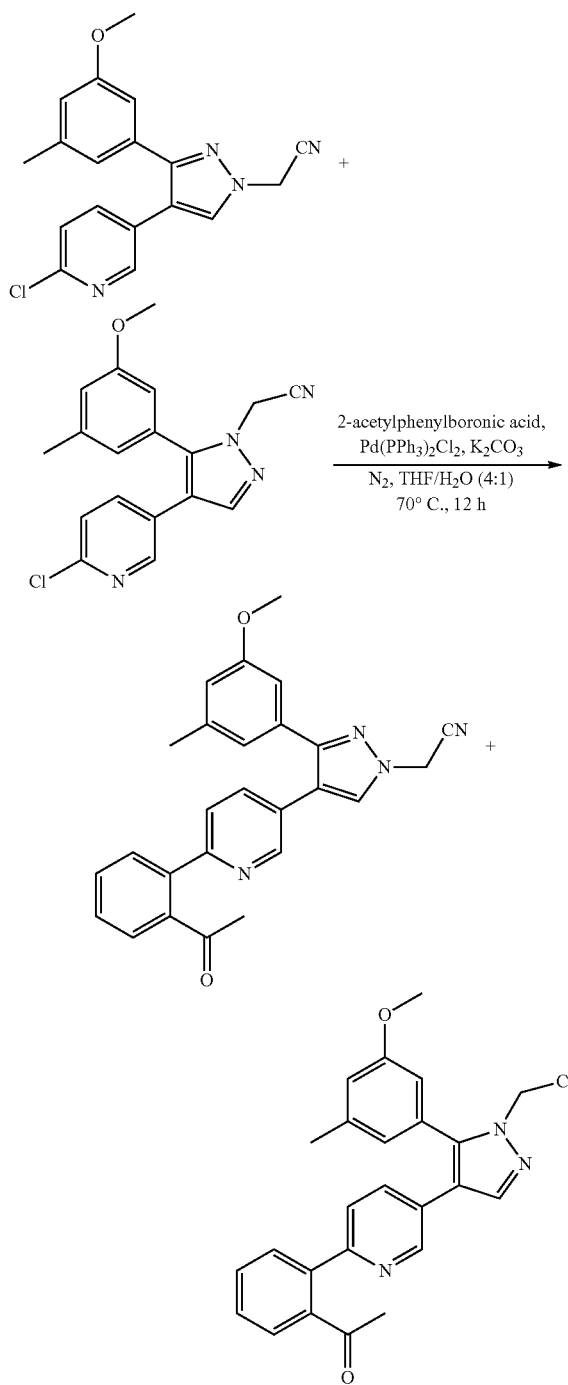

To a solvent mixture of THF and water (4:1, 10 mL) were added the mixture prepared in Example 65 (0.3 g, 0.89 mmol), 2-acetylphenylboronic acid (0.18 g, 1.07 mmol), dichlorobis(triphenylphosphine)palladium (II) (32 mg, 0.05 mmol) and potassium carbonate (0.13 g, 0.89 mmol). The reaction system was purged with nitrogen gas for 10 min, and stirred at 70° C. for 12 hours under nitrogen atmosphere. The reaction mixture was cooled to room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (72 mg); m.p. 72-73° C.; $^1$H NMR (CDCl$_3$) δ 2.18 (s, 3H), 2.36 (s, 3H), 3.78 (s, 3H), 4.95 (s, 2H), 6.68 (s, 1H), 6.75 (s, 1H), 6.86 (s, 1H), 7.43-7.59 (m, 6H), 7.91 (s, 1H), 8.49 (s, 1H); $^{13}$C NMR (CDCl$_3$) δ 21.55, 30.49, 37.81, 55.38, 112.37, 114.78, 116.72, 118.33, 122.13, 122.67, 126.78, 127.62, 128.64, 128.92, 128.99, 130.26, 134.89, 138.22, 139.49, 141.23, 141.33, 141.58, 147.50, 155.33, 160.40, 204.23.

Example 71

Preparation of [4-(2-(3-acetylphenyl)pyridin-5-yl)-5-(3-methoxy-5-methylphenyl)-pyrazol-1-yl]acetonitrile

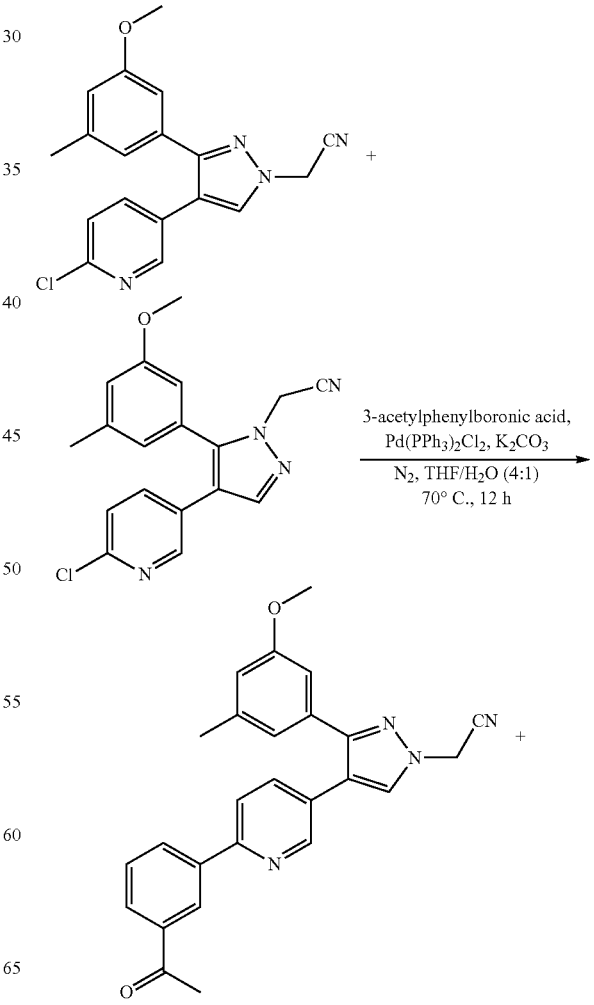

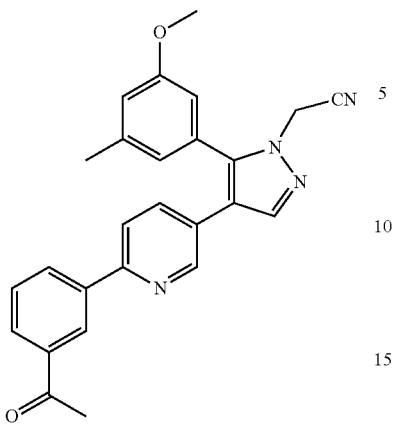

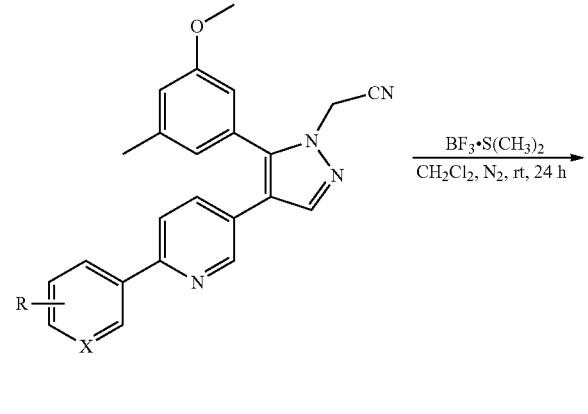

To a solvent mixture of THF and water (4:1, 10 mL) were added the mixture prepared in Example 65 (0.32 g, 0.95 mmol), 3-acetylphenylboronic acid (0.19 g, 1.13 mmol), dichlorobis(triphenylphosphine)palladium (II) (33 mg, 0.04 mmol) and potassium carbonate (0.13 g, 0.95 mmol). The reaction system was purged with nitrogen gas for 10 min, and stirred at 70° C. for 12 hours under nitrogen atmosphere. The reaction mixture was cooled at room temperature, washed with ice water (100 mL) and extracted with ethyl acetate (100 mL×3). The organic extract was dried over anhydrous magnesium sulfate and distilled under vacuum. The residue was subjected to prep-TLC using a solvent mixture of ethyl acetate/hexane to purify the desired products.

Purification yield by prep-TLC (silica gel, ethyl acetate-hexane, 1:2, v/v): (106 mg); m.p. 149-150° C.; $^1$H NMR (CDCl$_3$) δ 2.37 (s, 3H), 2.67 (s, 3H), 3.78 (s, 3H), 4.95 (s, 2H), 6.71 (s, 1H), 6.77 (s, 1H), 6.87 (s, 1H), 7.51-7.70 (m, 3H), 7.92 (s, 1H), 7.97 (d, J=7.6 Hz, 1H), 8.16 (d, J=7.8 Hz, 1H), 8.53 (s, 1H), 8.57 (d, J=1.2 Hz, 1H); $^{13}$C NMR (CDCl$_3$) δ 21.61, 26.82, 37.80, 55.41, 112.41, 114.22, 116.66, 118.39, 120.33, 122.71, 126.53, 126.96, 128.67, 129.04, 129.09, 131.18, 135.01, 137.58, 139.36, 139.48, 141.15, 141.36, 147.96, 154.21, 160.37, 198.06.

General Synthesis Route

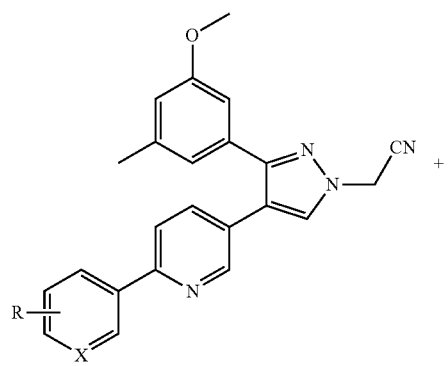

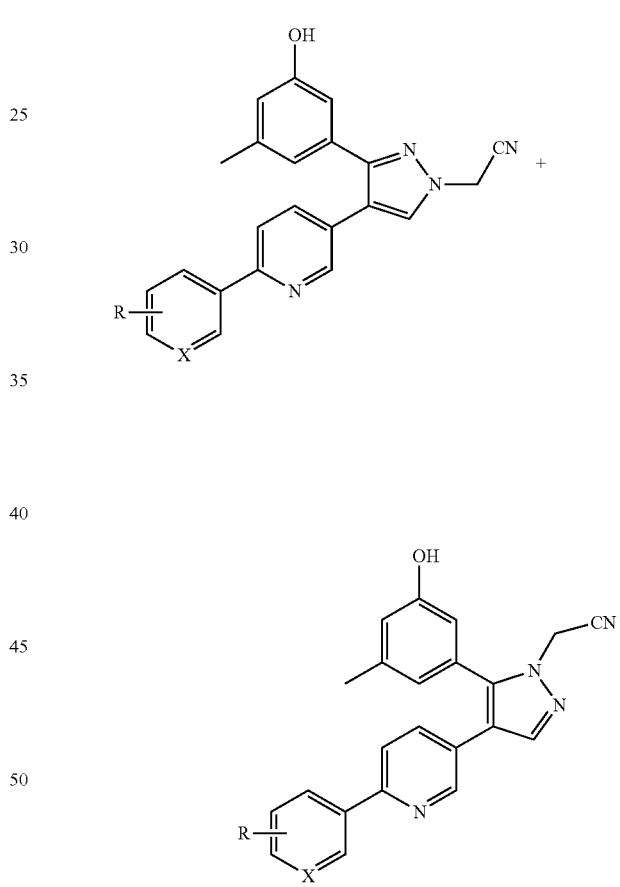

To a solution of the methoxy compound (0.12 mmol) in dichloromethane (4 mL) was dropwise added borontrifluoride-dimethylsulfide (0.13 mL, 1.2 mmol) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products.

Example 72

Preparation of [4-(2-pyridin-3-yl)pyridin-5-yl)-3-(3-hydroxy-5-methylphenyl)-pyrazol-1-yl]acetonitrile

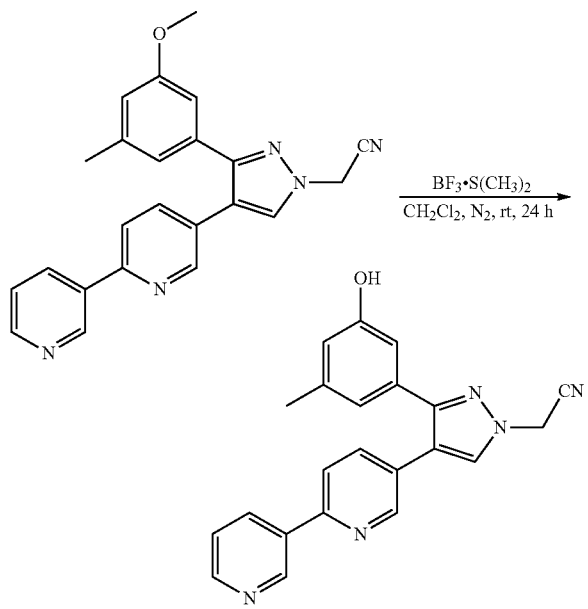

Borontrifluoride-dimethylsulfide (0.13 mL, 1.2 mmol) was dropwise added to a solution of the methoxy compound (45.8 mg, 0.12 mmol) prepared in Example 66 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (27 mg, 61%).

m.p. 258-259° C.; $^1$H NMR (CDCl$_3$) δ 2.31 (s, 3H), 5.60 (s, 2H), 6.59 (s, 2H), 6.73 (s, 1H), 7.49-7.54 (m, 1H), 7.74 (d, J=7.5 Hz, 1H), 8.06 (d, J=8.2 Hz, 1H), 8.25 (s, 1H), 8.45 (d, J=7.8 Hz, 1H), 8.61 (s, 2H), 9.29 (s, 1H), 9.39 (s, 1H); $^{13}$C NMR (CDCl$_3$) δ 21.53, 112.66, 116.34, 116.37, 117.27, 120.01, 120.71, 124.29, 128.23, 132.36, 133.80, 134.03, 134.16, 136.89, 139.61, 148.07, 149.12, 150.28, 150.32, 152.24, 157.74.

Example 73

Preparation of [4-(2-(2-acetylphenyl)pyridin-5-yl)-3-(3-hydroxy-5-methylphenyl)-pyrazol-1-yl]acetonitrile

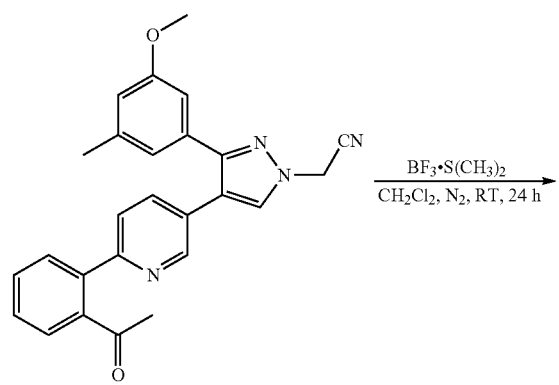

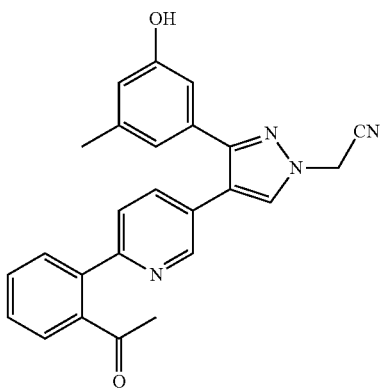

Borontrifluoride-dimethylsulfide (0.13 mL, 1.2 mmol) was dropwise added to a solution of the methoxy compound (50.7 mg, 0.12 mmol) prepared in Example 67 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (27 mg, 55%).

m.p. 108-109° C.; $^1$H NMR (CDCl$_3$) δ 2.24 (s, 3H), 2.39 (s, 3H), 5.13 (s, 2H), 6.39 (s, 1H), 6.58 (s, 1H), 6.99 (s, 1H), 7.46-7.66 (m, 6H), 7.70 (s, 1H), 8.46 (s, 1H); $^{13}$C NMR (CDCl$_3$) δ 21.38, 29.89, 39.77, 112.53, 113.80, 116.70, 118.53, 120.26, 122.31, 127.24, 128.01, 128.85, 129.05, 129.83, 130.97, 132.38, 137.25, 138.70, 140.20, 140.65, 148.32, 151.07, 156.37.

Example 74

Preparation of [4-(2-(2-acetylphenyl)pyridin-5-yl)-5-(3-hydroxy-5-methylphenyl)-pyrazol-1-yl]acetonitrile

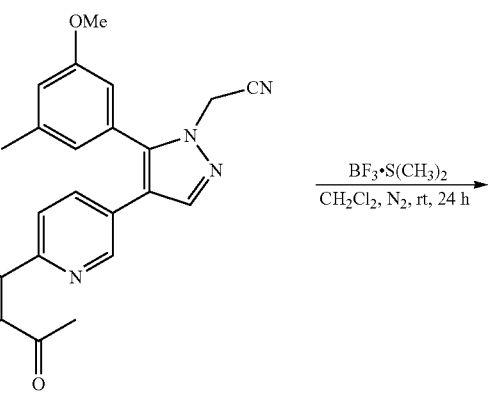

-continued

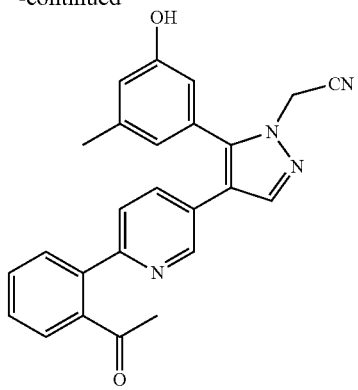

Borontrifluoride-dimethylsulfide (0.13 mL, 1.2 mmol) was dropwise added to a solution of the methoxy compound (50.7 mg, 0.12 mmol) prepared in Example 70 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (30 mg, 62%).

m.p. 142-143° C.; $^1$H NMR (CDCl$_3$) δ 2.23 (s, 3H), 2.27 (s, 3H), 4.92 (s, 2H), 6.45 (s, 1H), 6.62 (s, 1H), 6.71 (s, 1H), 7.46-7.63 (m, 6H), 7.88 (s, 1H), 8.41 (s, 1H); $^{13}$C NMR (CDCl$_3$) δ 21.37, 29.95, 37.78, 113.96, 114.07, 117.74, 118.48, 121.59, 122.25, 127.46, 127.52, 128.32, 128.62, 129.22, 130.69, 136.18, 137.35, 139.38, 141.22, 141.39, 141.60, 146.14, 154.62, 157.66.

Example 75

Preparation of [4-(2-(3-acetylphenyl)pyridin-5-yl)-3-(3-hydroxy-5-methylphenyl)-pyrazol-1-yl]acetonitrile

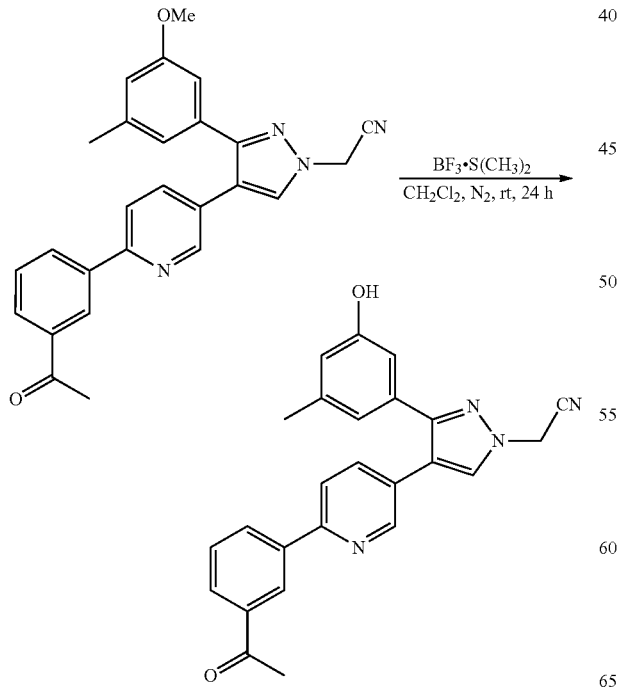

Borontrifluoride-dimethylsulfide (0.13 mL, 1.2 mmol) was dropwise added to a solution of the methoxy compound (50.7 mg, 0.12 mmol) prepared in Example 68 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (39 mg, 69%).

m.p. 103-105° C.; $^1$H NMR (CDCl$_3$) δ 2.30 (s, 3H), 2.60 (s, 3H), 5.12 (s, 2H), 6.60 (s, 1H), 6.69 (s, 1H), 7.03 (s, 1H), 7.39-7.48 (m, 2H), 7.61-7.64 (m, 2H), 7.79 (d, J=7.6 Hz, 1H), 7.95 (d, J=7.5 Hz, 1H), 8.30 (s, 1H), 8.50 (s, 1H), 8.84 (s, 1H) $^{13}$C NMR (CDCl$_3$) δ 21.48, 26.78, 39.82, 112.17, 113.66, 117.03, 118.13, 120.49, 120.77, 126.74, 127.72, 129.11, 130.06, 131.26, 132.48, 137.49, 137.58, 138.19, 140.74, 147.90, 151.07, 154.30, 156.70, 198.22.

Example 76

Preparation of [4-(2-(3-acetylphenyl)pyridin-5-yl)-5-(3-hydroxy-5-methylphenyl)-pyrazol-1-yl]acetonitrile

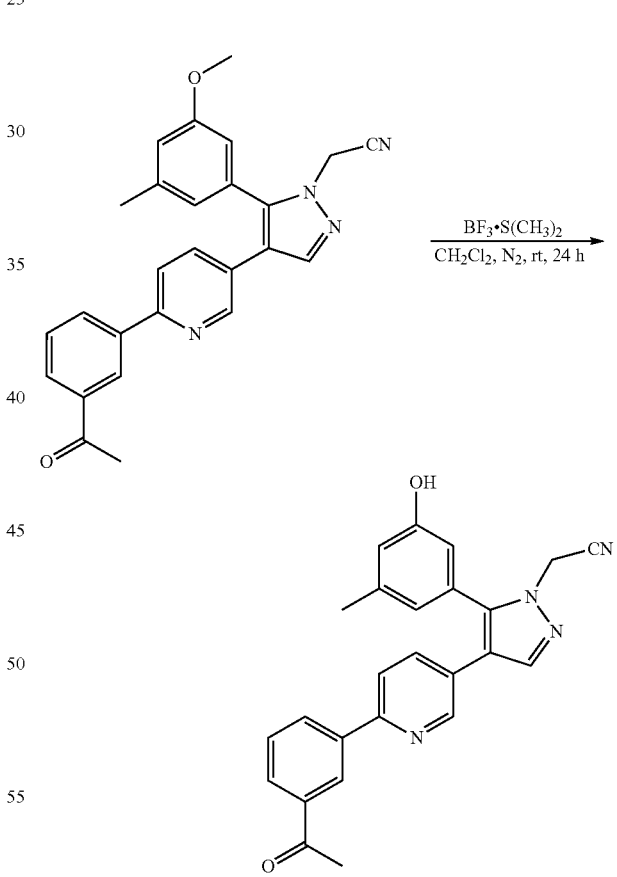

Borontrifluoride-dimethylsulfide (0.13 mL, 1.2 mmol) was dropwise added to a solution of the methoxy compound (50.7 mg, 0.12 mmol) prepared in Example 71 in dichloromethane (4 mL) at room temperature under nitrogen atmosphere, and stirred for 24 hours. The reaction mixture was concentrated by vacuum distillation. The residue was treated in ethyl acetate (100 mL) and brine (50 mL), and the organic layer was dried over anhydrous magnesium sulfate and distilled under vacuum. Purification through column chromatography (silica gel, ethyl acetate) afforded pure hydroxy products (35 mg, 71%).

m.p. 100-101° C.; $^1$H NMR (CDCl$_3$) δ 2.31 (s, 3H), 2.65 (s, 3H), 4.96 (s, 2H), 6.55 (s, 1H), 6.67 (s, 1H), 6.79 (s, 1H), 7.55-7.74 (m, 3H), 7.90 (s, 1H), 7.98 (d, J=75 Hz, 1H), 8.10 (d, J=7.3 Hz, 1H), 8.49 (bs, 2H); $^{13}$C NMR (CDCl$_3$) δ 21.45, 26.81, 37.75, 113.82, 114.03, 117.46, 118.45, 121.49, 121.74, 126.91, 127.88, 12.88, 129.38, 131.48, 136.59, 137.63, 139.40, 141.53, 141.68, 146.30, 153.28, 157.69, 198.13.

EXPERIMENTAL EXAMPLES

Experimental Example 1

Kinase Screening

Kinase screening was performed using a "HotSpot" assay platform commercially available from Reaction Biology Corporation. For this kinase screening, reaction buffers were based on 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, and 1% DMSO, with supplementary factors necessary for respective kinase reactions added thereto. In each enzyme reaction, 20 μM of each kinase was used together with a fresh reaction buffer and appropriate supplementary factors. A solution of each compound in DMSO was added in a suitable concentration to the reaction buffer. Kinase reaction started with the introduction of 339-ATP (specific activity 500 μCi/μl) and continued for 2 hours at room temperature.

1) Screening of Compounds Over 45 Different Kinases

Each compound was tested twice at a single dose concentration of 10 μM. A 5-dose IC50 mode with dilutions starting at 20 μM concentration was applied against Staurosporine as a reference standard. The reaction was performed with 10 μM ATP.

2) ROS Kinase Screening

Experimental compounds were tested in a 10-dose IC50 mode starting from 20 μM. A 5-dose IC$_{50}$ mode with dilutions starting at 20 μM concentration was applied against Staurosporine as a reference standard. The reaction was performed with 10 μM ATP.

As shown in the data of Table 2 obtained by screening over 45 different kinases, the compound prepared in Example 10 had no inhibitory activity against almost all of the tested kinases, except for ROS kinase for which high potency and activity was selectively exhibited.

TABLE 2

| Kinase | Activity (%)$^a$ | Inhibition (%)$^b$ |
|---|---|---|
| ABL1 | 79.56 | 20.44 |
| AKT1 (dPH, S473D) | 102.97 | −2.97 |
| Aurora A | 78.25 | 21.75 |
| BRAF | 91.03 | 8.97 |
| CDK1/cyclinB | 96.36 | 3.64 |
| CHK1 | 97.64 | 2.36 |
| CK1epsilon | 90.68 | 9.32 |
| c-Kit | 97.15 | 2.85 |
| c-MET | 94.18 | 5.82 |
| c-Src | 83.82 | 16.18 |
| DAPK1 | 101.17 | −1.17 |
| DNA-PK | 93.44 | 6.56 |
| EGFR | 102.23 | −2.23 |
| EPHA1 | 76.73 | 23.27 |
| FAK/PTK2 | 96.57 | 3.43 |

TABLE 2-continued

| Kinase | Activity (%)$^a$ | Inhibition (%)$^b$ |
|---|---|---|
| FGFR1 | 108.05 | −8.05 |
| FGR | 96.66 | 3.34 |
| FLT1 | 101.67 | −1.67 |
| FYN | 107.86 | −7.86 |
| HIPK1 | 103.43 | −3.43 |
| IKKa/CHUK | 98.63 | 1.37 |
| IR | 92.99 | 7.01 |
| JAK1 | 90.85 | 9.15 |
| JNK1a1 | 96.17 | 3.83 |
| KDR/VEGFR2 | 105.84 | −5.84 |
| LCK | 89.72 | 10.28 |
| LYN | 101.45 | −1.45 |
| MEK1 | 106.97 | −6.97 |
| MST4 | 101.54 | −1.54 |
| MUSK | 100.42 | −0.42 |
| P38a/MAPK14 | 94.73 | 5.27 |
| p70S6K | 94.21 | 5.79 |
| PAK4 | 98.63 | 1.37 |
| PIM1 | 94.09 | 5.91 |
| PKCa | 90.77 | 9.23 |
| PLK1 | 94.15 | 5.85 |
| RAF1 | 79.61 | 20.39 |
| RET | 93.35 | 6.65 |
| RocK1 | 88.28 | 11.72 |
| RON/MST1R | 71.08 | 28.82 |
| Ros/Ros1 | 6.08 | 93.92 |
| SYK | 91.77 | 8.23 |
| TIE2/TEK | 91.83 | 8.17 |
| TRKA/NTRK1 | 100.14 | −0.14 |
| YES | 102.59 | −2.59 |

$^a$% activity of each enzyme at a single dose concentration of 10 μM (%), compared to enzyme activity in DMSO control
$^b$% Inhibition IC$_{50}$ values of various compounds against ROS are summarized in Table 3, below. The compound prepared in Example 10 has an IC$_{50}$ of 199 nM, showing the most potent activity against ROS among the ROS kinase-selective compounds reported as of May, 2009, but for 0.9 nM of Staurosporine, a non-selective anticancer agent. Also, the compound prepared in Example 44 showed high potency and ROS selectivity with an IC$_{50}$ of 209 nM.

TABLE 3

| Compound | Inhibitory Activity against ROS (IC$_{50}$) | Notes |
|---|---|---|
| Example 10 | 199 nM | Selective for ROS |
| Example 44 | 209 nM | Selective for ROS |
| Staurosporine (Reference) | 0.9 nM | Non-selective compound |
| PP2 (Control) | 5,200 nM | Data from Reaction Biology corporation |
| AG1478 (Control) | 13,600 nM | Data from Reaction Biology corporation |

With reference to FIG. 1, ROS enzyme activities are plotted against the concentrations of the pyrazole compound of Example 10 and the reference Staurosporine, showing IC$_{50}$ values thereof.

FORMULATION EXAMPLES

The novel compounds, represented by Formula 1, of the present invention can be formulated into various dosage forms according to purpose. Several formulations with the pyrazole compounds of Formula 1 acting as an active ingredient are illustrated in the following examples, but are not given to limit the scope of the present invention.

Formulation Example 1

Tablets (Direct Compression)

After being sieved, 5.0 mg of the active ingredient was washed with 14.1 mg of lactose, 0.8 mg of crospovidone USNF, and 0.1 mg of magnesium stearate, and directly compressed into tablets.

Formulation Example 2

Tablets (Wet Granulation)

5.0 mg of the active ingredient was sieved and mixed with 16.0 mg of lactose and 4.0 mg of starch. To this mixture was added a suitable amount of a solution of 0.3 mg of polysorbate 80 in pure water, followed by micro granulation. The micro granules thus obtained were dried, sieved, and mixed with 2.7 mg of colloidal silicon dioxide and 2.0 mg of magnesium stearate. The mixture was compressed into tablets.

Formulation Example 3

Powders and Capsules

After being sieved, 5 mg of the active ingredient was admixed with 14.8 mg of lactose, 10.0 mg of polyvinyl pyrrolidone and 0.2 mg of magnesium stearate. The admixture was loaded into hard No. 5 gelatin capsules using a suitable device.

Formulation Example 4

Injections

An injection comprising 180 mg of mannitol, 26 mg of $Na_2HO_4 \cdot 12H_2O$ and 2974 mg of distilled water in addition to 100 mg of the active ingredient was prepared.

INDUSTRIAL APPLICABILITY

Acting as selective potent inhibitor against ROS kinase, as described hitherto, the novel compounds of the present invention are usable as an active ingredient for anticancer agents used in the treatment of brain cancer, CNS malignancies, glioblastoma multiforme and glioblastoma.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A pyrazole compound represented by the following Formula 1:

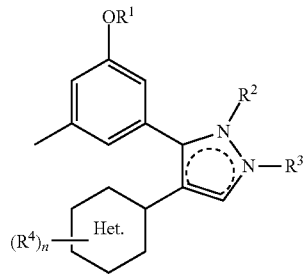

[1]

wherein

is a pyrimidyl ring;

$R^1$ is a hydrogen atom; $C_1$-$C_6$ alkyl; or acetyl;

one of $R^2$ and $R^3$ represents an electron pair forming a double bond within the pyrazole ring, while the other is a hydrogen atom; cyano; $C_1$-$C_6$ alkyl; or cyano $C_1$-$C_6$ alkyl;

$R^4$ is a hydrogen atom; a halogen atom; hydroxy; azetidinyl; hydroxyazetidinyl; pyrrolidyl; hydroxypyrrolidyl; pyridyl; phenyl; or substituted phenyl having 1 to 3 substituents selected independently from the group consisting of cyano, amino, $C_1$-$C_6$ alkylamino, di($C_1$-$C_6$ alkyl)amino, $C_1$-$C_6$ alkylcarbonyl, $C_1$-$C_6$ alkylamide, and phenoxy; and n is an integer of 1-3, representing the number of the substituent $R^4$;

or a pharmaceutically acceptable salt thereof.

2. The pyrazole compound according to claim 1, wherein

is pyrimidin-4-yl;

$R^1$ is selected from the group consisting of a hydrogen atom, methyl, ethyl, n-propyl, isopropyl, n-butyl, sec-butyl, tert-butyl, n-pentyl, isopentyl, n-hexyl, cyclohexyl, and acetyl;

one of $R^2$ and $R^3$ is an electron pair forming a double bond within the pyrazole ring, while the other is selected from the group consisting of a hydrogen atom, cyano, methyl, ethyl, n-propyl, isopropyl, n-butyl, sec-butyl, tert-butyl, cyanomethyl, cyanoethyl, and cyanopropyl;

$R^4$ is selected from a hydrogen atom, a chloro atom, a fluoro atom, a bromo atom, hydroxy, azetidinyl, 3-hydroxyazetidinyl, pyrrolidyl, 2-hydroxypyrrolidyl, 3-hydroxypyrrolidyl, 2-pyridyl, 3-pyridyl, 4-pyridyl, phenyl, 2-cyanophenyl, 3-cyanophenyl, 4-cyanophenyl, 2-aminophenyl, 3-aminophenyl, 4-aminophenyl, 2-(methylamino)phenyl, 3-(methylamino)phenyl, 4-(methylamino)phenyl, 2-(dimethylamino)phenyl, 3-(dimethylamino)phenyl, 4-(dimethylamino)phenyl, 2-(ethylamino)phenyl, 3-(ethylamino)phenyl, 4-(ethylamino)phenyl, 2-(diethylamino)phenyl, 3-(diethylamino)phenyl, 4-(diethylamino)phenyl, 2-acetophenyl, 3-acetophenyl, 4-acetophenyl, 2-(ethylcarbonyl)phenyl, 3-(ethylcarbonyl)phenyl, 4-(ethylcarbonyl)phenyl, 2-(acetylamino)phenyl, 3-(acetylamino)phenyl, 4-(acetylamino)phenyl, 2-phenoxyphenyl, 3-phenoxyphenyl, and 3-phenoxyphenyl; and n is an integer of 1, 2 or 3, representing the number of the substituent $R^4$;

or a pharmaceutically acceptable salt thereof.

3. The pyrazole compound according to claim 1, selected from the group consisting of:

4-[2-chloro-6-(2(S)-hydroxypropylamino)-pyrimidin-4-yl]-3-(3-methoxy-5-methylphenyl)-1H-pyrazol,

[4-[2-chloro-6-(2(S)-hydroxy-propylamino)-pyrimidin-4-yl]-3-(3-methoxy-5-methylphenyl)-pyrazol-1-yl]acetonitrile,

[4-[6-(2(S)-hydroxypropylamino)-2-pyridin-3-yl-pyrimidin-4-yl]-3-(3-methoxy-5-methylphenyl)-pyrazol-1-yl]acetonitrile,

[4-[6-(2(S)-hydroxypropylamino)-2-pyridin-3-yl-pyrimidin-4-yl]-3-(3-hydroxy-5-methylphenyl)-pyrazol-1-yl]acetonitrile,

[4-[6-(2(S)-acetoxypropylamino)-2-pyridin-3-yl-pyrimidin-4-yl]-3-(3-acetoxy-5-methylphenyl)-pyrazol-3-yl]acetonitrile,

[4-[2-(3-hydroxyazetindin-1-yl)-pyrimidin-4-yl]-3-(3-methoxy-5-methylphenyl)-pyrazol-1-yl]acetonitrile,

[4-[2-(3-hydroxyazetindin-1-yl)-pyrimidin-4-yl]-3-(3-hydroxy-5-methylphenyl)-pyrazol-1-yl]acetonitrile,

[4-[2-(3(S)-hydroxypyrrolidin-1-yl)-pyrimidin-4-yl]-3-(3-methoxy-5-methylphenyl)-pyrazol-1-yl]acetonitrile, and [4-[2-(3(S)-hydroxypyrrolidin-1-yl)-pyrimidin-4-yl]-3-(3-hydroxy-5-methylphenyl)-pyrazol-1-yl]acetonitrile.

4. A method for preparing a pyrazole compound represented by Formula 1 comprising:

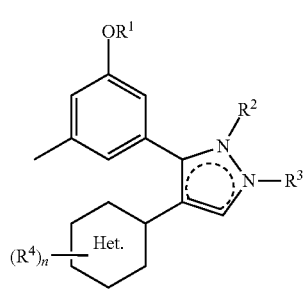

[1]

(a) a step of preparing a keto-enol tautomer of Formula 4, by allowing a methyl 3-methoxy-5-methylbenzoate compound of Formula 2 to undergo a nucleophilic attack at its carboxylic carbon by a heteroaromatic compound of Formula 3 in the presence of lithium hexamethyldisilazide (LHMDS):

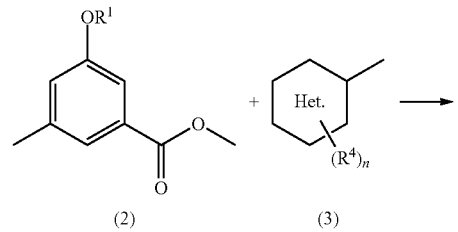

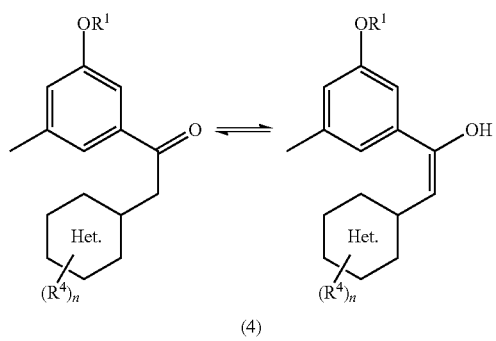

wherein

$R^1$, $R^4$, and n are the same as defined in claim 1; and (b) a step of preparing a pyrazole compound of Formula 1 by reacting said keto-enol tautomer of Formula 4 in the presence of a hydrazine hydrate and in absolute ethanol,

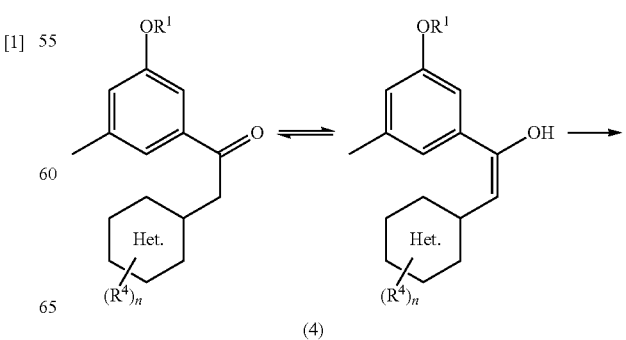

-continued
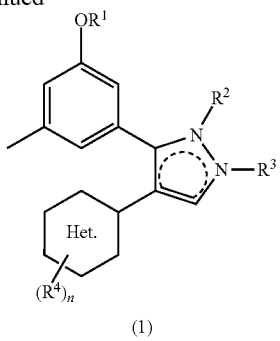
wherein
$R^1$, $R^4$, and n are respectively the same as defined in claim 1.
5. The pyrazole compound of claim 1, wherein at least one $R^4$ is a pyrrolidyl; hydroxypyrrolidyl; or pyridyl.
6. The pyrazole compound of claim 1 which has the formula:
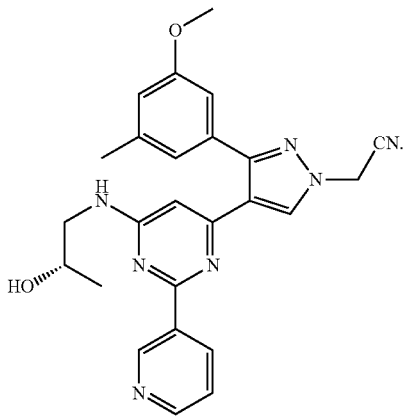
* * * * *